US006306588B1

(12) United States Patent
Solus et al.

(10) Patent No.: US 6,306,588 B1
(45) Date of Patent: Oct. 23, 2001

(54) POLYMERASES FOR ANALYZING OR TYPING POLYMORPHIC NUCLEIC ACID FRAGMENTS AND USES THEREOF

(75) Inventors: Joseph Solus, Gaithersburg; Shuwei Yang, Rockville; Deb K. Chatterjee, North Potomac, all of MD (US)

(73) Assignee: Invitrogen Corporation, Carlsbad, CA (US)

( * ) Notice: Subject to any disclaimer, the term of this patent is extended or adjusted under 35 U.S.C. 154(b) by 0 days.

(21) Appl. No.: 09/019,160

(22) Filed: Feb. 6, 1998

Related U.S. Application Data
(60) Provisional application No. 60/070,562, filed on Jan. 6, 1998, and provisional application No. 60/037,393, filed on Feb. 7, 1997.

(51) Int. Cl.$^7$ .............................. C12Q 1/68; C12P 19/34; C12N 11/16; C07K 17/00; A61K 35/14

(52) U.S. Cl. ........................... 435/6; 435/91.2; 435/174; 530/350; 530/382; 530/388.21

(58) Field of Search .............................. 435/6, 91.2, 174; 530/350, 820, 388.21

(56) References Cited

U.S. PATENT DOCUMENTS

| | | | |
|---|---|---|---|
| 5,075,217 | 12/1991 | Weber | 435/6 |
| 5,306,616 | 4/1994 | Lupski et al. | 435/6 |
| 5,364,759 | 11/1994 | Caskey et al. | 435/6 |
| 5,369,004 | 11/1994 | Polymeropoulos et al. | 435/6 |
| 5,378,602 | 1/1995 | Polymeropoulos et al. | 435/6 |
| 5,409,818 | 4/1995 | Davey et al. | 435/91.21 |
| 5,413,908 | 5/1995 | Jeffreys | 435/6 |
| 5,436,142 | 7/1995 | Wigler et al. | 435/91.2 |
| 5,436,149 | * 7/1995 | Barnes | 435/194 |
| 5,455,166 | 10/1995 | Walker | 435/91.2 |
| 5,459,039 | 10/1995 | Modrich et al. | 435/6 |
| 5,468,610 | 11/1995 | Polymeropoulos et al. | 435/6 |
| 5,468,613 | 11/1995 | Erlich et al. | 435/6 |
| 5,556,955 | 9/1996 | Vergnaud | 536/24.31 |
| 5,565,340 | 10/1996 | Chenchik et al. | 435/91.2 |
| 5,599,672 | 2/1997 | Liang et al. | 435/6 |
| 5,618,711 | 4/1997 | Gelfand et al. | 435/194 |
| 5,624,833 | 4/1997 | Gelfand et al. | 435/194 |
| 5,766,847 | 6/1998 | Jäckle et al. | 435/6 |
| 5,885,813 | 3/1999 | Davis et al. | 435/183 |
| 5,912,155 | 6/1999 | Chatterjee et al. | 435/194 |
| 5,939,301 | 8/1999 | Hughes, Jr. et al. | 435/194 |
| 5,948,614 | 9/1999 | Chatterjee et al. | 435/6 |
| 6,001,645 | 12/1999 | Slater et al. | 435/320.1 |
| 6,015,668 | 1/2000 | Hughes et al. | 435/6 |
| 6,077,664 | 6/2000 | Slater et al. | 435/6 |

FOREIGN PATENT DOCUMENTS

| | | | |
|---|---|---|---|
| 38 34 636 A1 | 4/1990 | (DE) | C12Q/1/68 |
| 0 329 822 A2 | 8/1989 | (EP) | C12Q/1/68 |
| 0 534 858 A1 | 3/1993 | (EP) | C12Q/1/68 |
| 0 684 315 A1 | 11/1995 | (EP) | C12Q/1/68 |
| 0 892 058 A2 | 1/1999 | (EP) | C12N/15/54 |
| WO 93/06239 | 4/1993 | (WO) | C12Q/1/68 |
| WO 95/13369 | 5/1995 | (WO) | C12Q/1/68 |
| WO 96/10640 | 4/1996 | (WO) | C12N/15/54 |
| WO 96/27680 | 9/1996 | (WO) | C12Q/1/68 |
| 96/41014 | * 12/1996 | (WO) | C12Q/1/68 |
| WO 97/09451 | 3/1997 | (WO) | C12Q/1/68 |
| WO 97/37042 | 10/1997 | (WO) | C12Q/1/68 |
| WO 98/23733 | 6/1998 | (WO) | C12N/9/12 |

OTHER PUBLICATIONS

Suzuki, M., et al., "Random mutagenesis of *Thermus aquaticus* DNA polymerase I: Concordance of immutable sites in vivo with the crystal structure," *Proc. Natl. Acad. Sci. USA* 93:9670–9675 (Sep. 1996).
Suzuki, M., et al., "Low Fidelity Mutants in the O–Helix of *Thermus aquaticus* DNA Polymerase I," *J. Biol. Chem.* 272:11228–11235 (Apr. 25, 1997).
Hite, J.M., et al., "Factors affecting fidelity of DNA synthesis during PCR amplification of $d(C-A)_n-d(G-T)_n$ microsatellite repeats," *Nucl. Acids Res.* 24:2429–2434 (Jun. 1996).
Adams, M.D., et al., "Sequence identification of 2,375 human brain genes," *Nature* 355:632–634 (1992).
Botstein, D., et al., "Construction of a Genetic Linkage Map in Man Using Restriction Fragment Length Polymorphisms," *Am. J. Human Genetics* 32:314–331 (1980).
Caetano–Anollés, G., et al., "DNA Amplification Fingerprinting Using Very Short Arbitrary Oliginucleotide Primers," *Bio/Tech.* 9:553–557 (1991).
Cochran, B.H. et al., "Expression of the c–fos Gene and of an fos–Related Gene Is Stimulated by Platelet–Derived Growth Factor," *Science* 226:1080–1082 (1984).
Gubler, U., and Hoffman, B.J., "A simple and very efficient method for generating cDNA libraries," *Gene* 25:263–269 (1983).
Heath, D.D., et al., "PCR primed with VNTR core sequences yields species specific patterns and hypervariable probes," *Nucl. Acids. Res.* 21:5782–5785 (1993).

(List continued on next page.)

*Primary Examiner*—W. Gary Jones
*Assistant Examiner*—Joyce Tung
(74) *Attorney, Agent, or Firm*—Sterne, Kessler, Goldstein & Fox, P.L.L.C.

(57) ABSTRACT

The present invention provides methods for use in identifying, analyzing and typing polymorphic DNA fragments, particularly minisatellite, microsatellite or STR DNA fragments. In particular, the invention provides methods using DNA polymerases, more particularly thermostable DNA polymerases, and most particularly Thermotoga polymerases or mutants or derivatives thereof, whereby minisatellite, microsatellite or STR DNA molecules maybe amplified and analyzed for polymorphisms. The invention also relates to polymerases having reduced, substantially reduced or eliminated ability to add non-template 3' nucleotides to a synthesized nucleic acid molecule. In accordance with the invention, such reduction or elimination may be accomplished by modifying or mutating the desired polymerase.

9 Claims, 20 Drawing Sheets

OTHER PUBLICATIONS

Hedrick, S.M. et al., "Isolation of cDNA clones encoding T cell–specific membrane–associated proteins," *Nature* 308:149–153 (1984).

HolmstrøK., et al., "A Highly Sensitive and Fast Nonradioactive Method for Detection of Polymerase Chain Reaction Products," *Anal. Biochem.* 209:278–283 (1993).

Ivanova, N.B., and Belyavsky, A.V., "Identification of differentially expressed genes by restriction endonuclease––based gene expression fingerprinting," *Nucl. Acids Res.* 23(15):2954–2958 (Aug. 1995).

Klausner, A., and Wilson, T., "Gene Detection Technology Open Doors for Many Industries," *Bio/Tech.*, p. 471–478 (Aug. 1983).

Lau, L.F., and Nathans, D., "Identification of a set of genes expressed during the G0/G1 transition of cultured mouse cells," *EMBO J.* 4:3145–3151 (1985).

Lee, C.C., et al., "Generation of cDNA Probes Directed by Amino Acid Sequence: Cloning of Urate Oxidase," *Science* 239:1288–1291 (1988).

Lin, J.–J., et al., "DH12S: A New Electrocompetent *E. coli* Strain for the Production of Highly Purified Single–Stranded DNA Using Phagemid Vectors," *Focus* 14:98–101 (1992).

Lin, J.–J., and Kuo, J., "AFLP™:A Novel PCR–Based Assay for Plant and Bacterial DNA Fingerprinting," *Focus* 17:66–70 (Jun. 1995).

Lin, J.–J., et al., "Identification of Molecular Markers in Soybean Comparing RFLP, RAPD and AFLP DNA Mapping Techniques," *Plant Mol. Biol. Reporter* 14:156–169 (Jun. 1996).

Lin, J.–J., et al., "Effect of Different Primer Combinations on the Resolution of AFLP™ in Plants with Small Genomes," *Focus* 18:68–69 (Nov. 1996).

Lin, J.–J., et al., "Chemiluminescent Detection of AFLP™ Fingerprints," *Focus* 19:36–38 (Jul. 1997).

Maniatis, T., et al., "The Isolation of Structural Genes from Libraries of Eucaryotic DNA," *Cell* 15:687–701 (1978).

Okayama, H., and Berg, P., "High–Efficiency Cloning of Full–length cDNA," *Mol. Cell. Biol.* 2:161–170 (1982).

Tanksley, S.D., et al., "RFLP Mapping in Plant Breeding: New Tools for an Old Science," *Bio/Tech.* 7:257–264 (1989).

Vos, P., et al., "AFLP: a new technique for DNA fingerprinting," *Nucl. Acids. Res.* 23:4407–4414 (Nov. 1995).

Welsh, J., and McClelland, M., "Fingerprinting genomes using PCR with arbitrary primers," *Nucl. Acids. Res.* 18:7213–7218 (1990).

Wilks, A.F., "Two putative protein–tyrosine kinases identified by application of the polymerase chain reaction," *Proc. Natl. Acad. Sci. USA* 86:1603–1607 (1989).

Williams, J.G.K., et al., "DNA polymorphisms amplified by arbitrary primers are useful as genetic markers," *Nucl. Acids Res.* 18:6531–6535 (1990).

Yunis, I., et al., "HLA–DR generic typing by AFLP," *Tissue Antigens* 38:78–88 (1991).

* cited by examiner

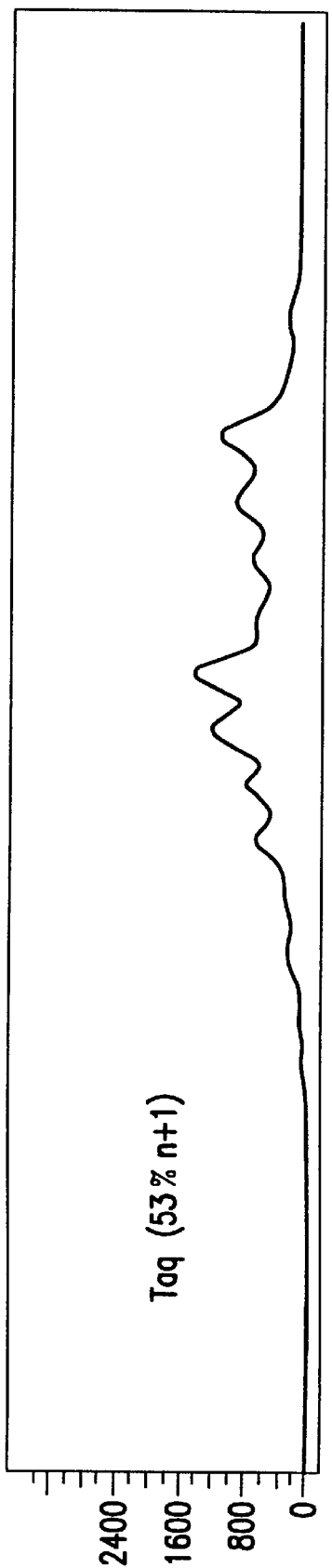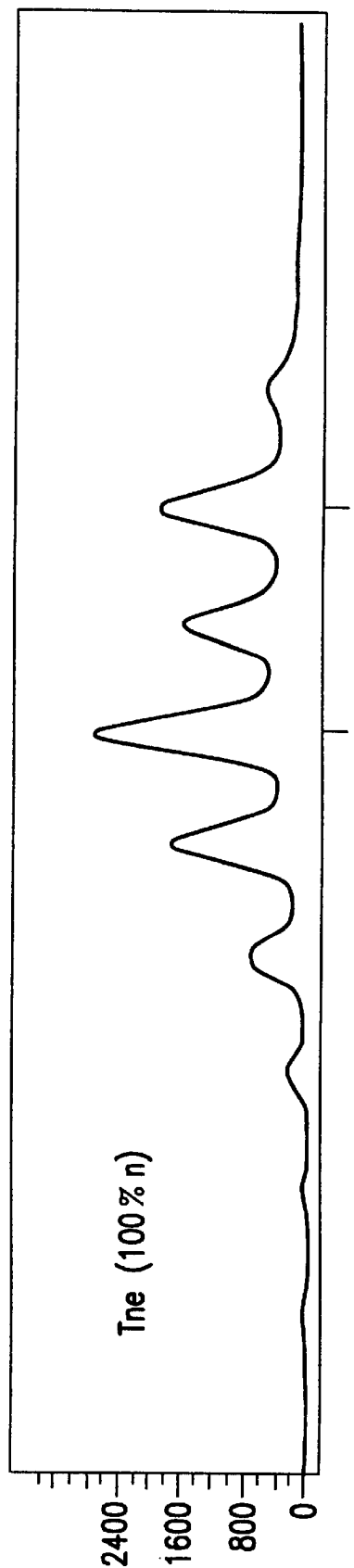
FIG.9C Taq (53% n+1)
FIG.9D Tne (100% n) LOWER ALLELE UPPER ALLELE

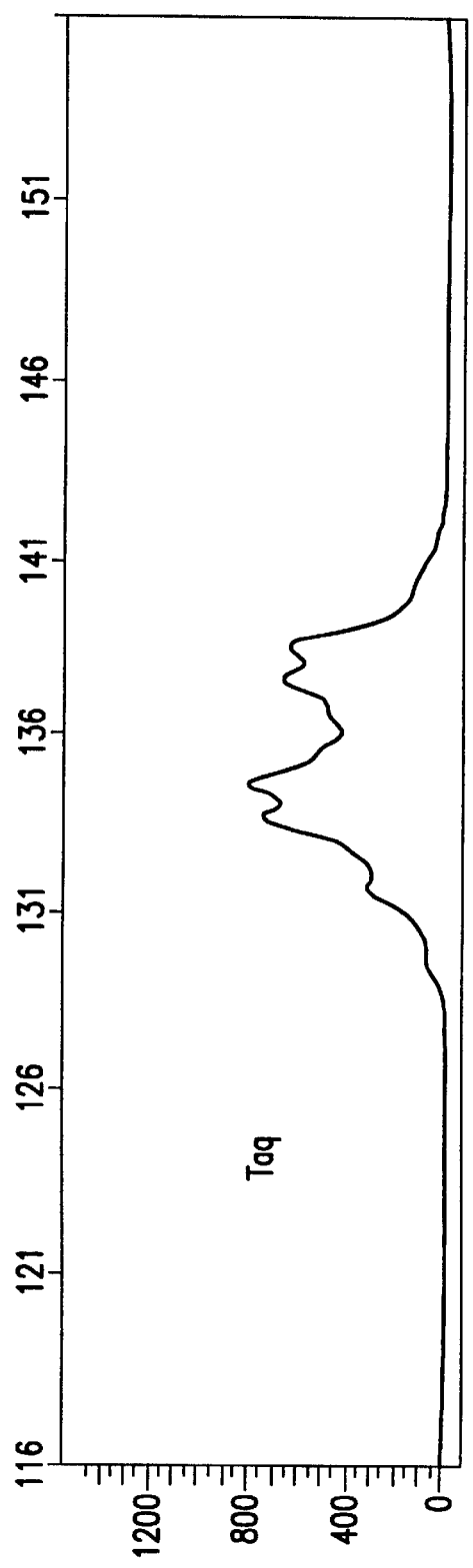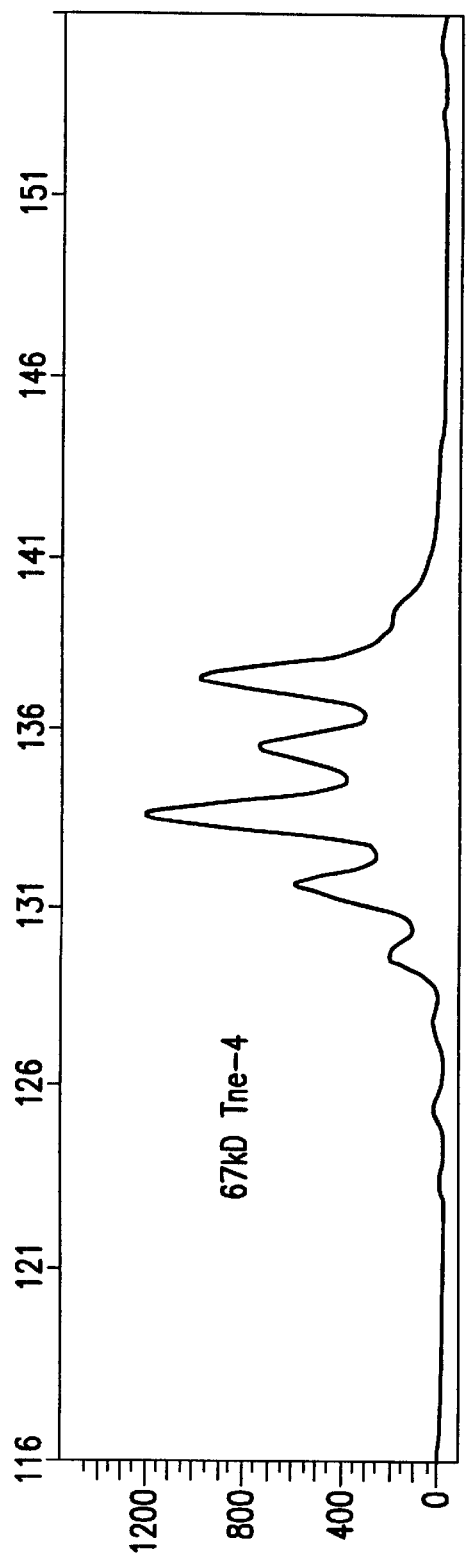

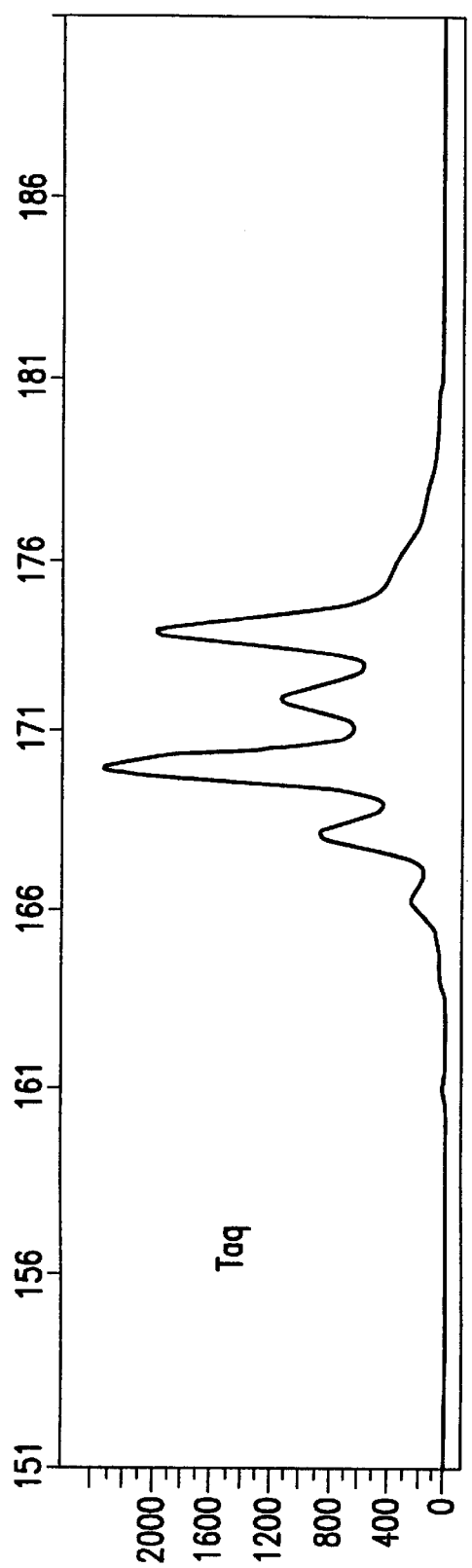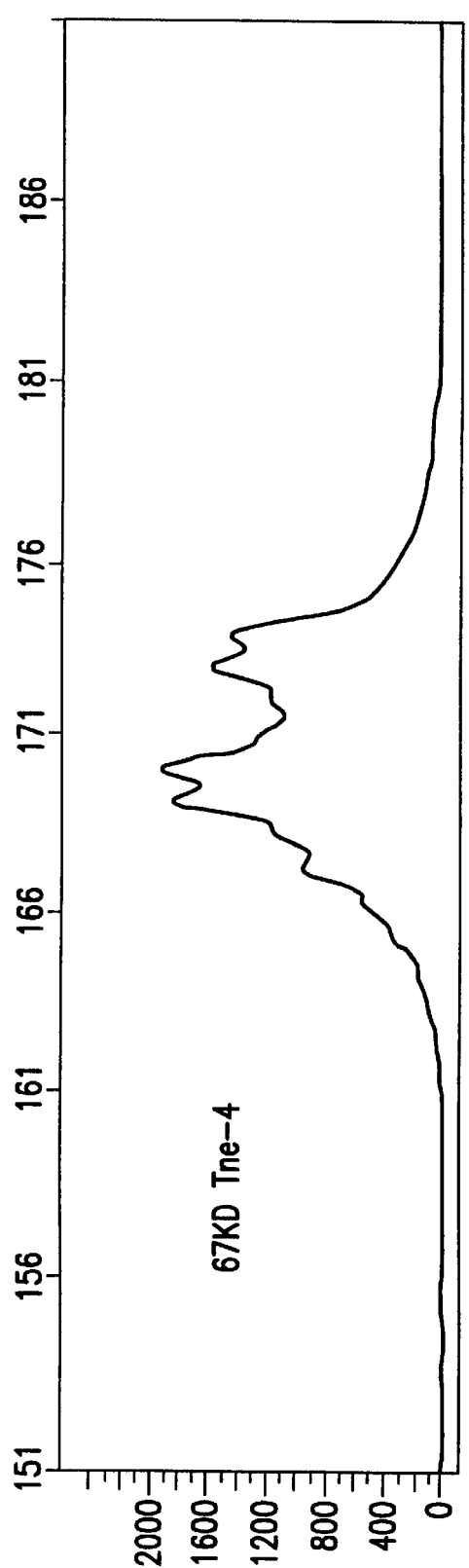

POLYMERASES FOR ANALYZING OR TYPING POLYMORPHIC NUCLEIC ACID FRAGMENTS AND USES THEREOF

CROSS REFERENCE TO RELATED APPLICATIONS

This application claims priority to U.S. Provisional Application No. 60/037,393, filed Feb. 7, 1997, and to the U.S. Provisional Application No. 60/070,562 of Deb K. Chatterjee, Joseph Solus and Shuwei Yang, entitled "Polymerases for Analyzing or Typing Polymorphic Nucleic Acid Fragments and Uses Thereof," filed Jan. 6, 1998, the disclosures of which are fully incorporated herein by reference.

FIELD OF THE INVENTION

The present invention is in the field of molecular and cellular biology. The invention relates to compositions and methods for use in analyzing and typing polymorphic regions of DNA. More particularly, the invention is directed to compositions of polymerases (preferably DNA polymerases and most preferably thermostable DNA polymerases), and methods using these compositions, whereby polymorphic, minisatellite, microsatellite or STR DNA fragments maybe amplified and analyzed. The compositions and methods of the present invention are useful in a variety of techniques employing DNA amplification and polymorphism analysis, including medical genetic, forensic, and plant breeding applications.

The present invention also relates to polymerases having reduced, substantially reduced or eliminated ability to add one or more non-templated nucleotides to the 3' terminus of a synthesized nucleic acid molecule. Preferably, the polymerases of the invention are thermostable or mesophilic polymerases. Specifically, the polymerases of the present invention (e.g., DNA or RNA polymerases) have been mutated or modified to reduce, substantially reduce or eliminate such activity (compared to the unmodified, unmutated, or wild type polymerase), thereby providing a polymerase which synthesizes nucleic acid molecules having little or no non-templated 3' terminal nucleotides. Such polymerases thus have enhanced or greater ability to produce a double stranded nucleic acid molecule having blunt ended termini which may facilitate cloning of such molecules. The present invention also relates to cloning and expression of the polymerases of the invention, to nucleic acid molecules containing the cloned genes, and to host cells which express said genes. The polymerases of the present invention may be used in DNA sequencing, amplification, nucleic acid synthesis, and polymorphism analysis.

The invention also relates to polymerases of the invention which have one or more additional mutations or modifications. Such mutations or modifications include those which (1) substantially reduce 3'→5' exonuclease activity; and/or (2) substantially reduce 5'→3' exonuclease activity. The polymerases of the invention can have one or more of these properties. These polymerases may also be used in nucleic acid analysis including but not limited to DNA sequencing, amplification, nucleic acid synthesis, and polymorphism analysis.

BACKGROUND OF THE INVENTION

DNA Structure

The genetic framework (i.e., the genome) of an organism is encoded in the double-stranded sequence of nucleotide bases in the deoxyribonucleic acid (DNA) which is contained in the somatic and germ cells of the organism. The genetic content of a particular segment of DNA, or gene, is only manifested upon production of the protein which the gene ultimately encodes. There are additional sequences in the genome that do not encode a protein (i.e., "noncoding" regions) which may serve a structural, regulatory, or unknown function. Thus, the genome of an organism or cell is the complete collection of protein-encoding genes together with intervening noncoding DNA sequences. Importantly, each somatic cell of a multicellular organism contains the full complement of genomic DNA of the organism, except in cases of focal infections or cancers, where one or more xenogeneic DNA sequences may be inserted into the genomic DNA of specific cells and not into other, non-infected, cells in the organism.

Minisatellite and Microsatellite DNA

Interspersed throughout the genomic DNA of most eukaryotic organisms are short stretches of polymorphic repetitive nucleotide sequences known as "minisatellite DNA" sequences or fragments (Jeffreys, A. J., et al, Nature 314:67–73 (1985)). These repeating sequences often appear in tandem and in variable numbers within the genome, and they are thus sometimes referred to as "short tandem repeats" ("STRs") or "variable numbers of tandem repeats" ("VNTRs") (see U.S. Pat. No. 5,075,217; Nakamura et al., Science 235:1616–1622 (1987)). Typically, however, minisatellite repeat units are about 9 to 60 bases in length (Nakamura et al., Science 235:1616–1622 (1987); Weber and May, Am. J. Hum. Genet. 44:388–396 (1989)) which are repeated in tandem about 20–50 times (Watson, J. D., et al., eds., Recombinant DNA, 2nd ed., New York: Scientific American Books, p. 146 (1992)). Other short, simple sequences which are analogous to minisatellite DNAs, termed "microsatellite DNAs" (Litt, M., and Luty, J. A., Am. J. Hum. Genet 44:397–401 (1989); Weber and May, Am. J. Hum. Genet. 44:388–396 (1989)), are usually about 1–6 bases in repeat unit length and thus give rise to monomeric (Economou, E. T., et al, Proc. Natl. Acad Sci. USA 87:2951–2954 (1990)), dimeric, trimeric, quatrameric, pentameric or hexameric repeat units (Litt, M., and Luty, J. A., Am. J. Hum. Genet 44:397–401 (1989); Weber and May, Am. J. Hum. Genet. 44:388–396 (1989)). The most prevalent of these highly polymorphic microsatellite sequences in the human genome is the dinucleotide repeat $(dC-dA)_n \cdot (dG-dT)_n$ (where n is the number of repetitions in a given stretch of nucleotides), which is present in a copy number of about 50,000–100,000 (Tautz, D., and Renz, M., Nucl. Acids Res. 12:4127–4138(1984); Dib, C., et al., Nature 360:152–154 (1996)), although the existence of a variety of analogous repeat sequences in the genomes of evolutionarily diverse eukaryotes has been reported (Hamada, H., et al., Proc. Natl. Acad Sci. USA 79:6465–6469 (1982)).

The actual in vivo function of minisatellite and microsatellite sequences is unknown. However, because these tandemly repeated sequences are dispersed throughout the genome of most eukaryotes, exhibit size polymorphism, and are often heterozygous (Weber, J. L., Genomics 7:524–530 (1990)), they have been explored as potential genetic markers in assays attempting to distinguish closely related individuals, and in forensic and paternity testing (see, e.g., U.S. Pat. No. 5,075,217; Jeffreys, A. J., et al., Nature 332:278–281 (1988)). The finding that mutations often are observed in microsatellite DNA regions in cancer cells (Loeb, L. A., Cancer Res. 54:5059–5063 (1994)), potentially linking genomic instability to the carcinogenic process and providing useful genetic markers of cancer, lends additional significance to methods facilitating the rapid analysis and genotyping of polymorphisms in these genomic DNA regions.

Methods of Genotyping Minisatellite or STR DNA Sequences

To analyze minisatellite, microsatellite or STR DNA sequence polymorphisms, a variety of molecular biological techniques have been employed. These techniques include restriction fragment length polymorphism (RFLP) or "DNA fingerprinting" analysis (Wong, Z., et al., *Nucl. Acids Res.* 14:4605–4616 (1986); Wong, Z., et al., *Ann. Hum. Genet* 51:269–288 (1987); Jeffreys, A. J., et al., *Nature* 332:278–281 (1988); U.S. Pat. Nos. 5,175,082; 5,413,908; 5,459,039; and 5,556,955). Far more commonly employed for STR genotyping than RFLP and hybridization, however, are amplification-based methods, such as those relying on the polymerase chain reaction (PCR) method invented by Mullis and colleagues (see U.S. Pat. Nos. 4,683,195; 4,683,202; and 4,800,159). These methods use "primer" sequences which are complementary to opposing regions flanking the polymorphic DNA sequence to be amplified from the sample of genomic DNA to be analyzed. These primers are added to the DNA target sample, along with excess deoxynucleotides and a DNA polymerase (e.g., Taq polymerase; see below), and the primers bind to their target via base-specific binding interactions (i.e., adenine binds to thymine, cytosine to guanine). By repeatedly passing the reaction mixture through cycles of increasing and decreasing temperatures (to allow dissociation of the two DNA strands on the target sequence, synthesis of complementary copies of each strand by the polymerase, and re-annealing of the new complementary strands), the copy number of the minisatellite or STR sequence of DNA may be rapidly increased, and detected by size separation methods such as gel electrophoresis.

PCR and related amplification approaches have been used in attempts to develop methods for typing and analyzing STRs or minisatellite regions. For example, PCR has been employed to analyze polymorphisms in microsatellite sequences from different individuals, including (dC-dA)n•(dG-dT)n (Weber, J. L., and May, P. E., *Am. J. Hum. Genet.* 44:388–396 (1989); Weber, J. L., *Genomics* 7:524–530 (1990); U.S. Pat. Nos. 5,075,217; 5,369,004; and 5,468,613). Similar methods have been applied to a variety of medical and forensic samples to perform DNA typing and to detect polymorphisms between individual samples (U.S. Pat. Nos. 5,306,616; 5,364,759; 5,378,602; and 5,468,610).

In Vitro Use of DNA Polymerases

The above-described amplification-based techniques require the use of DNA polymerases, which catalyze the addition of deoxynucleoside triphosphate (dNTP) bases into the newly forming DNA strands. Together with other enzymes (e.g., helicases, ligases and ATPases), the DNA polymerases ensure rapid and relatively faithful replication of DNA in preparation for proliferation in vivo in prokaryotes, eukaryotes and viruses.

DNA polymerases synthesize the formation of DNA molecules which are complementary to a DNA template. Upon hybridization of a primer to the single-stranded DNA template, polymerases synthesize DNA in the 5' to 3' direction, successively adding nucleotides to the 3'-hydroxyl group of the growing strand. Thus, in the presence of deoxyribonucleoside triphosphates (dNTPs) and a primer, a new DNA molecule, complementary to the single stranded DNA template, can be synthesized.

In addition to an activity which adds dNTPs to DNA in the 5' to 3' direction (i.e., "polymerase" activity), many DNA polymerases also possess activities which remove dNTPs in the 5' to 3' and/or the 3' to 5' direction (i.e., "exonuclease" activity). This dual activity of certain DNA polymerases is, however, a drawback for some in vitro applications. For example, the in vitro synthesis of an intact copy of a DNA fragment by the polymerase activity, an elongation process which proceeds in a 5' to 3' direction along the template DNA strand, is jeopardized by the exonuclease activities which may simultaneously or subsequently degrade the newly formed DNA.

Limitations of PCR-based Genotyping of Minisateilite, Microsatellite and STR DNA Sequences Application of PCR-based methods to analysis of minisatellite or STR DNA sequences has a number of significant limitations. It has been shown, for example, that use of Taq and other thermostable DNA polymerases commonly employed in PCR and related automated amplification methods causes the accumulation of amplification products containing non-templated 3' terminal nucleotides (Clark, J. M., et al., *J. Molec. Biol.* 198:123–127 (1987); Clark, J. M., *Nucl. Acids Res.* 16:9677–9686 (1988); Hu, G., *DNA Cell Biol.* 12:763–770 (1993)). That is, some of the newly synthesized DNA strands produced in each round of amplification have had an extra nucleotide added to their 3' termini, such that the newly synthesized strands may be longer by one base.

Non-templated nucleotide addition is a slow process compared to template-directed synthesis (Clark, J. M., *Nucl. Acids Res.* 16:9677–9686 (1988)), and its extent is sequence-dependent (Hu, G., *DNA Cell Biol.* 12:763–770 (1993); Brownstein, M. J., et al., *BioTechniques* 20:1004–1010 (1996)). Consequently, the PCR product is often heterogeneous in regard to extra nucleotide addition depending upon the primers and the reaction conditions used by the investigator (Magnuson, V. L., et al., *BioTechniques* 21:700–709 (1996)). Extra nucleotide addition, in combination with "stutter" due to slippage during PCR amplification (Levinson, G., and Gutman, G. A., *Molec. Biol. Evol.* 4:203–221 (1987); Schlotterer, C., and Tautz, D., *Nucl. Acids Res.* 20:211–215 (1992)), often results in complex DNA fragment patterns which are difficult to interpret, especially by automated methods. This can result in improper genotyping analysis, particularly if the percentage of non-templated nucleotide addition is between 30–70% of the PCR product (Smith, J. R., et al., *Genome Res.* 5:312–317 (1995)).

Thus, a need currently exists for a rapid, automated method for identifying, analyzing and typing polymorphic DNA fragments, particularly minisatellite, microsatellite or STR DNA fragments, that will not result in the problematic results described above. The present invention provides such a method.

BRIEF SUMMARY OF THE INVENTION

The present invention satisfies these needs in the art by providing methods useful in the identification, analysis or typing of polymorphic DNA fragments, particularly minisatellite, microsatellite or STR DNA fragments, in samples of DNA from a cell, particularly a eukaryotic cell. Specifically, the invention provides a method of producing a population of amplified DNA molecules, for use in analyzing or typing a DNA molecule in a DNA sample isolated from a cell, preferably a eukaryotic cell. The method of the present invention comprises contacting a DNA sample with a DNA polymerase (preferably a thermostable DNA polymerases) reduced, substantially reduced or eliminated in the ability to add one or more non-templated nucleotides to the 3' terminus of a DNA molecule, amplifying a polymorphic DNA fragment, preferably a minisatellite, microsatellite or STR DNA fragment, within the DNA sample and analyzing the amplified polymorphic DNA fragment. In the method of the invention, the analysis step may comprise, for example, sizing or sequencing the amplified DNA molecule and optionally comparing the size and/or sequence of the amplified DNA molecule to a different DNA sample which has been amplified according to the invention. In preferred embodiments of the present invention, the thermostable DNA polymerase is a Thermotoga DNA polymerase, preferably a Thermotoga DNA polymerase substantially reduced in 3'–5' exonuclease activity, more preferably a Tne polymerase, a Tma polymerase, or a mutant or derivative thereof, and most preferably a mutant of Tne polymerase selected from the group consisting of Tne N'Δ219, D323A; Tne N'Δ283, D323A; Tne N'Δ284, D323A; Tne N'Δ193, D323A; TneD137A, D323A; TneD8A, D323A; Tne G195D, D323A; Tne G37D, D323A; Tne N'Δ283; Tne D137A, D323A, R722K; Tne D137A, D323A, R722Y; Tne D137A, D323A, R722L; Tne D137A, D323A, R722H; Tne D137A, D323A, R722Q; Tne D137A, D323A, F730Y; Tne D137A, D323A, K726R; Tne D137A, D323A, K726H; Tne D137A, D323A, R722K, F730Y; Tne D137A, D323A, R722K, K726R; Tne D137A, D323A, R722K, K726H; Tne D137A, D323A, R722H, F730Y; Tne D137A, D323A, R722H, K726R; Tne D137A, D323A, R722H, K726H; Tne D137A, D323A, R722Q, F730Y; Tne D137A, D323A, R722Q, K726R; Tne D137A, D323A, R722Q, K726H; Tne D137A, D323A, R722N, F730Y; Tne D137A, D323A, R722N, K726R; Tne D137A, D323A, R722N, K726H; Tne D137A, D323A, F730S; Tne N'Δ283, D323A, R722K/H/Q/N/Y/L; Tne N'Δ219, D323A, R722K; Tne N'Δ219, D323A, F730Y; Tne N'Δ219, D323A, K726R; Tne N'Δ219, D323A, K726H; Tne D137A, D323A, F730S, R722K/Y/Q/N/H/L, K726R/H; Tne D137A, D323A, F730T, R722K/Y/Q/N/H/L, K726R/H; Tne D137A, D323A, F730T; Tne F730S; Tne F730A; Tne K726R; Tne K726H; and Tne D137A, D323A, R722N. The present invention is particularly directed to the above methods wherein the eukaryotic cell is an plant cell or an animal cell, preferably a mammalian cell, more preferably a normal, diseased, cancerous, fetal or embryonic mammalian cell, and most preferably a human cell. The invention is also directed to the above methods, further comprising isolating the polymorphic, minisatellite, microsatellite or STR DNA fragment and inserting it into a vector, preferably an expression vector. By the present methods, the polymorphic or microsatellite DNA fragment may be amplified prior to being inserted into the vector.

The present invention also provides a method of determining the relationship between a first individual and a second individual, comprising contacting a DNA sample from the first and second individuals with a DNA polymerase (e.g. a thermostable DNA polymerase) reduced, substantially reduced or eliminated in the ability to add one or more non-templated nucleotides to the 3' terminus of a DNA molecule, amplifying one or more DNA molecules in the DNA sample to generate a collection of amplified polymorphic DNA fragments, separating the amplified DNA fragments by length, and comparing the pattern of amplified DNA fragments from the first individual to that of the second individual. This method also allows the identification of one or more unique polymorphic DNA fragments, particularly a minisatellite, microsatellite or STR DNA fragment, that is specifically present in only one of the two individuals. This method may further comprise determining the sequence of the unique polymorphic, minisatellite, microsatellite or STR DNA fragment. In this embodiment of the present invention, the thermostable DNA polymerase may be a Thermotoga DNA polymerase, preferably a Thermotoga DNA polymerase substantially reduced in 3'–5' exonuclease activity, more preferably a Tne polymerase, a Tma polymerase, or a mutant or derivative thereof, and most preferably a mutant of Tne polymerase selected from the group consisting of Tne N'Δ219, D323A; Tne N'Δ283, D323A; Tne N'Δ284, D323A; Tne N'Δ193, D323A; Tne D137A, D323A; Tne D8A, D323A; Tne G195D, D323A; Tne G37D, D323A; Tne N'Δ283; Tne D137A, D323A, R722K; Tne D137A, D323A, R722Y; Tne D137A, D323A, R722L; Tne D137A, D323A, R722H; Tne D137A, D323A, R722Q; Tne D137A, D323A, F730Y; Tne D137A, D323A, K726R; Tne D137A, D323A, K726H; Tne D137A, D323A, R722K, F730Y; Tne D137A, D323A, R722K, K726R; Tne D137A, D323A, R722K, K726H; Tne D137A, D323A, R722H, F730Y; Tne D137A, D323A, R722H, K726R; Tne D137A, D323A, R722H, K726H; Tne D137A, D323A, R722Q, F730Y; Tne D137A, D323A, R722Q, K726R; Tne D137A, D323A, R722Q, K726H; Tne D137A, D323A, R722N, F730Y; Tne D137A, D323A, R722N, K726R; Tne D137A, D323A, R722N, K726H; Tne D137A, D323A, F730S; Tne N'Δ283, D323A, R722K/H/Q/N/Y/L; Tne N'Δ219, D323A, R722K; Tne N'Δ219, D323A, F730Y; Tne N'Δ219, D323A, K726R; Tne N'Δ219, D323A, K726H; Tne D137A, D323A, F730S, R722K/Y/Q/N/H/L, K726R/H; Tne D137A, D323A, F730T, R722K/Y/Q/N/H/L, K726R/H; Tne D137A, D323A, F730T; Tne F730S; Tne F730A; Tne K726R; Tne K726H; and Tne D137A, D323A, R722N. The present invention is particularly directed to the above methods wherein the first or second individual is an animal or a plant, and most preferably wherein the first or second individual is a human.

The present invention also provides isolated nucleic acid molecules encoding mutant Tne DNA polymerase proteins, wherein the mutant Tne DNA polymerase proteins have an amino acid sequence as set forth in any one of SEQ ID NOs: 4–10. The invention also provides mutant Tne DNA polymerase proteins having an amino acid sequence as set forth in any one of SEQ ID NOs:4–10, most preferably a mutant Tne polymerase protein selected from the group consisting of Tne N'Δ283, D323A (SEQ ID NO:4); Tne N'Δ193, D323A (SEQ ID NO:5); Tne D137A, D323A (SEQ ID NO:6); Tne D8A, D323A (SEQ ID NO:7); Tne G195D, D323A (SEQ ID NO:8); Tne G37D, D323A (SEQ ID NO:9); and Tne N'Δ283 (SEQ ID NO:10). The invention also relates to nucleic acid molecules and the proteins encoded by such nucleic acid molecules for mutant Tne polymerases selected from the group consisting of Tne n'Δ283; Tne D137A, D323A, R722K; Tne D137A, D323A, R722Y; Tne D137A, D323A, R722L; Tne D137A, D323A, R722H; Tne D137A, D323A, R722Q; Tne D137A, D323A, F730Y; Tne D137A, D323A, K726R; Tne D137A, D323A, K726H; Tne D137A, D323A, R722K, F730Y; Tne D137A, D323A, R722K, K726R; Tne D137A, D323A, R722K, K726H; Tne D137A, D323A, R722H, F730Y; Tne D137A, D323A, R722H, K726R; Tne D137A, D323A, R722H, K726H; Tne D137A, D323A, R722Q, F730Y; Tne D137A, D323A, R722Q, K726R; Tne D137A, D323A, R722Q, K726H; Tne D137A, D323A, R722N, F730Y; Tne D137A, D323A, R722N, K726R; Tne D137A, D323A, R722N, K726H; Tne D137A, D323A, F730S; Tne N'Δ283, D323A, R722K/H/Q/N/Y/L; Tne N'Δ219, D323A, R722K; Tne N'Δ219, D323A, F730Y; Tne N'Δ219, D323A, K726R; Tne N'Δ219, D323A, K726H; Tne D137A, D323A, F730S, R722K/Y/Q/N/H/L, K726H; Tne D137A, D323A, F730T, R722K/Y/Q/N/H/L, K726H; Tne D137A, D323A, F730T; Tne F730S; Tne F730A; Tne K726R; Tne K726H; and Tne D137A, D323A, R722N. These mutations may be made to sequence ID NO:2 to produce the mutant polymerases having the indicated amino acid mutations (where, for example, "D137A" indicates that the Asp (D) residue at position 137 in SEQ ID NO:2 has been mutated to an Ala (A) residue, and, for example, "R722K/Y/Q/N/H/L" indicates that the Arg (R) residue at position 722 in SEQ ID NO:2 has been mutated to a Lys (K), Tyr (Y), Gln (Q), Asn (N), His (H) or Leu (L) residue).

The present invention also provides kits for the identification, analysis or typing of a polymorphic DNA fragment, particularly a minisatellite, microsatellite or STR DNA fragment, comprising a first container containing one or more DNA polymerases reduced, substantially reduced or eliminated in the ability to add non-templated 3' terminal nucleotides. Kits according to the invention may contain additional containers selected from the group consisting of a container containing one or more DNA primer molecules, a container containing one or more deoxynucleoside triphosphates needed to synthesize a DNA molecule complementary to the DNA template, and a container containing a buffer suitable for identifying, analyzing or typing a polymorphic DNA fragment by the methods of the invention. Any number of these components of the kit may be combined in a single or multiple containers to provide the kit of the invention. According to the invention, the DNA polymerase of the kit is preferably a Thermotoga DNA polymerase, more preferably a Thermotoga DNA polymerase substantially reduced in 3'–5' exonuclease activity, still more preferably a Tne polymerase, a Tma polymerase, or a mutant or derivative thereof, and most preferably a mutant of Tne polymerase selected from the group consisting of Tne N'Δ283; Tne D137A, D323A, R722K; Tne D137A, D323A, R722Y; Tne D137A, D323A, R722L; Tne D137A, D323A, R722H; Tne D137A, D323A, R722Q; Tne D137A, D323A, F730Y; Tne D137A, D323A, K726R; Tne D137A, D323A, K726H; Tne D137A, D323A, R722K, F730Y; Tne D137A, D323A, R722K, K726R; Tne D137A, D323A, R722K, K726H; Tne D137A, D323A, R722H, F730Y; Tne D137A, D323A, R722H, K726R; Tne D137A, D323A, R722H, K726H; Tne D137A, D323A, R722Q, F730Y; Tne D137A, D323A, R722Q, K726R; Tne D137A, D323A, R722Q, K726H; Tne D137A, D323A, R722N, F730Y; Tne D137A, D323A, R722N, K726R; Tne D137A, D323A, R722N, K726H; Tne D137A, D323A, F730S; Tne N'Δ283, D323A, R722K/H/Q/N/Y/L; Tne N'Δ219, D323A, R722K; Tne N'Δ219, D323A, F730Y; Tne N'Δ219, D323A, K726R; Tne N'Δ219, D323A, K726H; Tne D137A, D323A, F730S, R722K/Y/Q/N/H/L, K726R/H; Tne D137A, D323A, F730T, R722K/Y/Q/N/H/L, K726R/H; Tne D137A, D323A, F730T; Tne F730S; Tne F730A; Tne K726R; Tne K726H; and Tne D137A, D323A, R722N.

The present invention also relates generally to mutated or modified polymerases (DNA or RNA polymerases) which have reduced, substantially reduced or eliminated ability to add one or more non-templated nucleotides to the 3' terminus of a synthesized nucleic acid molecule (compared to the corresponding wildtype, unmutated or unmodified polymerase). Preferably, such mutant or modified polymerases have substantially reduced ability to add one or more non-templated nucleotides to the 3' terminus of a synthesized nucleic acid molecule. Such polymerases of the invention may be thermostable or mesophilic polymerases. Thus, the present invention relates to such mutated or modified polymerases and to kits containing such polymerases. The invention also relates to the use of such mutant or modified polymerases in a number of procedures including DNA sequencing, amplification reactions, nucleic acid synthesis, and polymorphism analysis.

Mutant or modified polymerases of particular interest in the invention include Taq DNA polymerase, Tne DNA polymerase, Tma DNA polymerase, Pfu DNA polymerase, Tfl DNA polymerase, Tth DNA polymerase, Tbr DNA polymerase, Pwo DNA polymerase, Bst DNA polymerase, Bca DNA polymerase, VENT™ DNA polymerase, DEEP VENT™ DNA polymerase, T7 DNA polymerase, T5 DNA polymerase, DNA polymerase III, Klenow fragment DNA polymerase, Stoffel fragment DNA polymerase, and mutants, fragments or derivatives thereof RNA polymerases of interest include T7, SP6, and T3 RNA polymerases and mutants, variants and derivatives thereof.

The present invention relates in particular to mutant PolI type DNA polymerases (preferably thermostable DNA polymerases) wherein one or more mutations have been made in the O-helix which reduces, substantially reduces or eliminates the ability of the enzyme to add one or more non-templated nucleotides to the 3' terminus of a synthesized nucleic acid molecule. The O-helix is defined as RXXXKXXXFXXXYX (SEQ ID NO:11), wherein X may be any amino acid. The preferred sites for mutation or modification to produce the polymerases of the invention are the R and/or F and/or K and/or Y positions in the O-helix, although other changes (or combinations thereof) within the O-helix may be made to make the desired polymerase. In this preferred aspect of the invention, R and/or F and/or K and/or Y may be replaced with any other amino acid including Ala, Arg, Asn, Asp, Cys, Gln, Glu, Gly, His, Ile, Leu, Lys, Met, Phe, Pro, Ser, Thr, Trp, Tyr and Val.

In accordance with the invention, other functional changes (or combinations thereof) may be made to the polymerases having reduced ability to add non-templated nucleotides to the 3' terminus of a synthesized nucleic acid molecule. For example, the polymerase may also be modified to reduce, substantially reduce or eliminate 5' exonuclease activity, and/or 3' exonuclease activity. Thus, the invention relates to mutant or modified DNA polymerases having reduced ability to add non-templated nucleotides which are modified in at least one way selected from the group consisting of (a) to reduce or eliminate the 3'–5' exonuclease activity of the polymerase;

(b) to reduce or eliminate the 5'–3' exonuclease activity of the polymerase;

Any one or a number of these mutations or modifications (or combinations thereof) may be made to provide the polymerases of the invention. Preferred polymerases of the invention, in addition to having reduced ability to add non-templated 3' nucleotides, also have reduced, substantially reduced or eliminated 3' exonuclease activity.

The present invention is also directed to nucleic acid molecules (preferably vectors) containing a gene encoding the mutant or modified polymerases of the present invention and to host cells containing such molecules. Any number of hosts may be used to express the gene of interest, including prokaryotic and eukaryotic cells. Preferably, prokaryotic cells are used to express the polymerases of the invention. The preferred prokaryotic host according to the present invention is *E. coli*.

The invention also relates to a method of producing the polymerases of the invention, said method comprising:

(a) culturing the host cell comprising a gene encoding a polymerase of the invention;

(b) expressing said gene; and (c) isolating said polymerase from said host cell.

The invention also relates to a method of synthesizing a nucleic acid molecule comprising:

(a) mixing one or more nucleic acid templates (e.g. RNA or DNA) with one or more polymerases of the invention; and (b) incubating said mixture under conditions sufficient to synthesize nucleic acid molecules complementary to all or a portion of said templates. Such condition may include incubation with one or more deoxy- and/or dideoxyribonucleoside triphosphates. Such deoxy- and dideoxyribonucleoside triphosphates include dATP, dCTP, dGTP, dTTP, dITP, 7-deaza-dGTP, 7-deaza-dATP, dUTP, ddATP, ddCTP, ddGTP, ddITP, ddTTP, [α-S]dATP, [α-S]dTTP, [α-S]dGTP, and [α-S]dCTP. The synthesized nucleic acid molecules may in accordance with the invention be cloned into one or more vectors.

The invention also relates to a method of sequencing a DNA molecule, comprising:

(a) hybridizing a primer to a first DNA molecule;

(b) contacting said molecule of step (a) with deoxyribonucleoside triphosphates, one or more DNA polymerases of the invention, and one or more terminator nucleotides;

(c) incubating the mixture of step (b) under conditions sufficient to synthesize a random population of DNA molecules complementary to said first DNA molecule, wherein said synthesized DNA molecules are shorter in length than said first DNA molecule and wherein said synthesized DNA molecules comprise a terminator nucleotide at their 3' termini; and (d) separating said synthesized DNA molecules by size so that at least a part of the nucleotide sequence of said first DNA molecule can be determined. Such terminator nucleotides include but are not limited to dideoxyribonucleoside triphosphates such as ddTTP, ddATP, ddGTP, ddITP or ddCTP.

The invention also relates to a method for amplifying a double stranded DNA molecule, comprising:

(a) providing a first and second primer, wherein said first primer is complementary to a sequence at or near the 3'-termini of the first strand of said DNA molecule and said second primer is complementary to a sequence at or near the 3'-termini of the second strand of said DNA molecule;

(b) hybridizing said first primer to said first strand and said second primer to said second strand in the presence of one or more polymerases of the invention, under conditions such that a third DNA molecule complementary to said first strand and a fourth DNA molecule complementary to said second strand are synthesized;

(c) denaturing said first and third strands, and said second and fourth strands; and (d) repeating steps (a) to (c) one or more times. The amplified double-stranded nucleic acid molecules produced by the method of the invention may be cloned into one or more vectors. Thus, the invention relates also to a method of cloning an amplified DNA molecule comprising:

(a) amplifying one or more DNA molecules with one or more polymerases of the invention; and (b) ligating said amplified DNA molecules in one or more vectors.

The invention further relates to a method of cloning a nucleic acid molecule comprising:

(a) mixing a nucleic acid template (or one or more templates) with one or more polymerases of the invention;

(b) incubating said mixture under conditions sufficient to synthesize a nucleic acid molecule complementary to all or a portion of said template, thereby producing a double-stranded nucleic acid molecule (preferably a double-stranded DNA molecule); and (c) ligating said double-stranded nucleic acid molecule into one or more vectors.

Preferably, the vectors used for ligating the amplified or synthesized double-stranded nucleic acid molecules have blunt ended termini and may be prepared by digesting a vector with any one or a number of restriction enzymes known in the art which provide blunt end cleavage. Such restriction enzymes include ScaI, SmaI, HpaI, HincII, HaeIII, AluI, and the like.

The invention also relates to kits for sequencing, amplifying, synthesizing or cloning of nucleic acid molecules comprising one or more polymerases of the invention and one or more other components (or combinations thereof) selected from the group consisting of (a) one or more dideoxyribonucleoside triphosphates;

(b) one or more deoxyribonucleoside triphosphates;

(c) one or more primers;

(d) one or more suitable buffers; and (e) one or more ligases.

Other preferred embodiments of the present invention will be apparent to one of ordinary skill in light of the following drawings and description of the invention, and of the claims.

BRIEF DESCRIPTION OF THE FIGURES

FIGS. 10A–D are composites of a electropherogram gel scan of PCR amplifications at D16S405 and D16S401 loci.

DETAILED DESCRIPTION OF THE INVENTION

Definitions

Figure 1:
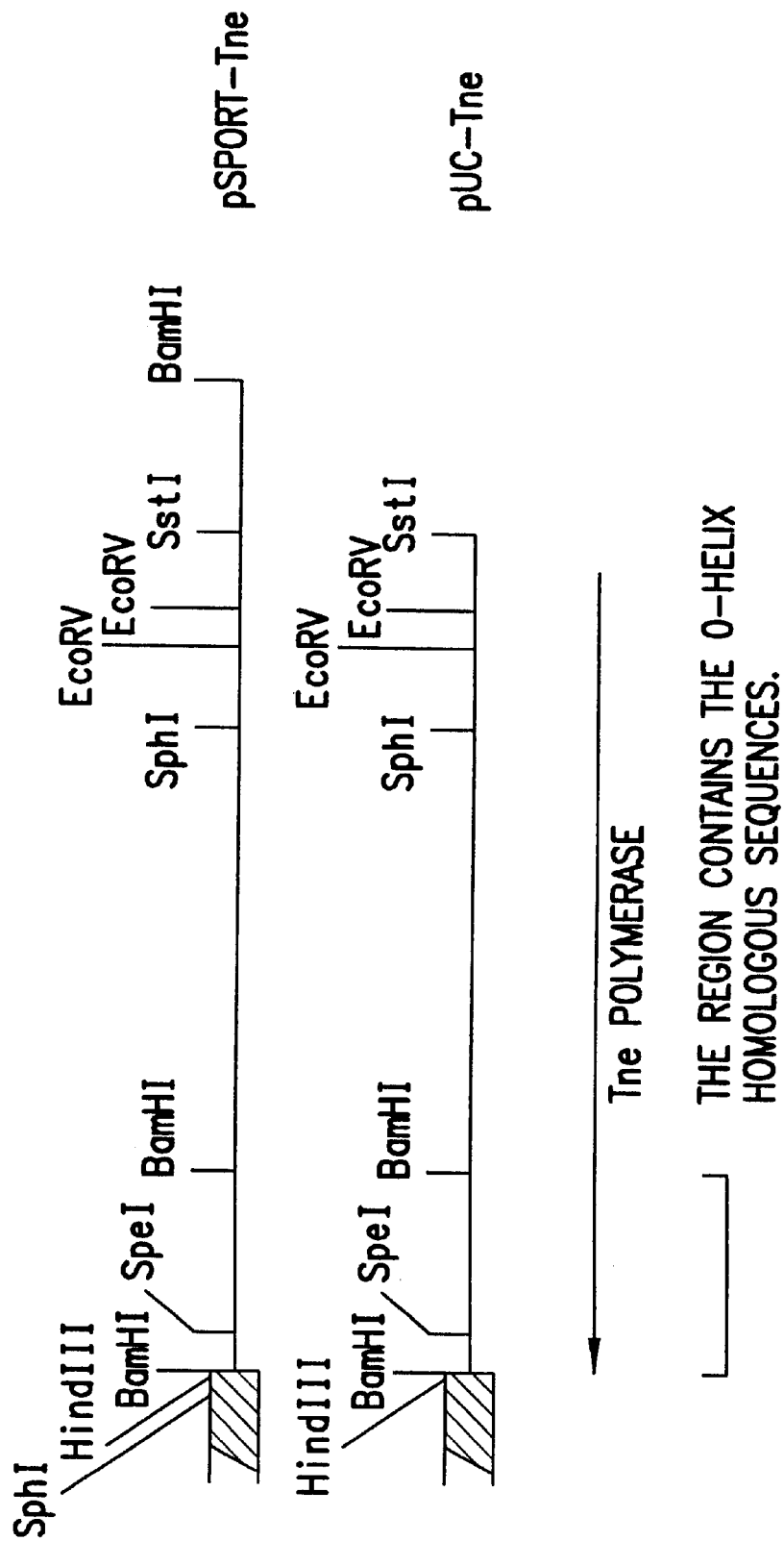
FIG. 1 shows the restriction map of the approximate DNA fragment which contains the Tne DNA polymerase gene in pSport 1 and pUC19. This figure also shows the region containing the O-helix homologous sequences.

In the description that follows, a number of terms used in recombinant DNA technology are extensively utilized. In order to provide a clearer and consistent understanding of the specification and claims, including the scope to be given such terms, the following definitions are provided.

Polymorphic. As is understood by one of ordinary skill in the art, a nucleic acid molecule is said to be "polymorphic" if it may exist in more than one form. For example, a nucleic acid molecule is said to be polymorphic if it may have more than one specific nucleotide sequence (such as degenerate nucleic acid molecules or genes that may each encode the same protein). More commonly, a nucleic acid molecule is said to be polymorphic if it displays size differences (i.e., differences in length), particularly when comparisons of nucleic acid molecules from different individuals are made. Of course, other definitions of the term "polymorphic" will be apparent to one of ordinary skill and are also encompassed within this definition.

Cloning vector. A plasmid, cosmid or phage DNA or other DNA molecule which is able to replicate autonomously in a host cell, and which is characterized by one or a small number of restriction endonuclease recognition sites at which such DNA sequences may be cut in a determinable fashion without loss of an essential biological function of the vector, and into which DNA may be spliced in order to bring about its replication and cloning. The cloning vector may further contain a marker suitable for use in the identification of cells transformed with the cloning vector. Markers, for example, are tetracycline resistance or ampicillin resistance.

Recombinant host. Any prokaryotic or eukaryotic microorganism which contains the desired cloned genes in an expression vector, cloning vector or any DNA molecule. The term "recombinant host" is also meant to include those host cells which have been genetically engineered to contain the desired gene on the host chromosome or genome.

Host. Any prokaryotic or eukaryotic microorganism that is the recipient of a replicable expression vector, cloning vector or any DNA molecule. The DNA molecule may contain, but is not limited to, a structural gene, a promoter and/or an origin of replication.

Promoter. A DNA sequence generally described as the 5' region of a gene, located proximal to the start codon. At the promoter region, transcription of an adjacent gene(s) is initiated.

Gene. A DNA sequence that contains information necessary for expression of a polypeptide or protein. It includes the promoter and the structural gene as well as other sequences involved in expression of the protein.

Structural gene. A DNA sequence that is transcribed into messenger RNA that is then translated into a sequence of amino acids characteristic of a specific polypeptide.

Operably linked. As used herein "operably linked" means that the promoter is positioned to control the initiation of expression of the polypeptide encoded by the structural gene.

Expression. Expression is the process by which a gene produces a polypeptide. It includes transcription of the gene into messenger RNA (mRNA) and the translation of such mRNA into polypeptide(s).

Substantially Pure. As used herein "substantially pure" means that the desired purified protein is essentially free from contaminating cellular contaminants which are associated with the desired protein in nature. Contaminating cellular components may include, but are not limited to, phosphatases, exonucleases, endonucleases or undesirable DNA polymerase enzymes.

Primer. As used herein "primer" refers to a single-stranded oligonucleotide that is extended by covalent bonding of nucleotide monomers during amplification or polymerization of a nucleic acid molecule. Minisatellite primers used for the amplification of minisatelite dimer, trimer, tetramer, etc., sequences are well-known in the art.

Template. The term "template" as used herein refers to a double-stranded or single-stranded nucleic acid molecule which is to be amplified, synthesized or sequenced. In the case of a double-stranded DNA molecule, denaturation of its strands to form a first and a second strand is performed before these molecules may be amplified, synthesized or sequenced. A primer, complementary to a portion of a template is hybridized under appropriate conditions and the polymerase of the invention may then synthesize a molecule complementary to said template or a portion thereof The newly synthesized molecule, according to the invention, may be equal or shorter in length than the original template. Mismatch incorporation or strand slippage during the synthesis or extension of the newly synthesized molecule may result in one or a number of mismatched base pairs. Thus, the synthesized molecule need not be exactly complementary to the template.

Incorporating. The term "incorporating" as used herein means becoming a part of a nucleic acid (e.g., DNA) molecule or primer.

Amplification. As used herein "amplification" refers to any in vitro method for increasing the number of copies of a nucleotide sequence with the use of a DNA polymerase. Nucleic acid amplification results in the incorporation of nucleotides into aDNA molecule or primer thereby forming a new DNA molecule complementary to a DNA template. The formed DNA molecule and its template can be used as templates to synthesize additional DNA molecules. As used herein, one amplification reaction may consist of many rounds of DNA replication. DNA amplification reactions include, for example, polymerase chain reactions (PCR). One PCR reaction may consist of 5 to 100 "cycles" of denaturation and synthesis of a DNA molecule.

Oligonucleotide. "Oligonucleotide" refers to a synthetic or natural molecule comprising a covalently linked sequence of nucleotides which are joined by a phosphodiester bond between the 3' position of the pentose of one nucleotide and the 5' position of the pentose of the adjacent nucleotide.

Nucleotide. As used herein "nucleotide" refers to a base-sugar-phosphate combination. Nucleotides are monomeric units of a nucleic acid sequence (DNA and RNA). The term nucleotide includes deoxyribonucleoside triphosphates such as dATP, dCTP, dITP, dUTP, dGTP, dTTP, or derivatives thereof. Such derivatives include, for example, [αS]dATP, 7-deaza-dGTP and 7-deaza-dATP. The term nucleotide as used herein also refers to dideoxyribonucleoside triphosphates (ddNTPs) and their derivatives. Illustrated examples of dideoxyribonucleoside triphosphates include, but are not limited to, ddATP, ddCTP, ddGTP, ddITP, and ddTTP. According to the present invention, a "nucleotide" may be unlabeled or detectably labeled by well known techniques. Detectable labels include, for example, radioactive isotopes, fluorescent labels, chemiluminescent labels, bioluminescent labels and enzyme labels.

Thermostable. As used herein "thermostable" refers to a polymerase which is resistant to inactivation by heat. DNA polymerases synthesize the formation of a DNA molecule complementary to a single-stranded DNA template by extending a primer in the 5'-to-3' direction. This activity for mesophilic DNA polymerases may be inactivated by heat treatment. For example, T5 DNA polymerase activity is totally inactivated by exposing the enzyme to a temperature of 90° C. for 30 seconds. As used herein, a thermostable polymerase activity is more resistant to heat inactivation than a mesophilic polymerase. However, a thermostable polymerase does not mean to refer to an enzyme which is totally resistant to heat inactivation and thus heat treatment may reduce the polymerase activity to some extent. A thermostable polymerase typically will also have a higher optimum temperature than mesophilic polymerases.

Hybridization. The terms "hybridization" and "hybridizing" refers to the pairing of two complementary single-stranded nucleic acid molecules (RNA and/or DNA) to give a double-stranded molecule. As used herein, two nucleic acid molecules may be hybridized, although the base pairing is not completely complementary. Accordingly, mismatched bases do not prevent hybridization of two nucleic acid molecules provided that appropriate conditions, well known in the art, are used. In the present invention, the term "hybridization" refers particularly to hybridization of an oligonucleotide to a template molecule.

3'–5' Exonuclease Activity. "3'–5' exonuclease activity" is an enzymatic activity well known to the art. This activity is often associated with DNA polymerases, and is thought to be involved in a DNA replication "editing" or correction mechanism.

A "DNA polymerase substantially reduced in 3'–5' exonuclease activity" (which may also be represented as "3'exo–") is defined herein as either (1) a mutated DNA polymerase that has about or less than 10%, or preferably about or less than 1%, of the 3'–5' exonuclease activity of the corresponding unmutated, wildtype enzyme, or (2) a DNA polymerase having a 3'–5' exonuclease specific activity which is less than about 1 unit/mg protein, or preferably about or less than 0.1 units/mg protein. A unit of activity of 3'–5' exonuclease is defined as the amount of activity that solubilizes 10 nmoles of substrate ends in 60 min. at 37° C., assayed as described in the "BRL 1989 Catalogue & Reference Guide", page 5, with HhaI fragments of lambda DNA 3'-end labeled with [$^3$H]dTTP by terminal deoxynucleotidyl transferase (TdT). Protein is measured by the method of Bradford, *Anal. Biochem.* 72:248 (1976). As a means of comparison, natural, wildtype T5-DNA polymerase (DNAP) or T5-DNAP encoded by pTTQ19-T5-2 has a specific activity of about 10 units/mg protein while the DNA polymerase encoded by pTTQ19-T5-2(exo$^-$) (U.S. Pat. No. 5,270,179) has a specific activity of about 0.0001 units/mg protein, or 0.001% of the specific activity of the unmodified enzyme, a $10^5$-fold reduction.

5'–3' Exonuclease Activity. "5'–3' exonuclease activity" is also an enzymatic activity well known in the art. This activity is often associated with DNA polymerases, such as *E. coli* PolI and PolIII.

A "DNA polymerase substantially reduced in 5'–3' exonuclease activity" (which may also be represented as "5'exo–") is defined herein as either (1) a mutated DNA polymerase that has about or less than 10%, or preferably about or less than 1%, of the 5'–3' exonuclease activity of the corresponding unmutated, wildtype enzyme, or (2) a DNA polymerase having 5'–3' exonuclease specific activity which is less than about 1 unit/mg protein, or preferably about or less than 0.1 units/mg protein.

Both of the 3'–5' and 5'–3' exonuclease activities can be observed on sequencing gels. Active 5'–3' exonuclease activity will produce nonspecific ladders in a sequencing gel by removing nucleotides from the 5'-end of the growing primers. 3'–5' exonuclease activity can be measured by following the degradation of radiolabeled primers in a sequencing gel. Thus, the relative amounts of these activities, e.g. by comparing wildtype and mutant polymerases, can be determined with no more than routine experimentation.

Minisatellite DNA. As used herein, the term "minisatellite DNA" refers to a DNA fragment comprising a short stretch of tandemly repetitive nucleotide sequence. In vivo, minisatellite DNA fragments are found interspersed throughout the genomes of most eukaryotic organisms thus far examined. These repeating sequences appear in tandem and often in variable numbers within the genome; thus, the terms "short tandem repeats" ("STRs") or "variable numbers of tandem repeats" ("VNTRs") may be used synonymously when referring to these regions. Minisatellite DNA fragments are typically about 9 bases to about 60 bases in length and are repeated about 20–50 times at a typical locus in a eukaryotic genome.

Microsatellite DNA. As used herein, the term "microsatellite DNA" refers to DNA fragments which are typically of a repeat unit size of about 1–6 bases in length. The most prevalent of these microsatellite DNA fragments in the human genome is the dinucleotide repeat $(dC-dA)_n \cdot (dG-dT)_n$ (where n is the number of repetitions in a given stretch of nucleotides). The terms "STRs" and "VNTRs" may also be used synonymously to denote these structures.

Non-templated 3' Terminal Nucleotide Addition. As used herein, the term "non-templated 3' terminal nucleotide addition" or "extranucleotide addition" means the propensity of an enzyme such as a DNA polymerase to incorporate one or more additional nucleotides, which are not found in the template strand at the 3' terminus of a newly synthesized nucleic acid molecule in a synthesis or amplification reaction, such as PCR. As a result of non-templated 3' terminal nucleotide addition, the synthesized or amplification products (i.e., the newly synthesized DNA strand) will be longer by one or more nucleotides than is the template, in such a fashion that if the template is "n" nucleotides in length, the synthesis or amplification products will be "n+1," "n+2," "n+3," etc., nucleotides in length. A "polymerase substantially reduced in the ability to add one or more non-templated nucleotides to the 3' terminus of a nucleic acid molecule" is defined herein as a DNA polymerase, which when it has no 3' exonuclease activity or has substantially reduced 3' exonuclease activity, it will produce a collection of amplification products in which less than about 50%, preferably less than about 30%, more preferably less than about 20%, still more preferably less than about 10%, still more preferably less than about 5%, and most preferably less than about 1% of the amplification products contain one or more non-templated nucleotides at their 3' termini compared to amplification products produced by Taq DNA polymerase assayed under the same conditions. Preferably, the conditions used for assaying 3' non-templated nucleotide addition is performed such that less than 100% of the amplification products of Taq DNA polymerase exhibits 3' non-templated nucleotide addition. Included in this definition are those polymerases that satisfy this definition for any primer set used. Thus, if the use of any primer set provides the indicated reduction of 3' non-templated nucleotide addition, the polymerase is said to be substantially reduced in the ability to add one or more non-templated nucleotides to the 3' terminus of a nucleic acid molecule.

When referring to polymerases which have been mutated or modified to reduce or eliminate 3' non-templated nucleotide addition, the mutated or modified polymerase is said to be "reduced in the ability to add one or more non-templated nucleotides to the 3' terminus of a nucleic acid molecule" when the polymerase has a lower or reduced or eliminated ability to add non-templated 3' nucleotides compared to the corresponding unmutated, unmodified or wildtype polymerase. For example, when testing the affect of a point mutation in the O-helix of a polymerase on non-templated nucleotide addition, the polymerase unmodified in the same position of the O-helix is preferably used for comparison purposes. Such mutated or modified polymerases are said to "substantially reduced in the ability to add one or more non-templated nucleotides to the 3' terminus of a nucleic acid molecule" if the mutated or modified polymerase has less than about 50%, preferably less than about 30%, more preferably less than about 20%, still more preferably less than about 10%, still more preferably less than about 5%, and most preferably less than about 1% of the activity for adding non-templated 3' terminal nucleotides compared to the corresponding unmutated, unmodified or wildtype polymerase. Preferably, the conditions used for assaying 3' non-templated nucleotide addition is performed such that less than 100% of the amplification products produced by the unmutated, unmodified or wildtype polymerase control exhibits 3' non-templated nucleotide addition. Included in this definition are those mutant or modified polymerases that satisfy this definition for any primer set tested.

The ability of a polymerase to add a non-templated 3' terminal nucleotide to the growing strand may be assessed by a variety of techniques, most preferably by gel electrophoresis of the synthesized or amplification products for a direct size comparison and by comparison to markers of known size (see FIGS. 6–13).

Other terms used in the fields of recombinant DNA technology and molecular and cell biology as used herein will be generally understood by one of ordinary skill in the applicable arts.

Sources of Polymerases

The methods of the present invention rely on the use of polymerases (thermostable or mesophilic DNA or RNA polymerases) reduced, substantially reduced or eliminated in the ability to add one or more non-templated 3' terminal nucleotide to a growing nucleic acid strand. These thermostable DNA polymerases may be obtained from any strain of any thermophilic microorganisn, including but not limited to strains of *Thermus aquaticus* (Taq polymerase; see U.S. Pat. Nos. 4,889,818 and 4,965,188), *Thermus thermophilus* (Tth polymerase), *Thermococcus litoralis* (Tli or VENT™ polymerase), *Pyrococcus furiosus* (Pfu or DEEPVENT™ polymerase), *Pyrococcus woosii* (Pwo polymerase) and other Pyrococcus species, *Bacillus sterothermophilus* (Bst polymerase), *Sulfolobus acidocaldarius* (Sac polymerase), *Thermoplasma acidophilum* (Tac polymerase), *Bacillus caldophilus* (Bca polymerase), *Thermus flavus* (Tfl/Tub polymerase), *Thermus ruber* (Tru polymerase), *Thermus brockianus* (DYNAZYME™ polymerase), *Thermotoga neapolitana* (Tne polymerase; see WO 96/10640 and WO96/41014), *Thermotoga maritima* (Tma polymerase; see U.S. Pat. No. 5,374,553) and other species of the Thermotoga genus (Tsp polymerase) and *Methanobacterium thermoautotrophicum* (Mth polymerase). Mesophilic DNA polymerases of interest in the invention include but are not limited to T7 DNA polymerases, T5 DNA polymerase, DNA polymerase III, Klenow fragment DNA polymerase and mutants, fragments or derivatives thereof. RNA polymerases such as T3, T5, SP6 and mutants, variants and derivatives thereof may also be used in accordance with the invention. Polymerases having reduced or substantially reduced ability to add a non-templated 3' nucleotide to a growing nucleic acid strand may be wildtype polymerases, or may be made by mutating such wildtype polymerases by standard techniques (for example, by generating point mutations, insertions, deletions, etc., in the wildtype gene or protein). Polymerases that are reduced or substantially reduced in the ability to add a non-templated 3' nucleotide to a growing strand may be identified by assaying the synthesized products (e.g. PCR products) formed by such enzymes, as is well-known in the art and as generally described below in the Examples.

The nucleic acid polymerases used in the present invention may be mesophilic or thermophilic, and are preferably thermophilic. Preferred mesophilic DNA polymerases include T7 DNA polymerase, T5 DNA polymerase, Klenow fragment DNA polymerase, DNA polymerase III and the like. Preferred thermostable DNA polymerases that may be used in the methods of the invention include Taq, Tne, Tma, Pfu, Tfl, Tth, Stoffel fragment, VENT™ and DEEPVENT™ DNA polymerases, and mutants, variants and derivatives thereof (U.S. Pat. No. 5,436,149; U.S. Pat. No. 4,889,818; U.S. Pat. No. 4,965,188; U.S. Pat. No. 5,079,352; U.S. Pat. No. 5,614,365; U.S. Pat. No. 5,374,553; U.S. Pat. No. 5,270,179; U.S. Pat. No. 5,047,342; U.S. Pat. No. 5,512,462; WO 92/06188; WO 92/06200; WO 96/10640; Barnes, W. M., *Gene* 112:29–35 (1992); Lawyer, F. C., et al., *PCR Meth. Appl.* 2:275–287 (1993); Flaman, J.-M, et al., *Nucl. Acids Res.* 22(15):3259–3260 (1994)). For amplification of long nucleic acid molecules (e.g., nucleic acid molecules longer than about 3–5 Kb in length), at least two DNA polymerases (one substantially lacking 3' exonuclease activity and the other having 3' exonuclease activity) are typically used. See U.S. Pat. No. 5,436,149; U.S. Pat. No. 5,512,462; Farnes, W. M., *Gene* 112:29–35 (1992); and copending U.S. patent application No. 08/689,814, filed Feb. 14, 1997, the disclosures of which are incorporated herein in their entireties. Examples of DNA polymerases substantially lacking in 3' exonuclease activity include, but are not limited to, Taq, Tne(exo⁻), Tma(exo⁻), Pfu (exo⁻), Pwo(exo⁻) and Tth DNA polymerases, and mutants, variants and derivatives thereof.

Polypeptides having nucleic acid polymerase activity are preferably used in the present methods at a final concentration in solution of about 0.1–200 units per milliliter, about 0.1–50 units per milliliter, about 0.1–40 units per milliliter, about 0.1–3.6 units per milliliter, about 0.1–34 units per milliliter, about 0.1–32 units per milliliter, about 0.1–30 units per milliliter, or about 0.1–20 units per milliliter, and most preferably at a concentration of about 20–40 units per milliliter. Of course, other suitable concentrations of nucleic acid polymerases suitable for use in the invention will be apparent to one or ordinary skill in the art.

In a preferred aspect of the invention, polymerases of the invention and preferably the mutant or modified polymerases of the invention are made by recombinant techniques. A number of cloned polymerase genes are available or may be obtained using standard recombinant techniques.

To clone a gene encoding a polymerase, which may be modified in accordance with the invention, isolated DNA which contains the polymerase gene is used to construct a recombinant library in a vector. Any vector, well known in the art, can be used to clone the DNA polymerase of interest. However, the vector used must be compatible with the host in which the recombinant DNA library will be transformed.

Prokaryotic vectors for constructing the plasmid library include plasmids such as those capable of replication in *E.* coli such as, for example, pBR322, ColE1, pSC101, pUC-vectors (pUC18, pUC19; etc.: In: *Molecular Cloning, A Laboratory Manual*, Cold Spring Harbor Laboratory Press, Cold Spring Harbor, N.Y. (1982); and Sambrook et al., In: Molecular Cloning A Laboratory Manual (2d ed.) Cold Spring Harbor Laboratory Press, Cold Spring Harbor, N.Y. (1989)). Bacillus plasmids include pC194, pC221, pC217, etc. Such plasmids are disclosed by Glyczan, T. In: *The Molecular Biology Bacilli*, Academic Press, York (1982), 307–329. Suitable Streptomyces plasmids include pIJ101 (Kendall et al., *J. Bacteriol* 169:4177–4183 (1987)). Pseudomonas plasmids are reviewed by John et al., (*Rad. Insec. Dis.* 8:693–704 (1986)), and Igaki, (*Jpn. J. Bacteriol.* 33:729–742 (1978)). Broad-host range plasmids or cosmids, such as pCP13 (Darzins and Chakrabarbary, *J. Bacteriol.* 159:9–18, 1984) can also be used for the present invention. The preferred vectors for cloning the genes of the present invention are prokaryotic vectors. Preferably, pCP13 and pUC vectors are used to clone the genes of the present invention.

The preferred host for cloning the polymerase genes of interest is a prokaryotic host. The most preferred prokaryotic host is *E. coli*. However, the desired polymerase genes of the present invention may be cloned in other prokaryotic hosts including, but not limited to, Escherichia, Bacillus, Streptomyces, Pseudomonas, Salmonella, Serratia, and Proteus. Bacterial hosts of particular interest include *E. coli* DH10B, which may be obtained from Life Technologies, Inc. (LTI) (Rockville, Md.).

Eukaryotic hosts for cloning and expression of the polymerases of interest include yeast, fungi, and mammalian cells. Expression of the desired polymerase in such eukaryotic cells may require the use of eukaryotic regulatory regions which include eukaryotic promoters. Cloning and expressing the polymerase gene in eukaryotic cells may be accomplished by well known techniques using well known eukaryotic vector systems.

Once a DNA library has been constructed in a particular vector, an appropriate host is transformed by well known techniques. Transformed colonies are preferably plated at a density of approximately 200–300 colonies per petri dish. For thermostable polymerase selection, colonies are then screened for the expression of a heat stable DNA polymerase by transferring transformed *E. coli* colonies to nitrocellulose membranes. After the transferred cells are grown on nitrocellulose (approximately 12 hours), the cells are lysed by standard techniques, and the membranes are then treated at 95° C. for 5 minutes to inactivate the endogenous *E. coli* enzyme. Other temperatures may be used to inactivate the host polymerases depending on the host used and the temperature stability of the polymerase to be cloned. Stable polymerase activity is then detected by assaying for the presence of polymerase activity using well known techniques (see, e.g., Sagner et al., *Gene* 97:119–123 (1991), which is hereby incorporated by reference in its entirety). The gene encoding a polymerase of the present invention can be cloned using the procedure described by Sanger et al., supra. Other techniques for selecting cloned polymerases in accordance with the present invention will be well-known to those of ordinary skill in the art.

Modifications or Mutations of Polymerases

In accordance with the invention, the nucleotide binding domain of the polymerase of interest is modified or mutated in such a way as to produce a mutated or modified polymerase having reduced, substantially reduced or eliminated activity for adding non-templated 3' nucleotides. The O-helix region typically defines the nucleotide binding domain of DNA polymerases. The O-helix may be defined as RXXXKXXXFXXXYX (SEQ ID NO:11), wherein X may be any amino acid. One or more mutations or combinations of mutations may be made in the O-helix of any polymerase in order to reduce or eliminate non-templated 3' nucleotide addition in accordance with the invention. Such mutations include point mutation, frame-shift mutations, deletions and insertions. Preferably, one or more point mutations, resulting in one or more amino acid substitutions, are used to produce polymerases having such activity. Such mutations may be made by a number of methods that will be familiar to one of ordinary skill, including but not limited to site-directed mutagenesis. In a preferred aspect of the invention, one or more mutations at positions R, K, F, and/or Y in the polymerase O-helix may be made to produced a polymerase having the desired activity. Most preferably, one or more mutations at position R and/or F and/or K and/or Y within the O-helix results in polymerases having reduced, substantially reduced or eliminated activity for adding non-templated 3' nucleotides. In the preferred aspect, amino acid substitutions are made at position R and/or F and/or K and/or Y (or combinations thereof). Thus, R (Arg) and/or F (Phe) and/or K (Lys) may be substituted with any other amino acid including Ala, Arg, Asn, Asp, Cys, Gln, Glu, Gly, His, Ile, Leu, Lys, Met, Phe, Pro, Ser, Thr, Trp, Tyr, and Val. Preferably, R (Arg) is substituted with amino acids Lys, Tyr, Leu, His, Gln, Met, or Asn. F (Phe) is preferably substituted with amino acids Tyr, Ala, Leu, Thr, and Ser. K (Lys) is preferably substituted with amino acids Arg, Tyr, Leu, His, Gln, Met or Asn, and more preferably with Arg or His. Y (Tyr) is preferably substituted with amino acids Lys, Arg, Ala, Thr, Phe, Leu, His, Gln, Met, or Asn. Positions corresponding to R, K, F and Y for RNA polymerases may also be determined by comparing nucleotide and/or amino acid sequences with those of DNA polymerases, to determine homologies therebetween. Corresponding mutations or modification may then be made to produce the desired result in any RNA polymerase.

The O-helix has been identified and defined for a number of polymerases and may be readily identified for other polymerases by one with skill in the art. Thus, given the defined O-helix region and the methods and assays described herein, one with skill in the art can make one or a number of modifications which would result in polymerases having reduced, substantially reduced or eliminated activity for adding non-templated 3' nucleotides. Accordingly, the invention relates to methods for producing such polymerases having modifications in the O-helix domain resulting in reduction, substantial reduction or elimination of activity for adding non-templated 3' nucleotides, methods for producing nucleic acid molecules encoding such polymerases, and polymerases and nucleic acid molecules produced by such methods.

The following table illustrates identified O-helix regions for known polymerases.

| Polymerase | O-Helix Region | SEQ ID NO. |
|---|---|---|
| PolI | 754 RRSAKAINFGLIYG | 12 |
| Taq | 659 RRAAKTINFGVLYG | 13 |
| T7 | 518 RDNAKTFIYGFLYG | 14 |
| Tne | 722 RRVGKMVNFSIIYG | 15 |
| T5 | 588 RQAAKAITFGILYG | 16 |
| Tma | 722 RRAGKMVNFSIIYG | 17 |

Thus, in accordance with a preferred aspect of the invention, corresponding mutations in the R and/or F and/or K positions of the O-helix can be made for the following enzymes based on the tables below.

| Polymerase | Mutation Position |
|---|---|
| PolI | Arg$^{754}$ |
| T5 | Arg$^{588}$ |
| T7 | Arg$^{518}$ |
| Taq | Arg$^{659}$ |
| Tne | Arg$^{722}$ |
| Tma | Arg$^{722}$ |
| Bca | Arg$^{705}$ |
| Bst | Arg$^{702}$ |
| Tth | Arg$^{661}$ |
| PolI | Phe$^{762}$ |
| T5 | Phe$^{596}$ |
| T7 | Phe$^{528}$ |
| Taq | Phe$^{667}$ |
| Tne | Phe$^{730}$ |
| Tma | Phe$^{730}$ |
| Bca | Phe$^{713}$ |
| Bst | Phe$^{710}$ |
| Tth | Phe$^{669}$ |
| PolI | Lys$^{758}$ |
| T5 | Lys$^{592}$ |
| T7 | Lys$^{522}$ |
| Taq | Lys$^{663}$ |
| Tne | Lys$^{726}$ |
| Tma | Lys$^{726}$ |
| Bca | Lys$^{707}$ |
| Bst | Lys$^{706}$ |
| Tth | Lys$^{665}$ |

The mutation position of Arg$^{705}$ for Bca is based on the sequence information in GenBank. It should be noted, however, that according to the sequence described by Vemori et al. *J. Biochem.* (*Japan*) 113:401–410(1993), the position of Arg in Bca is 703.

Additional Modifications or Mutations of Polymerases

In accordance with the invention, in addition to the mutations or modifications described above, one or more additional mutations or modifications (or combinations thereof may be made to the polymerases of interest. Mutations or modifications of particular interest include those modifications of mutations which (1) reduce or eliminate 3' to 5' exonuclease activity; and (2) reduce or eliminate 5' to 3' exonuclease activity.

If the DNA polymerase has 3'-to-5' exonuclease activity, this activity may be reduced, substantially reduced, or eliminated by mutating the polymerase gene. Such mutations include point mutations, frame shift mutations, deletions and insertions. Preferably, the region of the gene encoding the 3'-to-5' exonuclease activity is mutated or deleted using techniques well known in the art (Sambrook et al., (1989) in: *Molecular Cloning, A Laboratory Manual* (2nd Ed.), Cold Spring Harbor Laboratory Press, Cold Spring Harbor, N.Y.).

The 3'-to-5' exonuclease activity can be reduced or impaired by creating site specific mutants within the 3'→5' exonuclease domain. See infra. In a specific embodiment of the invention Asp$^{323}$ of Tne DNA polymerase is changed to any amino acid, preferably to Ala$^{323}$ to substantially reduce 3'→5' exonuclease activity. In another specific embodiment of the invention, Asp$^{323}$ of Tma may be changed to any other amino acid, preferably to Ala to substantially reduce 3'→5' exonuclease activity. The following represents a domain of interest for a number of polymerases for preparing 3'→5' exonuclease mutants.

| Tne | 318 | PSFALDLETSS | 328 | (SEQ ID NO: 18) |
|---|---|---|---|---|
| Pol I | 350 | PVFAFDTETDS | 360 | (SEQ ID NO: 19) |
| T5 | 159 | GPVAFDSETSA | 169 | (SEQ ID NO: 20) |
| T7 | 1 | MIVSDIEANA | 10 | (SEQ ID NO: 21) |

Mutations, such as insertions, deletions and substitutions within the above domain can result in substantially reduced 3'→5' exonuclease activity. By way of example, Asp$^{355}$ (PolI), Asp$^{164}$ (T5), and Asp$^{5}$ (T7) may be substituted with any amino acid to substantially reduce 3'→5' exonuclease activity. For example, Asp at these positions may be substituted with Ala.

The 5'→3' exonuclease activity of the polymerases can be reduced, substantially reduced or eliminated by mutating the polymerase gene or by deleting the 5' to 3' exonuclease domain. Such mutations include point mutations, frame shift mutations, deletions, and insertions. Preferably, the region of the gene encoding the 5'→3' exonuclease activity is deleted using techniques well known in the art. In embodiments of this invention, any one of six conserved amino acids that are associated with the 5'→3' exonuclease activity can be mutated. Examples of these conserved amino acids with respect to Tne DNA polymerase include Asp$^{8}$, Glu$^{112}$, Asp$^{114}$, Asp$^{115}$, Asp$^{137}$, and Asp$^{139}$. Other possible sites for mutation are Gly$^{102}$, Gly$^{187}$ and Gly$^{195}$.

Corresponding amino acid to target for other polymerases to reduce or eliminate 5'→3' exonuclease activity as follows:

*E. coli* polI: Asp$^{13}$, Glu$^{113}$, Asp$^{115}$, Asp$^{116}$, Asp$^{138}$, and Asp$^{140}$.

Taq pol: Asp$^{18}$, Glu$^{117}$, Asp$^{119}$, Asp$^{120}$, Asp$^{142}$, and Asp$^{144}$.

Tma pol: Asp$^{8}$, Glu$^{112}$, Asp$^{114}$, Asp$^{115}$, Asp$^{137}$, and Asp$^{139}$.

Amino acid residues of Taq DNA polymerase are as numbered in U.S. Pat. No. 5,079,352. Amino acid residues of *Thermotogamaritima* (Tma) DNA polymerase are numbered as in U.S. Pat. No. 5,374,553.

Examples of other amino acids which may be targeted for other polymerases to reduce 5'→3' exonuclease activity include:

| Enzyme or source | Mutation positions |
|---|---|
| Streptococcus pneumoniae | Asp$^{10}$, Glu$^{114}$, Asp$^{116}$, Asp$^{117}$, Asp$^{139}$, Asp$^{141}$ |
| Thermus flavus | Asp$^{17}$, Glu$^{116}$, Asp$^{118}$, Asp$^{119}$, Asp$^{141}$, Asp$^{143}$ |
| Thermus thermophilus | Asp$^{18}$, Glu$^{118}$, Asp$^{120}$, Asp$^{121}$, Asp$^{143}$, Asp$^{145}$ |
| Deinococcus radiodurans | Asp$^{18}$, Glu$^{117}$, Asp$^{119}$, Asp$^{120}$, Asp$^{142}$, Asp$^{144}$ |
| Bacillus caldotenax | Asp$^{9}$, Glu$^{109}$, Asp$^{111}$, Asp$^{112}$, Asp$^{134}$, Asp$^{136}$ |

Coordinates of *S. pneumoniae, T. flavus, D. radiodurans, B. caldotenax* were obtained from Gutman and Minton. Coordinates of *T. thermophilus* were obtained from International Patent No. WO 92/06200.

Typically, the mutant polymerases of the invention can be affected by substitution of amino acids typically which have different properties. For example, an acidic amino acid such as Asp may be changed to a basic, neutral or polar but uncharged amino acid such as Lys, Arg, His (basic); Ala, Val, Leu, Ile, Pro, Met, Phe, Trp (neutral); or Gly, Ser, Thr, Cys, Tyr, Asn or Gln (polar but uncharged). Glu may be changed to Asp, Ala, Val Leu, Ile, Pro, Met, Phe, Trp, Gly, Ser, Thr, Cys, Tyr, Asn or Gln.

Preferably, oligonucleotide directed mutagenesis is used to create the mutant polymerases which allows for all possible classes of base pair changes at any determined site along the encoding DNA molecule. In general, this technique involves annealing a oligonucleotide complementary (except for one or more mismatches) to a single stranded nucleotide sequence coding for the DNA polymerase of interest. The mismatched oligonucleotide is then extended by DNA polymerase, generating a double stranded DNA molecule which contains the desired change in the sequence on one strand. The changes in sequence can of course result in the deletion, substitution, or insertion of an amino acid. The double stranded polynucleotide can then be inserted into an appropriate expression vector, and a mutant polypeptide can thus be produced. The above-described oligonucleotide directed mutagenesis can of course be carried out via PCR.

Enhancing Expression of Polymerases

To optimize expression of the polymerases of the present invention, inducible or constitutive promoters are well known and may be used to express high levels of a polymerase structural gene in a recombinant host. Similarly, high copy number vectors, well known in the art, may be used to achieve high levels of expression. Vectors having an inducible high copy number may also be useful to enhance expression of the polymerases of the invention in a recombinant host.

To express the desired structural gene in a prokaryotic cell (such as, E. coli, B. subtilis, Pseudomonas, etc.), it is necessary to operably link the desired structural gene to a functional prokaryotic promoter. However, the natural promoter of the polymerase gene may function in prokaryotic hosts allowing expression of the polymerase gene. Thus, the natural promoter or other promoters may be used to express the polymerase gene. Such other promoters may be used to enhance expression and may either be constitutive or regulatable (i.e., inducible or derepressible) promoters. Examples of constittitive promoters include the int promoter of bacteriophage λ, and the bla promoter of the β-lactamase gene of pBR322. Examples of inducible prokaryotic promoters include the major right and left promoters of bacteriophage λ ($P_R$ and $P_L$), trp, recA, lacZ, lacI, tet, gal, trc, and tac promoters of E. coli. The B. subtilis promoters include α-amylase (Ulmanen et al., J. Bacteriol 162:176–182 (1985)) and Bacillus bacteriophage promoters (Gryczan, T., In: The Molecular Biology Of Bacilli, Academic Press, New York (1982)). Streptomyces promoters are described by Ward et al., Mol. Gen. Genet. 203:468478 (1986)). Prokaryotic promoters are also reviewed by Glick, J. Ind. Microbiol. 1:277–282 (1987); Cenatiempto, Y., Biochimie 68:505–516 (1986); and Gottesman, Ann. Rev. Genet. 18:415–442 (1984). Expression in a prokaryotic cell also requires the presence of a ribosomal binding site upstream of the gene-encoding sequence. Such ribosomal binding sites are disclosed, for example, by Gold et al., Ann. Rev. Microbiol. 35:365404 (1981).

To enhance the expression of polymerases of the invention in a eukaryotic cell, well known eukaryotic promoters and hosts may be used. Preferably, however, enhanced expression of the polymerases is accomplished in a prokaryotic host. The preferred prokaryotic host for overexpressing the polymerases of the invention is E. coli.

Isolation and Purification of Polymerases

The enzyme(s) of the present invention is preferably produced by fermentation of the recombinant host containing and expressing the desired polymerase gene. However, the polymerases of the present invention may be isolated from any strain which produces the polymerase of the present invention. Fragments of the polymerase are also included in the present invention. Such fragments include proteolytic fragments and fragments having polymerase activity.

Any nutrient that can be assimilated by a host containing the polymerase gene may be added to the culture medium. Optimal culture conditions should be selected case by case according to the strain used and the composition of the culture medium. Antibiotics may also be added to the growth media to insure maintenance of vector DNA containing the desired gene to be expressed. Media formulations have been described in DSM or ATCC Catalogs and Sambrook et al., In:

Molecular Cloning, a Laboratory Manual(2nd ed.), Cold Spring Harbor Laboratory Press, Cold Spring Harbor, N.Y. (1989).

Host cells producing the polymerases of this invention can be separated from liquid culture, for example, by centrifugation. In general, the collected microbial cells are dispersed in a suitable buffer, and then broken down by ultrasonic treatment or by other well known procedures to allow extraction of the enzymes by the buffer solution. After removal of cell debris by ultracentrifugation or centrifugation, the polymerase can be purified by standard protein purification techniques such as extraction, precipitation, chromatography, affinity chromatography, electrophoresis or the like. Assays to detect the presence of the polymerase during purification are well known in the art and can be used during conventional biochemical purification methods to determine the presence of these enzymes.

Thermotoga Polymerases

Thermotoga polymerases for use in the present invention are obtained from any strain of Thermotoga species, more preferably from a strain of Thermotoga neapolitana (WO 96/10640 or WO96/41014) or Thermotoga maritima (U.S. Pat. No. 5,374,553). Enzymes suitable for use in the present invention from these more preferred sources are the wild-type DNA polymerases (Tne from T. neapolitana; Tma from T. maritima), or mutants or derivatives thereof.

The present invention provides isolated nucleic acid molecules encoding preferred mutant Tne DNA polymerases, mutant Tne DNA polymerases encoded by such isolated nucleic acid molecules, and specific mutant Tne DNA polymerase proteins. Most preferred are the wildtype Tne DNA polymerase (SEQ ID NOs: 1,2), the wildtype Tma DNA polymerase (U.S. Pat. No. 5,374,553), and the following mutants of Tne DNA polymerase: Tne N'Δ219, D323A (SEQ ID NO:3); Tne N'Δ283, D323A (SEQ ID NO:4); Tne N'Δ192, D323A (SEQ ID NO:5); Tne D137A, D323A (SEQ ID NO:6); Tne D8A, D323A (SEQ ID NO:7); Tne G195D, D323A (SEQ ID NO:8); Tne G37D, D323A (SEQ ID NO:9); Tne N'Δ283 (SEQ ID NO:10); Tne D137A, D323A, R722K; Tne D137A, D323A, R722Y; Tne D137A, D323A, R722L; Tne D137A, D323A, R722H; Tne D137A, D323A, R722Q; Tne D137A, D323A, F730Y; Tne D137A, D323A, K726R; Tne D137A, D323A, K726H; Tne D137A, D323A, R722K, F730Y; Tne D137A, D323A, R722K, K726R; Tne D137A, D323A, R722K, K726H; Tne D137A, D323A, R722H, F730Y; Tne D137A, D323A, R722H, K726R; Tne D137A, D323A, R722H, K726H; Tne D137A, D323A, R722Q, F730Y; Tne D137A, D323A, R722Q, K726R; Tne D137A, D323A, R722Q, K726H; Tne D137A, D323A, R722N, F730Y; Tne D137A, D323A, R722N, K726R; Tne D137A, D323A, R722N, K726H; Tne D137A, D323A, F730S; Tne N'Δ283, D323A, R722K/H/Q/N/Y/L; Tne N'Δ219, D323A, R722K; Tne N'Δ219, D323A, F730Y; Tne N'Δ219, D323A, K726R; Tne N'Δ219, D323A, K726H; Tne D137A, D323A, F730S, R722K/Y/Q/N/H/L, K726H; Tne D137A, D323A, F730T, R722K/Y/Q/N/H/L, K726R/H; Tne D137A, D323A, F730T; Tne F730S; Tne F730A; Tne K726R; Tne K726H; and Tne D137A, D323A, R722N. It will of course be understood by the skilled artisan that the designations of the above-described mutant polymerases indicate the position of the amino acid residue in the wildtype amino acid sequence (SEQ ID NO:2) that is being mutated, as well as to what residue the amino acid is being mutated. Thus, for example, "D137A" indicates that the Asp (D) residue at position 137 in SEQ ID NO:2 has been mutated to an Ala (A) residue, and, for example, "R722K/Y/Q/N/H/L" indicates that the Arg (R) residue at position 722 in SEQ ID NO:2 has been mutated to a Lys (K), Tyr (Y), Gln (Q), Asn (N), His (H) or Leu (L) residue. Mutant polymerases having one or more mutations or modifications corresponding to the Tne mutants of the invention are also contemplated by the invention.

The following chart indicates the nucleic acid sequences of the nucleic acid molecules encoding the above-described mutant Tne DNA polymerases (SEQ ID NOs:3–10), each with reference to the wildtype Tne DNA polymerase (SEQ ID NO:1):

| SEQ ID NO: | Deletion of SEQ ID NO: 1 | Insertion | Substitution to SEQ ID NO: 1 |
|---|---|---|---|
| 3 | Deletion of positions 1–657 from the 5'-end | ATG AGC TTC at the 5'-end | A replaces G at position 966; C replaces A at 968 and G replaces C at 969 |
| 4 | Deletion of positions 1–849 from the 5'-end | None | A replaces G at 966; C replaces A at 968 and G replaces C at 969 |
| 5 | Deletion of positions 1–576 from the 5'-end | ATG AAT TCG AGC TCG GTA CCC at the 5'-end | A replaces G at 966; C replaces A at 968 and G replaces C at 969; A replaces G at 584 |
| 6 | None | None | A replaces G at 966; C replaces A at 968 and G replaces C at 969; C replaces T at 408 and C replaces A at 410 |
| 7 | None | None | A replaces G at 966; C replaces A at 968 and G replaces C at 969; C replaces A at 23 and C replaces T at 24 |
| 8 | None | None | A replaces G at 966; C replaces A at 968 and G replaces C at 969; T replaces C at 576 and A replaces G at 584 |
| 9 | None | None | A replaces G at 966; C replaces A at 968 and G replaces C at 969; A replaces G at 110 |
| 10 | Deletion of positions 1–849 from the 5'-end | None | None |

Using these same approaches, the sequence guidance provided herein, and knowledge of appropriate nucleotide substitutions to be made to SEQ ID NO:1, one of ordinary skill can readily produce other nucleic acid molecules encoding mutant polymerases, such as those described in detail above, having the desired activity. In addition, other nucleic acid molecules which comprise a sequence substantially different from those described above but which, due to the degeneracy of the genetic code, still encode a mutant Tne DNA polymerase having an amino acid sequence set forth above, are also encompassed by the present invention. Since the genetic code is well known in the art, it is routine for one of ordinary skill in the art to produce such mutants and degenerate variants without undue experimentation.

Each of these mutant Tne DNA polymerases are reduced or substantially reduced in the ability to add a non-templated 3' terminal nucleotide to the growing strand. These mutant Tne DNA polymerase proteins may be prepared by recombinant DNA techniques routine to one of ordinary skill. Preferably, such mutant Tne polymerases are prepared by inserting an isolated DNA molecule having a nucleotide sequence as described above for each individual mutant into a recombinant vector, inserting the vector into a host cell, preferably an *Escherichia coli* cell, and culturing the host cell under conditions favoring the production of the mutant Tne DNA polymerase. The mutant Tne polymerase is then isolated from the host cell according to standard protein purification techniques. Further guidance for the preparation and isolation of mutant DNA polymerases from thermostable microorganisms can be found, for example, in U.S. Pat. No. 5,374,553, in co-pending U.S. patent application Ser. No. 08/689,818 of Deb K. Chatterjee and A. John Hughes, entitled "Cloned DNA Polymerases from Thermotoga and Mutants Therof," filed Sep. 6, 1996, and in co-pending U.S. patent application Ser. No. 08/689,807 of Deb K. Chatterjee, entitled "Cloned DNA Polymerases from Thermotoga and Mutants Therof," filed Sep. 6, 1996, the disclosures of all of which are incorporated herein in their entirety.

In the methods of the present invention, Thermotoga DNA polymerases substantially reduced in 3'–5' exonuclease activity (such as a Tne mutant having an amino acid sequence as set forth in any one of SEQ ID NOs:3–9), or Thermotoga DNA polymerases not substantially reduced in 3'–5' exonuclease activity (such as Tne DNA polymerase (SEQ ID NOs:1,2), Tma DNA polymerase (U.S. Pat. No. 5,374,553), or the Tne mutant Tne N'Δ283 (SEQ ID NO:10)), may be used with similar results, since both types of Thermotoga DNA polymerase are substantially reduced in the ability to add a nontemplated 3' terminal nucleotide to a DNA template. Other thermostable DNA polymerases substantially reduced in 3'–5' exonuclease activity, such as Taq, VENT™(exo–), DEEPVENT™(exo–), Dtok(exo–) and THERMOLASE™ Tbr, are not preferred for use in the present methods as they will add non-templated nucleotides to the 3' termini of the amplification products as described below. However, such thermostable polymerase can be made which have reduced, substantially reduced or eliminated activity to add 3' non-template nucleotides by mutating or modifying the polymerase in accordance with the invention. The preferred Thermotoga polymerases of the invention contain such mutations or modifications in their O-helix.

The recombinant host comprising the gene encoding Tne DNA polymerase, *E. coli* DH10B(pUC-Tne), was deposited on Sep. 30, 1994, with the Collection, Agricultural Research Culture Collection (NRRL), 1815 North University Street, Peoria, Ill. 61604 USA, as Deposit No. NRRL B-21238. The gene encoding Tma DNA polymerase has also been cloned and sequenced (U.S. Pat. No. 5,374,553, which is expressly incorporated by reference herein in its entirety). Methods for preparing mutants and derivatives of these Tne and Tma polymerases are well-known in the art, and are specifically described in co-pending U.S. Pat. application Ser. No. 08/689,818 of Deb K. Chatterjee and A. John Hughes, entitled "Cloned DNA Polymerases from Thermotoga and Mutants Therof," filed Sep. 6, 1996, and co-pending U.S. Patent application Ser. No. 08/689,807 of Deb K. Chatterjee, entitled "Cloned DNA Polymerases from Thermotoga and Mutants Therof," filed Sep. 6, 1996, the disclosures of which are incorporated herein in their entirety.

Advantages of Thermostable Polymerases

The use of thermostable polymerases (e.g. Thermotoga polymerases) or mutants or derivatives thereof in the methods of the present invention provide several distinct advantages. These advantages are particularly apparent in the application of the present methods to analysis and typing of minisatellite, microsatellite and STR DNA regions.

With respect to traditional thermolabile DNA polymerases used in DNA amplification and sequencing, such as T4, T7 or *E. coli* Klenow fragment polymerases, thermostable polymerases such as Thermotoga DNA polymerases maintain their enzymatic activity in the multiple high-temperature cycles used in PCR and analogous automated amplification methodologies. It is therefore unnecessary to add fresh enzyme at the beginning of each amplification cycle when using thermostable polymerases, as must be done when thermolabile enzymes are used.

With respect to other thermostable enzymes, it has been unexpectedly discovered in the present invention (as described in more detail in the Examples below) that the use of Tne or Tma DNA polymerase mutants or derivatives thereof, does not result in the incorporation of non-templated 3' nucleotides into the newly synthesized DNA strands during DNA amplification reactions. This non-templated incorporation is a common problem when using certain other commonly employed thermostable enzymes, such as Taq, VENT™(exo–), DEEPVENT™(exo–), Dtok (exo–) and THERMOLASE™ Tbr. It has also been unexpectedly discovered that mutants of these polymerases can be made to reduce or eliminate addition of non-templated 3' nucleotides. In particular, such mutations are preferably made within the O-helix of such polymerases.

Thus, the use of Tne or Tma DNA polymerases or mutants or derivatives thereof (or other mutant polymerases produced according to the invention) in amplifying and typing DNA sequences, particularly hypervariable DNA sequences such as minisatellite, microsatellite or STR regions, will allow a faithful amplification and resolution of polymorphisms in these regions. This faithful resolution is not possible using other thermostable polymerases due to their propensity for non-templated incorporation. Thus, these enzymes are suitable for use in automated amplification systems such as PCR.

Sources of DNA

Suitable sources of DNA, including a variety of cells, tissues, organs or organisms, may be obtained through any number of commercial sources (including American Type Culture Collection (ATCC), Rockville, Md.; Jackson Laboratories, Bar Harbor, Me.; Cell Systems, Inc., Kirkland, Wash.; Advanced Tissue Sciences, La Jolla, Calif.). Cells that may be used as starting materials for genomic DNA preparation are preferably eukaryotic (including fungi or yeasts, plants, protozoans and other parasites, and animals including humans and other mammals). Although any mammalian cell may be used for preparation of DNA, preferred are blood cells (erythrocytes and leukocytes), endothelial cells, epithelial cells, neuronal cells (from the central or peripheral nervous systems), muscle cells (including myocytes and myoblasts from skeletal, smooth or cardiac muscle), connective tissue cells (including fibroblasts, adipocytes, chondrocytes, chondroblasts, osteocytes and osteoblasts) and other stromal cells (e.g., macrophages, dendritic cells, Schwann cells), although other cells, including the progenitors, precursors and stem cells that give rise to the above-described somatic cells, are equally suitable. Also suitable for use in the preparation of DNA are mammalian tissues or organs such as those derived from brain, kidney, liver, pancreas, blood, bone marrow, muscle, nervous, skin, genitourinary, circulatory, lymphoid, gastrointestinal and connective tissue sources, as well as those derived from a mammalian (including human) embryo or fetus. These cells, tissues and organs may be normal, or they may be pathological such as those involved in infectious diseases (caused by bacteria, fungi or yeast, viruses (including AIDS) or parasites), in genetic orbiochemical pathologies (e.g., cystic fibrosis, hemophilia, Alzheimer's disease, schizophrenia, muscular dystrophy or multiple sclerosis), or in cancerous processes.

More specifically, in one aspect of the invention, the relationship between a first individual and a second individual may be determined by analyzing and typing a particular polymorphic DNA fragment, such as a minisatellite or microsatellite DNA sequence. In such a method, the amplified fragments for each individual are compared to determine similarities or dissimilarities. Such an analysis is accomplished, for example, by comparing the size of the amplified fragments from each individual, or by comparing the sequence of the amplified fragments from each individual. In another aspect of the invention, genetic identity can be determined. Such identity testing is important, for example, in paternity testing, forensic analysis, etc. In this aspect of the invention, a sample containing DNA (e.g., a crime scene sample or a sample from an individual) is analyzed and compared to a sample from one or more individuals. In one such aspect of the invention, one sample of DNA may be derived from a first individual and another sample may be derived from a second individual whose relationship to the first individual is unknown; comparison of these samples from the first and second individuals by the methods of the invention may then facilitate a determination of the genetic identity or relationship between the first and second a individual. In a particularly preferred such aspect, the first DNA sample may be a known sample derived from a known individual and the second DNA sample may be an unknown sample derived, for example, from crime scene material. In an additional aspect of the invention, one sample of DNA may be derived from a first individual and another sample may be derived from a second individual who is related to the first individual; comparison of these samples from the first and second individuals by the methods of the invention may then facilitate a determination of the genetic kinship of the first and second individuals by allowing examination of the Mendelian inheritance, for example, of a polymorphic, minisatellite, microsatellite or STR DNA fragment. In another aspect of the invention, DNA fragments important as genetic markers for encoding a gene of interest can be identified and isolated. For example, by comparing samples from different sources, DNA fragments which may be important in causing diseases such as infectious diseases (of bacterial, fungal, parasitic or viral etiology), cancers or genetic diseases, can be identified and characterized. In this aspect of the invention a DNA sample from normal cells or tissue is compared to a DNA sample from diseased cells or tissue. Upon comparison according to the invention, one or more unique polymorphic fragments present in one DNA sample and not present in the other DNA sample can be identified and isolated. Identification of such unique polymorphic fragments allows for identification of sequences associated with, or involved in, causing the diseased state.

Once the starting cells, tissues, organs or other samples are obtained, DNA may be prepared therefrom by methods that are well-known in the art (See, e.g., Maniatis, T., et al., *Molecular Cloning: A Laboratory Manual*, Cold Spring Harbor, N.Y.: Cold Spring Harbor Laboratory Press, pp.

9.16–9.23 (1989); Kaufman, P. B., et al, *Handbook of Molecular and Cellular Methods in Biology and Medicine*, Boca Raton, Fla.: CRC Press, pp. 1–26 (1995)). The DNA samples thus prepared may then be used to identify, analyze and type polymorphic DNA fragments, including minisatellite, microsatellite and STR DNA fragments, by amplification, preferably by PCR amplification, as modified by the methods of the present invention.

General methods for amplification and analysis of DNA fragments are well-known to one of ordinary skill in the art (see, e.g., U.S. Pat. Nos. 4,683,195; 4,683,202; and 4,800,159; Innis, M. A., et al., eds., *PCR Protocols: A Guide to Methods and Applications*, San Diego, Calif.: Academic Press, Inc. (1990); Griffin, H. G., and Griffin, A. M., eds., *PCR Technology: Current Innovations*, Boca Raton, Fla.: CRC Press (1994)). Typically, these methods comprise contacting the DNA sample with a thermostable DNA polymerase in the presence of one or more primer sequences, amplifying the DNA sample to generate a collection of amplified polymorphic, minisatellite, microsatellite or STR DNA fragments, preferably by PCR or equivalent automated amplification technique, separating the amplified DNA fragments by size, preferably by gel electrophoresis, and analyzing the gels for the presence of polymorphic, minisatellite, microsatellite or STR DNA fragments by direct comparison of the pattern of fragments generated from a first sample of DNA to those from a second sample of DNA, or by a more indirect comparison using known size markers.

As noted above, amplification protocols used heretofore for analyzing and typing polymorphic DNA fragments, particularly minisatellite, microsatellite or STR DNA sequences, use certain thermostable DNA polymerases such as Taq (U.S. Pat. Nos. 4,683,195; 4,683,202; and 4,800,159). However, as discussed in detail above, these approaches yield amplification products in which one or more non-templated nucleotides is added to the 3' termini of the products by the polymerases, thus leading to heterogeneity in the amplification products, and ambiguity concerning the correct size of the amplification products.

This problem is overcome in the present invention by contacting the DNA sample in the amplification reaction mixtures with one or more DNA polymerases of the invention which are reduced, substantially reduced or eliminated in the ability to add a nontemplated 3' terminal nucleotide to the growing strand. Preferably, such DNA polymerases are Thermotoga DNA polymerases, more preferably a Thermotoga DNA polymerase substantially reduced in 3'–5' exonuclease activity, still more preferably a Tne polymerase (SEQ ID NOs:1,2), a Tma polymerase (U.S. Pat. No. 5,374,553), or a mutant or derivative thereof, and most preferably one of the following mutants of Tne polymerase: Tne N'Δ219, D323A (SEQ ID NO:3); Tne N'Δ283, D323A (SEQ ID NO:4); Tne N'Δ192, D323A (SEQ ID NO:5); Tne D137A, D323A (SEQ ID NO:6); Tne D8A, D323A (SEQ ID NO:7); Tne G195D, D323A (SEQ ID NO:8); Tne G37D, D323A (SEQ ID NO:9); Tne N'Δ283 (SEQ ID NO:10); Tne D137A, D323A, R722K; Tne D137A, D323A, R722Y; Tne D137A, D323A, R722L; Tne D137A, D323A, R722H; Tne D137A, D323A, R722Q; Tne D137A, D323A, F730Y; Tne D137A, D323A, K726R; Tne D137A, D323A, K726H; Tne D137A, D323A, R722K, F730Y; Tne D137A, D323A, R722K, K726R; Tne D137A, D323A, R722K, K726H; Tne D137A, D323A, R722K, F730Y; Tne D137A, D323A, R722H, K726R; Tne D137A, D323A, R722H, K726H; Tne D137A, D323A, R722Q, F730Y; Tne D137A, D323A, R722Q, K726R; Tne D137A, D323A, R722Q, K726H; Tne D137A, D323A, R722Q, K726H; Tne D137A, D323A, R722N, F730Y; Tne D137A, D323A, R722N, K726R; Tne D137A, D323A, R722N, K726H; Tne D137A, D323A, F730S; Tne N'Δ283, D323A, R722K/H/Q/N/Y/L; Tne N'Δ219, D323A, R722K; Tne N'Δ219, D323A, F730Y; Tne N'Δ219, D323A, K726R; Tne N'Δ219, D323A, K726H; Tne D137A, D323A, F730S, R722K/Y/Q/N/H/L, K726R/H; Tne D137A, D323A, F730T, R722K/Y/Q/N/H/L, K726R/H; Tne D137A, D323A, F730T; Tne F730S; Tne F730A; Tne K726R; Tne K726H; and Tne D137A, D323A, R722N.

It will be understood, however, that other thermostable DNA polymerases or mutants thereof, any of which are reduced, substantially reduced, or eliminated in the ability to add a non-templated 3' terminal nucleotide to the growing strand, may be used in the methods of the present invention equivalently. The DNA polymerases are used in the methods of the present invention at a concentration of about 0.0001 units/ml to about 10 units/ml, preferably at a concentration of about 0.001 units/ml to about 5 units/ml, more preferably at a concentration of about 0.004 units/ml to about 1 unit/ml, and most preferably at a concentration of about 0.04 units/ml. Thus, the methods of the present invention produce a population of amplified DNA fragments, most preferably of polymorphic or microsatellite DNA fragments, which comprise substantially no non-templated 3' terminal nucleotides. By "substantially no non-templated 3' terminal nucleotides" is meant that the population of amplified DNA fragments demonstrates about 0–50%, about 0–30%, about 0–20%, preferably about 0–10%, more preferably about 0–5%, still more preferably about 0–1% and most preferably about 0%, of DNA molecules containing non-templated 3' nucleotides compared to amplified DNA fragments produced by the polymerase control. When testing the ability of a DNA polymerase to add 3' non-templated nucleotides, the polymerase, when it has substantially reduced or eliminated 3' exonuclease activity, is compared to Taq DNA polymerase (see above). When testing polymerases which have been modified or mutated to reduce or eliminate 3' non-templated nucleotide addition, the mutated or modified polymerase is compared to the corresponding wildtype, unmodified or unmutated polymerase (see above).

Following amplification by the methods of the present invention, the amplified DNA fragments may be analyzed to identify or type a polymorphic, minisatellite, microsatellite or STR DNA fragment. This step is usually accomplished by separation of the amplified DNA fragments by size, a procedure which permits the determination of the presence of unique polymorphic fragments in one or more of the DNA samples. The fragments may be separated by any physical or biochemical means including gel electrophoresis, capillary electrophoresis, chromatography (including sizing, affinity and immunochromatography), density gradient centrifgation and immunoadsorption. For carrying out the present invention, separation of DNA fragments by gel electrophoresis is particularly preferred, as it provides a rapid and highly reproducible means of sensitive separation of a multitude of DNA fragments, and permits direct, simultaneous comparison of the fragments in several samples of DNA, or samples of DNA from a first and a second individual.

Gel electrophoresis is typically performed on agarose or polyacrylamide sequencing gels according to standard protocols, preferably using gels containing polyacrylamide at concentrations of 3–12% and most preferably at about 8%, and containing urea at a concentration of about 4–12M, most preferably about 8M. Samples are loaded onto the gels, usually with samples containing amplified DNA fragments prepared from different sources of genomic DNA being loaded into adjacent lanes of the gel to facilitate subsequent comparison. Reference markers of known sizes may be used to facilitate the comparison of samples. Following electrophoretic separation, DNA fragments may be visualized and identified by a variety of techniques that are routine to those of ordinary skill in the art, such as autoradiography. One can then examine the autoradiographic films either for differences in polymorphic fragment patterns ("typing") or for the presence of one or more unique bands in one lane of the gel ("identifying"); the presence of a band in one lane (corresponding to a single sample, cell or tissue type) that is not observed in other lanes indicates that the DNA fragment comprising that unique band is source-specific and thus a potential polymorphic DNA fragment.

A variety of DNA fragments comprising polymorphic, minisatellite, microsatellite or STR DNA fragments can thus be identified using the methods of the present invention by comparing the pattern of bands on the films depicting various samples. Importantly, using the present methods the amplification products of the polymorphic DNA fragments will be faithful copies of the template (allele) material—i.e., they will not exhibit undesired additional nucleotides at their 3' termini via non-templated addition of nucleotides by the polymerases. One can extend this approach, in another preferred embodiment, to isolate and characterize these fragments or any DNA fragment amplified without the non-templated addition of a 3' terminal nucleotide. In this embodiment, one or more of the unique DNA fragments are removed from the gel which was used for identification (see above), according to standard techniques such as electroelution or physical excision.

The isolated unique DNA fragments may then be inserted into standard nucleotide vectors, including expression vectors, suitable for transfection or transformation of a variety of prokaryotic (bacterial) or eukaryotic (yeast, plant or animal including human and other mammalian) cells. In particular, the present invention provides methods of cloning such isolated unique DNA fragments, or any PCR-amplified DNA fragment, by blunt-end cloning. As described above, Taq DNA polymerase adds a non-templated nucleotide, typically a deoxyadenosine ("A"), to the 3' terminus of the amplified DNA fragment. Thus, Taq-catalyzed PCR generates a collection of DNA fragments with 3' A overhangs. To clone such Taq-amplified fragments, two approaches are commonly used: either the 3' A overhang is removed by treating the amplified fragment with, for example, T4 DNA polymerase (a technique sometimes called "3' polishing"), or a special cloning vector with a 3' T overhang (a "TA cloning vector") is used. Of course, such approaches are more time-consuming and expensive than if direct insertion of the amplified fragment were done. Such a direct approach is possible using the methods of the invention, which generates little or no 3' A overhangs (and thus, blunt ends) on the amplified DNA fragments. The DNA fragments, amplified according to the methods of the invention, may thus be directly inserted into corresponding blunt-ended vectors according to standard techniques (for example, using T4 DNA ligase). Thus, the present invention provides a method of blunt-end cloning of a DNA fragment that obviates the use of TA cloning vectors or 3' polishing.

To identify the presence of minisatellite DNA fragments, the polymorphic DNA fragments that are identified and isolated by the methods of the present invention may be further characterized, for example by sequencing (i.e., determining the nucleotide sequence of the polymorphic fragments), by methods described above and others that are standard in the art (see, e.g., U.S. Pat. Nos. 4,962,022 and 5,498,523, which are directed to methods of DNA sequencing).

Kits

The invention also provides kits for use in the identification, analysis and typing of a polymorphic DNA fragment, particularly a minisatellite or STR DNA fragment, according to the present methods. Kits according to the present invention may comprise a carrying means being compartmentalized to receive in close confinement therein one or more containers such as vials, tubes, bottles and the like. Each of such containers may comprise components or a mixture of components needed to perform DNA amplification or analysis.

Such kits may comprise of one or more thermostable DNA polymerases reduced, substantially reduced or eliminated in the ability to add a non-templated 3' nucleotide to a growing DNA strand. Preferably the container contains a Thermotoga DNA polymerase or a mutant or a derivative thereof, particularly those described in full detail above. The kit may also contain one or more DNA primer molecules, one or more deoxyribonucleoside triphosphates needed to synthesize a DNA molecule complementary to a DNA template, and/or a buffer suitable for amplification of a nucleic acid molecule (or combinations thereof).

A kit for DNA analysis may include one or more of the above components, and may further include containers which contain reagents necessary for separation and analysis of DNA fragments, such as polyacrylamide, agarose, urea, detergents and the like.

Of course, it is also possible to combine one or more of these reagents in a single tube. A detailed description of such formulations at working concentrations is described in co-pending U.S. application Ser. No. 08/689,815 of Ayoub Rashtchian and Joseph Solus, entitled "Stable Compositions for Nucleic Acid Amplification and Sequencing" filed on Aug. 14, 1996, the disclosure of which is incorporated by reference herein in its entirety.

The invention also relates to kits for detectably labeling molecules, sequencing, amplifying and synthesizing molecules by well known techniques. See U.S. Pat. Nos. 4,962,020, 5,173,411, 4,795,699, 5,498,523, 5,405,776 and 5,244,797. Such kits may comprise a carrying means being compartmentalized to receive in close confinement one or more container means such as vials, test tubes and the like. Each of such container means comprises components or a mixture of components needed to perform nucleic acid synthesis, sequencing, labeling, or amplification.

A kit for sequencing DNA may comprise a number of container means. Such a kit may comprise one or more of the polymerases of the invention, one or a number of types of nucleotides needed to synthesize a DNA molecule complementary to DNA template, one or a number of different types of terminators (such as dideoxynucleoside triphosphates), a pyrophosphatase, one or a number of primers and/or a suitable sequencing buffer (or combinations of such components).

A kit used for amplifying or synthesizing of nucleic acids will comprise, one or more polymerases of the invention, and one or a number of nucleotides or mixtures of nucleotides. Various primers may be included in a kit as well as a suitable amplification or synthesis buffers.

When desired, the kit of the present invention may also include container means which comprise detectably labeled nucleotides which may be used during the synthesis or sequencing of a nucleic acid molecule. One of a number of labels may be used to detect such nucleotides. Illustrative labels include, but are not limited to, radioactive isotopes, fluorescent labels, chemiluminescent labels, bioluminescent labels and enzyme labels.

Use of the Methods and Kits

The polymeraes, methods and kits embodied in the present invention will have general utility in any application utilizing nucleic acid amplification methodologies, particularly those directed to the analysis and typing of polymorphic or minisatellite DNA fragments, and most particularly those directed to the analysis and typing of minisatellite, microsatellite and STR DNA fragments. Amplification techniques in which the present methods may be used include PCR (U.S. Pat. Nos. 4,683,195 and 4,683,202), Strand Displacement Amplification (SDA; U.S. Pat. No. 5,455,166; EP 0 684 315), and Nucleic Acid Sequence-Based Amplification (NASBA; U.S. Pat. No. 5,409,818; EP 0 329 822). Nucleic acid analysis and typing techniques which may employ the present compositions include nucleic acid sequencing methods such as those disclosed in U.S. Pat. Nos. 4,962,022 and 5,498,523, as well as more complex PCR-based nucleic acid fingerprinting techniques such as Random Amplified Polymorphic DNA (RAPD) analysis (Williams, J. G. K., et al., *Nucl. Acids Res.* 18(22): 6531–6535, 1990), Arbitrarily Primed PCR (AP-PCR; Welsh, J., and McClelland, M., *Nucl. Acids Res.* 18(24): 7213–7218, 1990), DNA Amplification Fingerprinting (DAF; Caetano-Anollés et al., *Bio/Technology* 9:553–557, 1991), and microsatellite PCR or Directed Amplification of Minisatellite-region DNA (DAMD; Heath, D. D., et al., *Nucl. Acids Res.* 21(24): 5782–5785, 1993). In particular, the polymerases, methods and kits of the present invention will be useful in the fields of medical genetics, therapeutics and diagnostics, forensics (particularly identity and paternity testing), and agricultural (e.g. plant breeding) and other biological sciences, in any procedure utilizing DNA polymerases for analysis and typing of polymorphic, minisatellite, microsatellite or STR DNA fragments. Particularly suitable for diagnosis by the methods of the present invention are genetic diseases such as cystic fibrosis, hemophilia, Alzheimer's disease, schizophrenia, muscular dystrophy or multiple sclerosis. Together, these abilities will assist medical professionals and patients in diagnostic and prognostic determinations as well as in the development of treatment and prevention regimens for these and other disorders.

It will also be apparent to one of ordinary skill in the art that the present methods may be used to screen animal tissues to be subsequently used in medical procedures such as tissue or organ transplants, blood transfusions, zygote implantations and artificial inseminations. In such procedures, pre-screening of the subject tissues for the presence of particular polymorphic DNA fragments may improve the success of tissue or organ transplants (by decreasing the likelihood of rejection due to donor-recipient genetic incompatibility) and of zygote implantations (by eliminating the use of genetically defective zygotes). Similarly, use of these methods will reduce the chances of transmission of infectious diseases (e.g., hepatitis and AIDS) in medical procedures that are often prone to such transmission, such as blood transfusions and artificial insemination. Finally, use of the present invention for identification of unique polymorphic, minisatellite, microsatellite and STR DNA fragments will assist in forensic science in such applications as crime-scene analysis of blood, tissue and body secretions containing small amounts of DNA, as well as in paternity testing.

It will be readily apparent to those skilled in the relevant arts that other suitable modifications and adaptations to the methods and applications described herein are obvious and may be made without departing from the scope of the invention or any embodiment thereof. Having now described the present invention in detail, the same will be more clearly understood by reference to the following examples, which are included herewith for purposes of illustration only and are not intended to be limiting of the invention.

EXAMPLE 1

Bacterial Strains And Growth Conditions

*Thermotoga neapolitana* DSM No. 5068 was grown under anaerobic conditions as described in the DSM catalog (addition of resazurin, $Na_2S$, and sulfur granules while sparging the media with nitrogen) at 85° C. in an oil bath from 12 to 24 hours. The cells were harvested by filtering the broth through Whatman #1 filter paper. The supernatant was collected in an ice bath and then centrifuged in a refrigerated centrifuge at 8,000 rpms for twenty minutes. The cell paste was stored at −70° C. prior to total genomic DNA isolation.

*E. coli* strains were grown in 2×LB broth base (Lennox L broth base: GIBCO/BRL) medium. Transformed cells were incubated in SOC (2% tryptone, 0.5% yeast extract, yeast 10 mM NaCl, 2.5 mM KCl, 20 mM glucose, 10 mM $MgCl_2$, and 10 mM $MgSO_4$ per liter) before plating. When appropriate antibiotic supplements were 20 mg/l tetracycline and 100 mg/l ampicillin. *E. coli* strain DH10B (Lorow et al., *Focus* 12:19–20 (1990)) was used as host strain. Competent DH10B may be obtained from Life Technologies, Inc. (LTI) (Rockville, Md.).

EXAMPLE 2

DNA Isolation

*Thermotoga neapolitana* chromosomal DNA was isolated from 1.1 g of cells by suspending the cells in 2.5 ml TNE (50 mM Tris-HCl, pH 8.0, 50 mM NaCl, 10 mM EDTA) and treated with 1% SDS for 10 minutes at 37° C. DNA was extracted with phenol by gently rocking the lysed cells overnight at 4° C. The next day, the lysed cells were extracted with chloroform:isoamyl alcohol. The resulting chromosomal DNA was further purified by centrifigation in a CsCl density gradient. Chromosomal DNA isolated from the density gradient was extracted three times with isopropanol and dialyzed overnight against a buffer containing 10 mM Tris-HCl (pH 8.0) and 1 mM EDTA (TE).

EXAMPLE 3

Construction of Genomic Libraries

The chromosomal DNA isolated in Example 2 was used to construct a genomic library in the plasmid pCP13. Briefly, 10 tubes each containing 10 µg of *Thermotoga neapolitana* chromosomal DNA was digested with 0.01 to 10 units of SauIIIAl for 1 hour at 37° C. A portion of the digested DNA was tested in an agarose (1.2%) gel to determine the extent of digestion. Samples with less than 50% digestion were pooled, ethanol precipitated and dissolved in TE. 6.5 µg of partially digested chromosomal DNA was ligated into 1.5 µg of pCP13 cosmid which had been digested with BamHI restriction endonuclease and dephosphorylated with calf intestinal alkaline phosphatase. Ligation of the partially digested Thermotoga DNA and BamHI cleaved pCP13 was carried out with T4 DNA ligase at 22° C. for 16 hours. After ligation, about 1 µg of ligated DNA was packaged using λ-packaging extract (obtained from Life Technologies, Inc., Rockville, Md.). DH10B cells (Life Tech. Inc.) were then infected with 100 µl of the packaged material. The infected cells were plated on tetracycline containing plates. Serial dilutions were made so that approximately 200 to 300 tetracycline resistant colonies were obtained per plate.

EXAMPLE 4
Screening for Clones Expressing *Thermotoga neapolitana* DNA Polymerase Identification of the *Thermotoga neapolitana* DNA polymerase gene of the invention was cloned using the method of Sagner et al., *Gene* 97:119–123 (1991) which reference is herein incorporated in its entirety. Briefly, the *E. coli* tetracycline resistant colonies from Example 3 were transferred to nitrocellulose membranes and allowed to grow for 12 hours. The cells were then lysed with the fumes of chloroform:toluene (1:1) for 20 minutes and dried for 10 minutes at room temperature. The membranes were then treated at 95° C. for 5 minutes to inactivate the endogenous *E. coli* enzymes. Surviving DNA polymerase activity was detected by submerging the membranes in 15 ml of polymerase reaction mix (50 mM Tris-HCl (pH 8.8), 1 mM $MgCl_2$, 3 mM β-mercaptoethanol, 10 μM DCTP, dGTP, dTTP, and 15 μCi of 3,000 Ci/mmol [α]PdATP) for 30 minutes at 65° C.

Using autoradiography, three colonies were identified that expressed a *Thermotoga neapolitana* DNA polymerase. The cells were grown in liquid culture and the protein extract was made by sonication. The presence of the cloned thermostable polymerase was confirmed by treatment at 90° C. followed by measurement of DNA polymerase activity at 72° C. by incorporation of radioactive deoxyribonucleoside triphosphates into acid insoluble DNA. One of the clones, expressing Tne DNA polymerase, contained a plasmid designated pCP13-32 and was used for further study.

EXAMPLE 5
Subcloning of Tne DNA polymerase

Since the pCP13-32 clone expressing the Tne DNA polymerase gene contains about 25 kb of *T. neapolitana* DNA, subcloning a smaller fragment of the Tne polymerase gene was attempted. The molecular weight of the Tne DNA polymerase purified from *E. coli*/pCP13-32 was about 100 kd. Therefore, a 2.5–3.0 kb DNA fragment will be sufficient to code for full-length polymerase. A second round of Sau3A partial digestion similar to Example 3 was done using pCP13-32 DNA. In this case, a 3.5 kb region was cut out from the agarose gel, purified by Gene Clean (BIO 101, La Jolla, Calif.) and ligated into plasmid pSport 1 (Life Technologies, Inc.) which had been linearized with BamHI and dephosphorylated with calfintestinal alkaline phosphatase. After ligation, DH10B was transformed and colonies were tested for DNA polymerase activity as described in Example 1. Several clones were identified that expressed Tne DNA polymerase. One of the clones (pSport-Tne) containing about 3 kb insert was further characterized. A restriction map of the DNA fragment is shown in FIG. 1. Further, a 2.7 Kb HindIII-SstI fragment was subcloned into pUC19 to generate pUC19-Tne. *E. coli*/pUC19-Tne also produced Tne DNA polymerase. *E. coli* DH10B (pUC19-Tne) was deposited on Sep. 30, 1994 with the Collection, Agricultural Research Culture Collection (NRRL), 1815 Peoria, Ill. 61604 as Deposit No. NRRL B-21338. The nucleotide and amino acid sequence of Tne polymerase is described in U.S. application Ser. Nos. 08/706,702 and 08/706,706 filed Sep. 9, 1996, both of which are incorporated by reference herein.

EXAMPLE 6
Purification of *Thermotoga neapolitana* DNA Polymerase from *E. coli*

Twelve grams of *E. coli* cells expressing cloned Tne DNA polymerase (DH10B/pSport-Tne) were lysed by sonication (four thirty-second bursts with a medium tip at the setting of nine with a Heat Systems Ultrasonics Inc., model 375 sonicator) in 20 ml of ice cold extraction buffer (50 mM Tris HCl (pH 7.4), 8% glycerol, 5 mM mercaptoethanol, 10 mM NaCl, 1 mM EDTA, 0.5 mM PMSF). The sonicated extract was heated at 80° C. for 15 min. and then cooled in ice for 5 min. 50 mM KCl and PEI (0.4%) was added to remove nucleic acids. The extract was centrifuged for clarification. Ammonium sulfate was added to 60%, the pellet was collected by centrifugation and resuspended in 10 ml of column buffer (25 mM Tris-HCl (pH 7.4), 8% glycerol, 0.5% EDTA, 5 mM 2-mercaptoethanol, 10 mM KCl). A Blue-Sepharose (Pharmacia) column, or preferably a Toso heparin (Tosohaas) column, was washed with 7 column volumes of column buffer and eluted with a 15 column volume gradient of buffer from 10 mM to 2 M KCl. Fractions containing polymerase activity were pooled. The fractions were dialyzed against 20 volumes of column buffer. The pooled fractions were applied to a Toso650Q column (Tosohaas). The column was washed to baseline $OD_{280}$ and elution effected with a linear 10 column volume gradient of 25 mM Tris (pH 7.4), 8% glycerol, 0.5 mM EDTA, 10 mM KCl, 5 mM β-mercaptoethanol to the same buffer plus 650 mM KCl. Active fractions were pooled.

EXAMPLE 7
Construction of *Thermotoga neapolitana* 3'-to-5'Exonuclease Mutant The amino acid sequence of portions of the Tne DNA polymerase was compared with other known DNA polymerases such as *E. coli* DNA polymerase 1, Taq DNA polymerase, T5 DNA polymerase, and T7 DNA polymerase to localize the regions of 3'-to-5' exonuclease activity, and the dNTP binding domains within the DNA polymerase. One of the 3'-to-5' exonuclease domains was determined based on the comparison of the amino acid sequences of various DNA polymerases (Blanco, L., et al. *Gene* 112: 139–144 (1992); Braithwaite and Ito, *Nucleic Acids Res.* 21: 787–802 (1993)) is as follows:

| Tne | 318 | PSFALDLETSS | 328 | (SEQ ID NO:18) |
|---|---|---|---|---|
| Pol I | 350 | PVFAFDTETDS | 360 | (SEQ ID NO:19) |
| T5 | 159 | GPVAFDSETSA | 169 | (SEQ ID NO:20) |
| T7 | 1 | MIVSDIEANA | 10 | (SEQ ID NO:21) |

As a first step to make the Tne DNA polymerase devoid of 3'→5' exonuclease activity, a 2 kb Sph fragment from pSport-Tne was cloned into M13mp19 (LTI, Rockville, Md.). The recombinant clone was selected in *E. coli* DH5αF'IQ (LTI, Rockville, Md.). One of the clones with the proper insert was used to isolate uracilated single-stranded DNA by infecting *E. coil* CJ236 (Biorad, Calif.) with the phage particle obtained from *E. coli* DH5αF'IQ. An oligonucleotide, GA CGT TTC AAG CGC TAG GGC AAA AGA (SEQ ID NO:22) was used to perform site directed mutagenesis. This site-directed mutagenesis converted $Asp^{323}$ (indicated as * above) to $Ala^{323}$. An Eco47III restriction site was created as part of this mutagenesis to facilitate screening of the mutant following mutagenesis. The mutagenesis was performed using a protocol as described in the Biorad manual (1987) except T7 DNA polymerase was used instead of T4 DNA polymerase (USB, Cleveland, Ohio). The mutant clones were screened for the Eco47III restriction site that was created in the mutagenic oligonucleotide. One of the mutants having the created Eco47III restriction site was used for further study. The mutation $Asp^{323}$ to $Ala^{323}$ was confirmed by DNA sequencing.

Figure 2A:
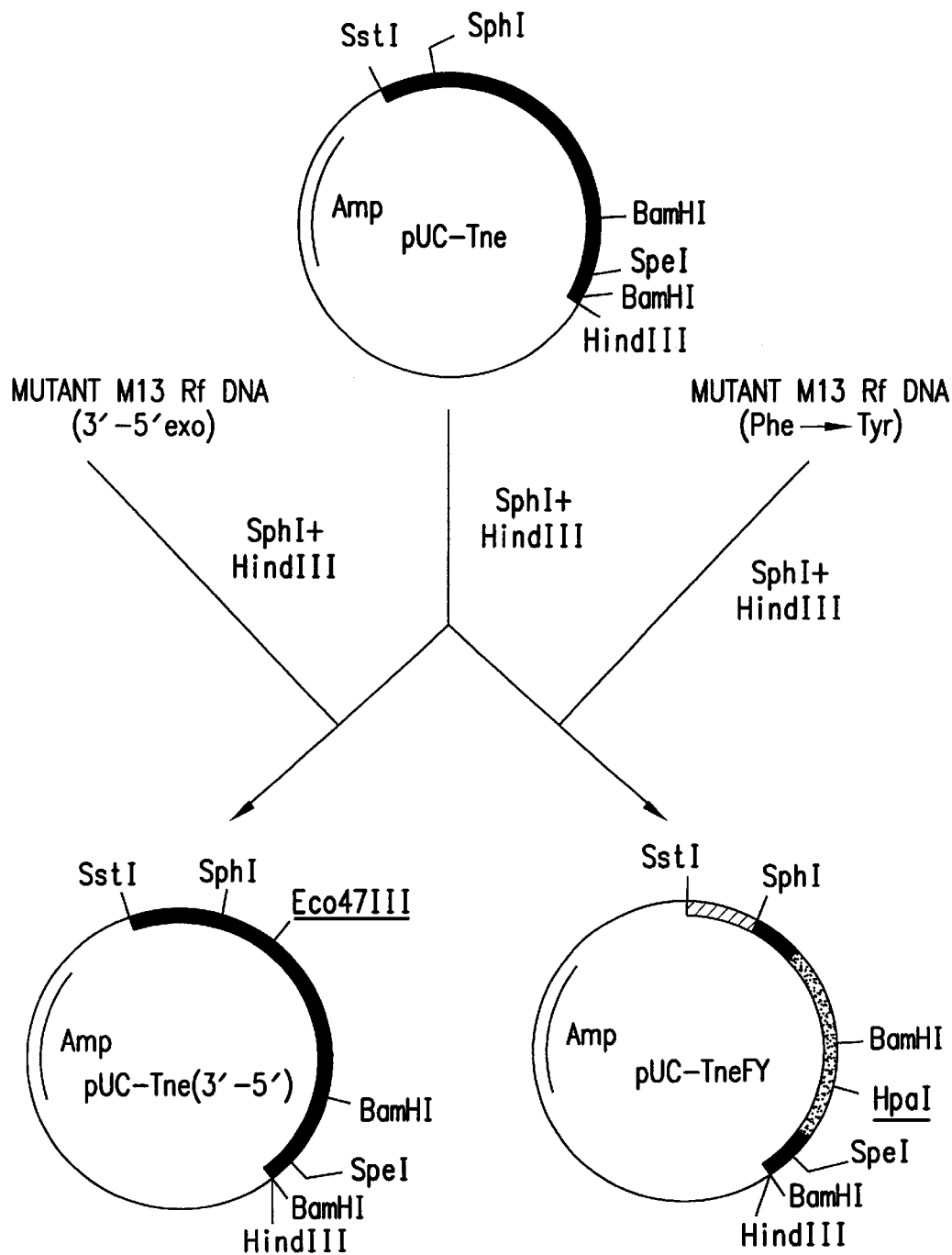
FIG. 2A schematically depicts the construction of plasmids pUC-Tne (3'→5') and pUC-Tne FY.

To incorporate the 3'→5' exonuclease mutation in an expression vector, the mutant phage was digested with SphI and HindIII. A 2 kb fragment containing the mutation was isolated. This fragment was cloned in pUC-Tne to replace the wild type fragment. See FIG. 2A. The desired clone, pUC-Tne (3'→5'), was isolated. The presence of the mutant sequence was confirmed by the presence of the unique Eco47III site. The plasmid was then digested with SstI and HindIII. The entire mutant polymerase gene (2.6 kb) was purified and cloned into SstI and HindIII digested pTrc99 expression vector (Pharmacia, Sweden). The clones were selected in DH10B (LT, Rockville, Md.). The resulting plasmid was designated pTrcTne35. See FIG. 2B. This clone produced active heat stable DNA polymerase.

EXAMPLE 8
Phenylalanine to Tyrosine Mutant

The polymerase active site including the dNTP binding domain is usually present at the carboxyl terminal region of the polymerase. The sequence of the Tne polymerase gene suggests that the amino acids that presumably contact and interact with the dNTPs are present within the 694 bases starting at the internal BamHI site. See FIG. 1. This conclusion is based on homology with a prototype polymerase E. coli DNA polymerase I. See Polisky et al., *J. Biol. Chem.* 265:14579–14591 (1990). A comparison was made of the O-helix for various polymerases:

| Tne   | 722 | RRVGKMVNFSIIYG | 735 | (SEQ ID NO:12) |
|-------|-----|----------------|-----|----------------|
| Pol I | 754 | RRSAKAINFGLIYG | 767 | (SEQ ID NO:13) |
| T5    | 562 | RQAAKAITFGILYG | 575 | (SEQ ID NO:14) |
| T7    | 518 | RDNAKTFIYGFLYG | 531 | (SEQ ID NO:15) |
| Taq   | 659 | RRAAKTINFGVLYG | 672 | (SEQ ID NO:16) |

In order to change $Phe^{730}$ of the Tne polymerase to a $Tyr^{730}$ site directed mutagenesis was performed using the oligonucleotide GTA TAT TAT AGA GTA GTT AAC CAT CTT TCC A (SEQ ID NO:23). As part of this oligonucleotide directed mutagenesis, a HpaI restriction site was created in order to screen mutants easily. The same uracilated single-stranded DNA and mutagenesis procedure described in Example 7 were used for this mutagenesis. Following mutagenesis, the mutants were screened for the HpaI site. Mutants with the desired HpaI site were used for further study. The mutation was confirmed by DNA sequencing.

Figure 2B:
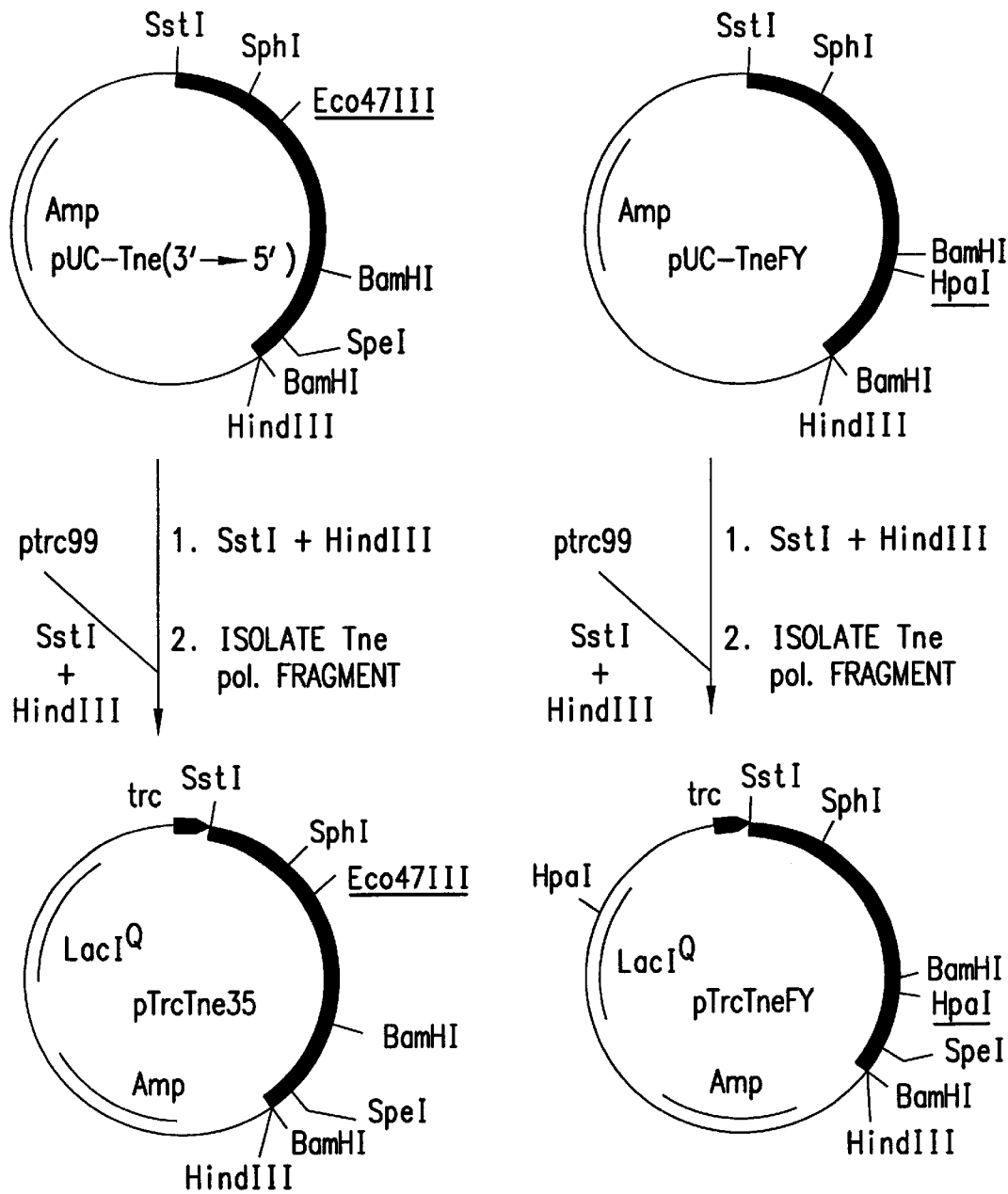
FIG. 2B schematically depicts the construction of plasmids pTrcTne35 and pTrcTne FY.

The $Phe^{730}$ to $Tyr^{730}$ mutation was incorporated into pUC-Tne by replacing the wild type SphI-HindIII fragment with the mutant fragment obtained from the mutant phage DNA. The presence of the desired clone, pUC-TneFY, was confirmed by the presence of the unique HpaI site, see FIG. 2A. The entire mutant polymerase gene was subcloned into pTrc99 as an SstI-HindIII fragment as described above in DH10B. The resulting plasmid was designated pTrcTneFY. (FIG. 2B). The clone produced active heat stable polymerase.

EXAMPLE 9
3'→5' Exonuclease and $Phe^{730}$→$Tyr^{730}$ Double Mutants

Figure 3:
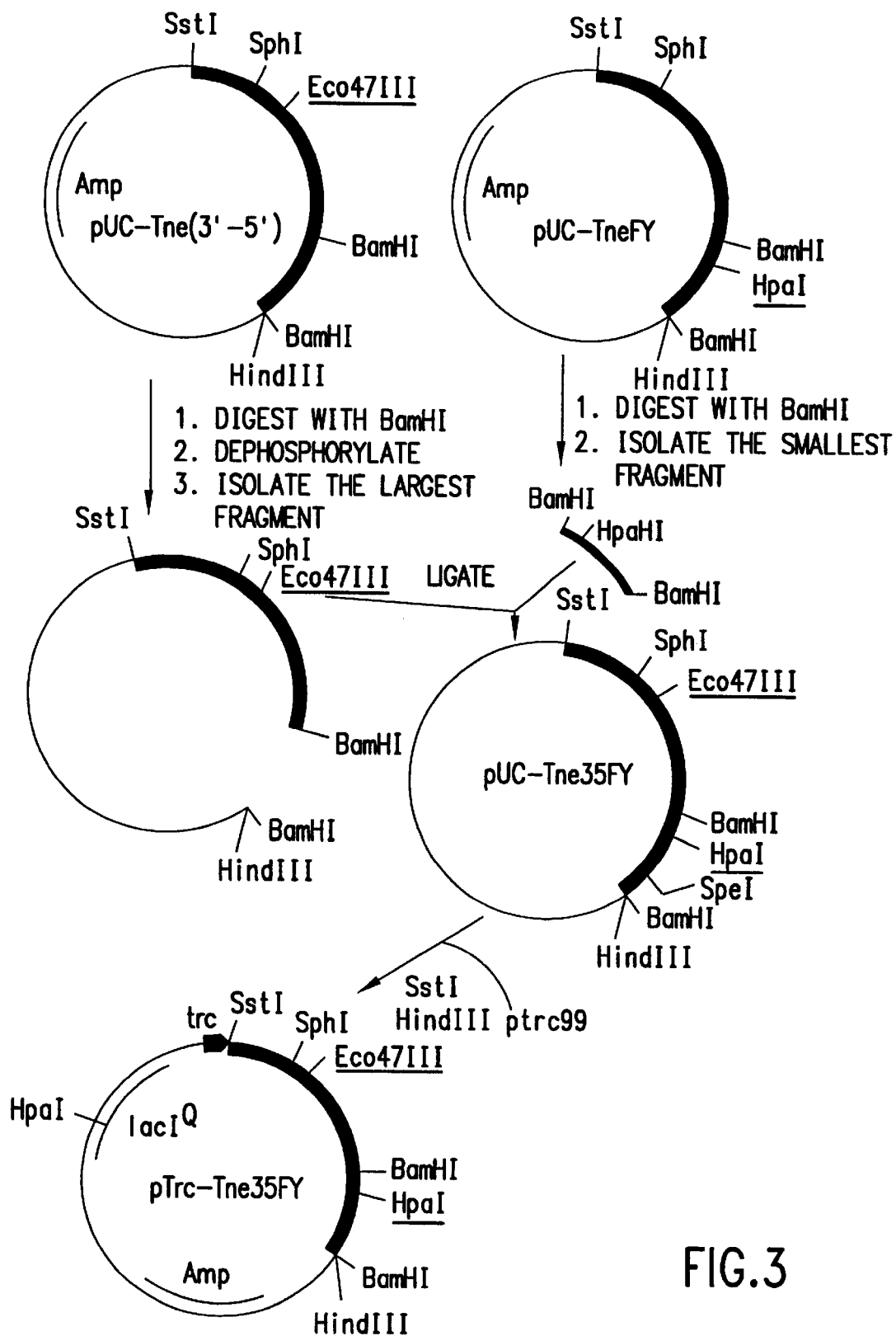
FIG. 3 schematically depicts the construction of plasmid pTrcTne35 FY.

In order to introduce the 3'→5' exonuclease mutation and the $Phe^{730}$→$Tyr^{730}$ mutation in the same expression vector, pTrc99, it was necessary to first reconstitute both mutations in the pUC-Tne clone. See FIG. 3. Both the pUC-Tne (3'→5') and the pUC-TneFY were digested with BamHI. The digested pUC-Tne (3'→5') was dephosphorylated to avoid recirculation in the following ligations. The resulting fragments were purified on a 1% agarose gel. The largest BamHI fragment (4.4 kb) was purified from pUC-Tne (3'-+5') digested DNA and the smallest Bam-HI fragment (0.8 kb) containing the $Phe^{730}$→$Tyr^{730}$ mutation was purified and ligated to generate pUC-Tne35FY. The proper orientation and the presence of both mutations in the same plasmid was confirmed by Eco47III, HpaI, and SphI-HindIII restriction digests. See FIG. 3.

The entire polymerase containing both mutations was subcloned as a SstI-HindIII fragment in pTrc99 to generate pTrcTne35FY in DH10B. The clone produced active heat stable polymerase.

Figure 4:
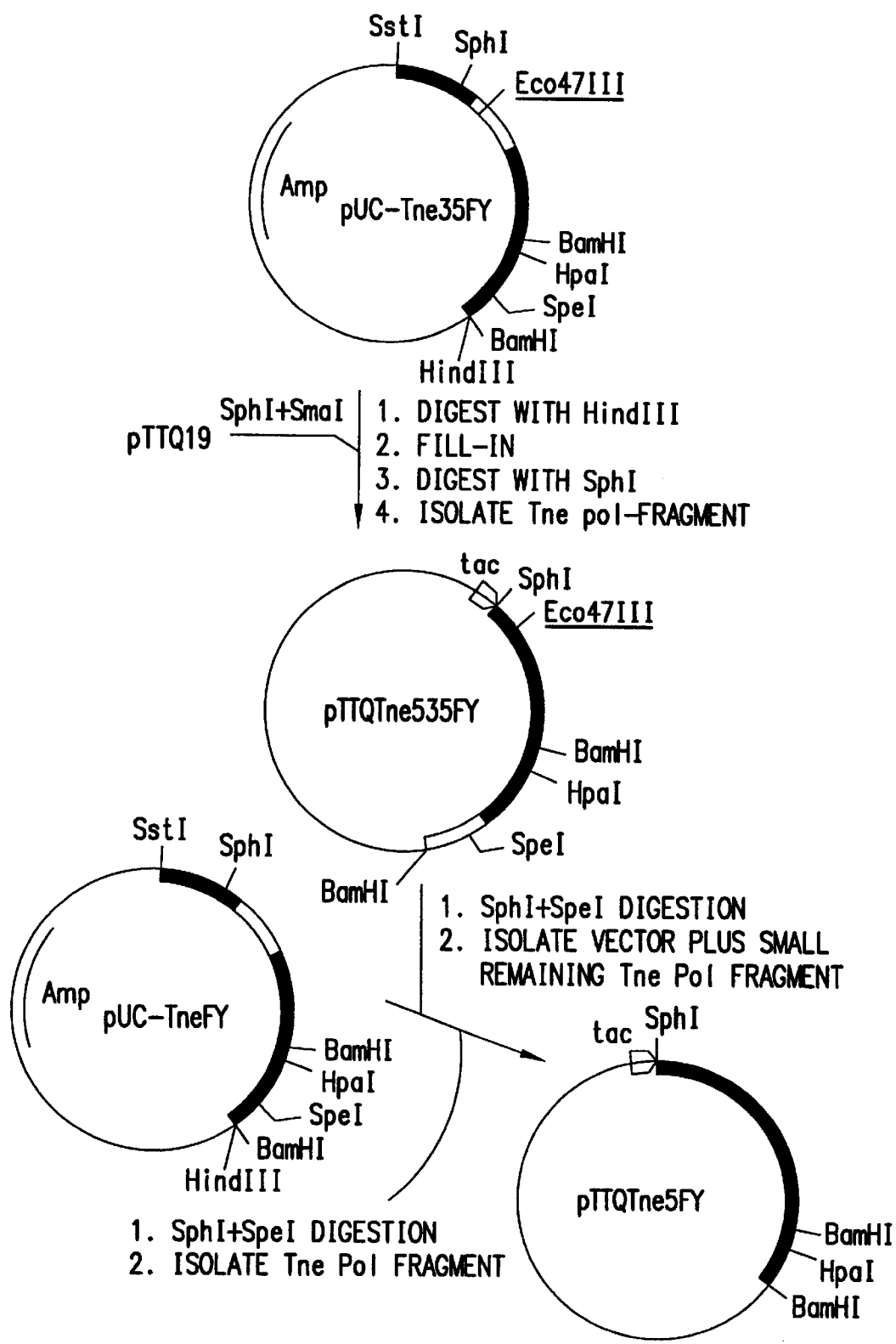
FIG. 4 schematically depicts the construction of plasmids pTTQTne5FY and pTTQTne535FY.

EXAMPLE 10
3'→5' Exonuclease, 5'→3' Exonuclease, and $Phe^{730}$→$Tyr^{730}$ Triple Mutants In most of the known polymerases, the 5'-to-3' exonuclease activity is present at the amino terminal region of the polymerase (Ollis, D. L., et al., *Nature* 313, 762–766, 1985; Freemont, P. S., et al., *Proteins* 1, 66–73, 1986; Joyce, C. M., *Curr. Opin. Struct. Biol.* 1: 123–129 (1991). There are some conserved amino acids that are implicated to be responsible for 5'-to-3' exonuclease activity (Gutman and Minton, *Nucl. Acids Res.* 21, 4406–4407, 1993). See supra. It is known that 5'-to-3' exonuclease domain is dispensable. The best known example is the Klenow fragment of E. coli Pol I. The Klenow fragment is a natural proteolytic fragment devoid of 5'-to-3' exonuclease activity (Joyce, C. M., et al., *J. Biol. Chem.* 257, 1958–1964, 1990). In order to generate an equivalent mutant for Tne DNA polymerase devoid of 5'-to-3' exonuclease activity, the presence of a unique SphI site present 680 bases from the SstI site was exploited. pUC-Tne35FY was digested with HindIII, filled-in with Klenow fragment to generate a blunt-end, and digested with SphI. The 1.9 kb fragment was cloned into an expression vector pTTQ19 (Stark, M. J. R., *Gene* 51, 255–267, 1987) at the SphI-SmaI sites and was introduced into DH10B. This cloning strategy generated an in-frame polymerase clone with an initiation codon for methionine from the vector. The resulting clone is devoid of 219 amino terminal amino acids of Tne DNA polymerase. This clone is designated as pTTQTne535FY (FIG. 4). The clone produced active heat stable polymerase. No exonuclease activity could be detected in the mutant polymerase as evidenced by lack of presence of unusual sequence ladders in the sequencing reaction. This particular mutant polymerase is highly suitable for DNA sequencing.

EXAMPLE 11
5'→3' Exonuclease Deletion and $Phe^{730}$→$Tyr^{730}$ Substitution Mutant In order to generate the 5'-to-3' exonuclease deletion mutant of the Tne DNA polymerase $Phe^{730}$→$Tyr^{730}$ mutant, the 1.8 kb SphI-SpeI fragment of pTTQTne535FY was replaced with the identical fragment of pUC-Tne FY. See FIG. 4. A resulting clone, pTTQTne5FY, produced active heat stable DNA polymerase. As measured by the rate of degradation of a labeled primer, this mutant has a modulated, low but detectable, 5'-to-3' exonuclease activity compared to wild type Tne DNA polymerase. M13/pUC Forward 23-Base Sequencing Primers™, obtainable from LTI, Rockville, Md., was labeled at the 5' end with [$P^{32}$] ATP and T4 kinase, also obtainable from LTI, Rockville, Md., as described by the manufacturer. The reaction mixtures contained 20 units of either wildtype or mutant Tne DNA polymerase, 0.25 pmol of labeled primer, 20 mM tricine, pH 8.7, 85 mM potassium acetate, 1.2 mM magnesium acetate, and 8% glycerol. Incubation was carried out at 70° C. At various time points, 10 μl aliquots were removed to 5 μl cycle sequencing stop solution and were resolved in a 6% polyacrylamide sequencing gel followed by andoradiography. While the wildtype polymerase degraded the primer in 5 to 15 minutes, it took the mutant polymerase more than 60 minutes for the same amount of degradation of the primer.

EXAMPLE 12

Purification of the Mutant Polymerases

The purification of the mutant polymerases was done essentially as described Example 6, supra, with minor modifications. Specifically, 5 to 10 grams of cells expressing cloned mutant Tne DNA polymerase were lysed by sonication with a Heat Systems Ultrasonic, Inc. Model 375 machine in a sonication buffer comprising 50 mM Tris-HCl (pH 7.4); 8% glycerol; 5 mM 2-mercaptoethanol, 10 mM NaCl, 1 mM EDTA, and 0.5 mM PMSF. The sonication sample was heated at 75° C. for 15 minutes. Following heat treatment, 200 mM NaCl and 0.4% PEI was added to remove nucleic acids. The extract was centrifuged for clarification. Ammonium sulfate was added to 48%, the pellet was resuspended in a column buffer consisting of 25 mM Tris-HCl (pH 7.4); 8% glycerol; 0.5% EDTA; 5 mM 2-mercaptoethanol; 10 mM KCl and loaded on a heparin agarose (LTI) column. The column was washed with 10 column volumes using the loading buffer and eluted with a 10 column volume buffer gradient from 10 mM to 1 M KCl. Fractions containing polymerase activity were pooled and dialyzed in column buffer as above with the pH adjusted to 7.8. The dialyzed pool of fractions were loaded onto a MonoQ (Pharmacia) column. The column was washed and eluted as described above for the heparin column. The active fractions are pooled and a unit assay was performed.

The unit assay reaction mixture contained 25 mM TAPS (pH 9.3), 2 mM $MgCl_2$, 50 mM KCl, 1 mM DTT, 0.2 mM dNTPs, 500 µg/ml DNAse I treated salmon sperm DNA, 21 mCi/ml [$\alpha P^{32}$] dCTP and various amounts of polymerase in a final volume of 50 µl. After 10 minutes incubation at 70° C., 10 µl of 0.5 M EDTA was added to the tube. TCA perceptible counts were measured in GF/C filters using 40 µl of the reaction mixture.

EXAMPLE 13

Generation of 5'-to-3' exonuclease mutant of full length Tne DNA polymerase

1. Identification of Two Amino Acids Responsible for 5'-to-3' Exonuclease Activity Tne DNA polymerase contains three enzymatic activities similar to *E. coil* DNA polymerase I: 5'-to-3' DNA polymerase activity, 3'-to-5' exonuclease activity and 5'-to-3' exonuclease activity. This example is directed to the elimination of the 5'-to-3' exonuclease activity in full length Tne DNA polymerase. Gutman and Minton (*Nucleic Acids Res.* 1993, 21, 4406–4407) identified six (A–F) conserved 5'-to-3' exonuclease domains containing a total of 10 carboxylates in various DNA polymerases in the polI family. Seven out of 10 carboxylates (in domains A, D and E) have been implicated to be involved in divalent metal ions binding as judged from the crystal structure (Kim et al. *Nature*, 1995, 376, 612–616) of Taq DNA polymerase. However, there was no clear demonstration that these carboxylates are actually involved 5'-to-3' exonuclease activity. In order to find out the biochemical characteristics of some of these carboxylates, two of the aspartic acids in domains A and E were chosen for mutagenesis. The following aspartic acids in these two domains were identified:

Tne DNA polymerase: 5 FLFD$^8$GT 10 (domain A) (SEQ ID NO:24)

Taq DNA polymerase: 15 LLVD$^{18}$GH 20 (SEQ ID NO:25) and

Tne DNA polymerase: 132 SLITGD$^{137}$KDML141 (domain E) (SEQ ID NO:26)

Taq DNA polymerase: 137 RILTAD$^{142}$KDLY146 (SEQ ID NO:27)

2. Isolation of Single Stranded DNA for Mutagenesis

Single stranded DNA was isolated from pSportTne (see infra). pSportTne was introduced into DH5αF'IQ (LT, Rockville, Md.) by transformation. A single colony was grown in 2 ml Circle Grow (Bio 101, California) medium with ampicillin at 37° C. for 16 hrs. A 10 ml fresh media was inoculated with 0.1 ml of the culture and grown at 37° C. until the A590 reached approximately 0.5. At that time, 0.1 ml of M13KO7 helper phage ($1\times10^{11}$ pfu/ml, LTI) was added to the culture. The infected culture was grown for 75 min. Kanamycin was then added at 50 µg/ml, and the culture was grown overnight (16 hrs.). The culture was spun down. 9 ml of the supernatant was treated with 50 µg each of RNaseA and DNaseI in the presence of 10 mM $MgCl_2$ for 30 min. at room temperature. To this mixture, 0.25 volume of a cocktail of 3M ammonium acetate plus 20% polyethylene glycol was added and incubated for 20 min. on ice to precipitate phage. The phage was recovered by centrifugation. The phage pellet was dissolved in 200 µl of TE (10 mM Tris-HCl (pH 8) and 1 mM EDTA). The phage solution was extracted twice with equal volume of buffer saturated phenol (LTI, Rockville, Md.), twice with equal volume of phenol:chloroform:isoamyl alcohol mixture (25:24:1, LTI, Rockville, Md.) and finally, twice with chloroform:isoamyl alcohol (24:1). To the aqueous layer, 0.1 volume of 7.5 M ammonium acetate and 2.5 volume of ethanol were added and incubated for 15 min. at room temperature to precipitate single stranded DNA. The DNA was recovered by centrifigation and suspended in 200 µl TE.

3. Mutagenesis of $D^8$ and $D^{137}$

Two oligos were designed to mutagenize $D^8$ and $D^{137}$ to alanine. The oligos are: 5' GTAGGCCAGGGCTGT GCCGGCAAAGAGAAATAGTC 3' (D8A) (SEQ ID NO:28) and 5' GAAGCATATCCTTGGCGCCGGTTAT TATGAAAATC 3' (D137A) (SEQ ID NO:29). In the D8A oligo a NgoAIV (bold underlined) and in the oligo D137A a KasI (bold underlined) site was created for easy identification of clones following mutagenesis. 200 pmol of each oligo was kinased according to the Muta-gene protocol (Bio-Rad, California) using 5 units of T4 Kinase (LTI, Rockville, Md.). 200 ng of single stranded DNA was annealed with 2 pmol of oligo according to the Muta-gene protocol. The reaction volume was 10 µl. Following the annealing step, complementary DNA synthesis and ligation was carried out using 5 units of wildtype T7 DNA polymerase (USB, Ohio) and 0.5 unit T4 ligase (LTI). 1 µl of the reaction was used to transform a MutS *E. coli* (obtainable from Dr. Paul Modrich at the Duke University, N.C.) and selected in agar plates containing ampicillin. A control annealing and synthesis reaction was carried out without addition of any oligo to determine the background. There were 50–60 fold more colonies in the transformation plates with the oligos than without any oligo. Six colonies from each mutagenic oligo directed synthesis were grown and checked for respective restriction site (NgoAIV or KasI). For D8A (NgoAIV), 4 out of 6 generated two fragments (3 kb and 4.1 kb). Since pSportTne has an NgoAIV site near the f1 intergenic region, the new NgoAIV site within the Tne DNA polymerase produced the expected fragments. The plasmid was designated as pSportTne NgoAIV. For D137A (KasI), 5 out of 6 clones produced two expected fragments of 1.1 kb and 6 kb in size. Since pSportTne has another KasI site, the newly created KasI site generated these two expected fragments. The plasmid was designated as pSportTneKasI. Both D8A and D137A mutations were confirmed by DNA sequencing.

4. Reconstruction of the Mutant Polymerase into Expression Vector

During the course of expression of Tne DNA polymerase or mutant Tne DNA polymerase, a variety of clones were constructed. One such clone was designated as pTTQ Tne SeqS 1. This plasmid was constructed as follows: first, similar to above mutagenesis technique glycine 195 was changed to an aspartic acid in pSportTne. A mutation in the corresponding amino acid in *E. coli* DNA polymeraseI (polA214, domain F) was found to have lost the 5'-to-3' exonuclease activity (Gutman and Minton, see above). An SspI site was created in the mutant polymerase. Second, a 650 bp SstI-SphI fragment containing the G195D mutation was subcloned in pUCTne35FY (see infra) to replace the wild type fragment. This plasmid was called pUCTne3022. Finally, the entire mutant Tne DNA polymerase was subcloned from pUCTne3022 into pTTQ18 as SstI-HindIII fragment to generate pTTQTneSeqS1. To introduce the mutation D8A or D137A in this expression vector, the 650 bp SstI-SphI was replaced with the same SstI-SphI fragment from pSportTne NgoAIV or pSportTneKasI. The plasmids were designated as pTTQTne Ngo(D8A) and pTTQTneKas (D137A), respectively.

5. Confirmation of the Mutations by DNA Sequencing

DNA sequencing of both mutant polymerases confirmed the presence of the restriction site NgoAIV as well as the mutation D8A; and KasI site as well as the mutation D137A. Also confirmed by DNA sequencing was the presence of the mutation D323A and the Eco47III restriction site in the 3'-to-5' exonuclease region. In addition, confirmed by DNA sequencing was the F730Y mutation and the HpaI restriction site in the O-helix region of the mutant Tne DNA polymerase.

6. 5'-to-3' exonuclease Activity of the Mutant Tne DNA Polymerases

The full length mutant DNA polymerase was purified as described above. The 5'-to-3' exonuclease activity was determined as described in the LTI catalog. Briefly, 1 pmol of labeled ($^{32}$P) HaeIII digested λ DNA (LTI) was used for the assay. The buffer composition is: 25 mM Tris-HCl (pH 8.3), 5 mM MgCl$_2$, 50 mM NaCl, 0.01% gelatin. The reaction was initiated by the addition of 0, 2, 4, 6 and 10 units of either wild type or mutant Tne DNA polymerase in a 50 μl reaction. The reaction mix was incubated for 1 hr at 72° C. A 10 μl aliquot was subjected to PEI-cellulose thin layer chromatography and the label released was quantitated by liquid scintillation. In this assay, both D8A and D137A mutants showed less than 0.01% label release compared to the wild type Tne DNA polymerase. The result demonstrates that in both D8A and D137A mutants the 5'-to-3' exonuclease activity has been considerably diminished. Thus, it has been confirmed that these two aspartates are involved with the 5'-to-3' exonuclease activity.

EXAMPLE 14

Generation of double mutants, R722K/F730Y, R722Q/F730Y, R722H/F730Y and R722N/F730Y of Tne DNA polymerase For all mutations, the PCR method was used. A common 5'-oligo, CAC CAG ACG GGTACC GCC ACT GGC AGG TTG (SEQ ID NO:30), was used. This oligo contains a KpnI site (shown above in bold italics). The template used for PCR was pTTQTneSeqS1 (Example 13) which already contains the F730Y mutation in the Tne polymerase gene. For the R722K/F730Y mutation, the oligo used was TAT AGA GTA GTT AAC CAT CTT TCC AAC CCG TTT CAT TTC TTC GAA CAC (SEQ ID NO:31). For the R722Q/F730Y mutation, the oligo used was TAT AGA GTA GTT AAC CAT CTT TCC AAC CCG TTG CAT TTC TTC GAA CAC (SEQ ID NO:32). For the R722N/F730Y mutation, the oligo used was TAT AGA GTA GTT AAC CAT CTT TCC AAC CCG GTT CAT TTC TTC GAA CAC (SEQ ID NO:33) and for the R722H/F730Y the oligo used was TAT AGA GTA GTTAAC CAT CTT TCC AAC CCG ATG CAT TTC TTC GAA CAC (SEQ ID NO:34). Each of these oligos contains a HpaI site (bold italics). The underlined codons were the mutated codons for arginine at the position 722 for respective amino acids. The PCR generated a 318 bp product containing a KpnI and a HpaI site. The PCR products were digested with KpnI and HpaI and cloned into pUC-TneFY digested with KpnI and HpaI to replace the original fragment to generate pUC19TneFY-R722K, pUC19TneFY-R722Q, pUC19TneFY-R722H and pUC19TneFY-R722N. Finally, the KpnI-HindIII fragment (~800 bp) of pTTQTneKasI(137A) was replaced by the 800 bp KpnI-HindIII fragment from these plasmids to generate pTne11 (R722K/F730Y), pTne10 (RL722Q/F730Y), pTne13 (R722H/F730Y) and pTne9 (R722N/F739Y), respectively. The mutations were confirmed by DNA sequencing.

EXAMPLE 15

Generation of Tne DNA Polymerase mutants F730A and F730S

F730A was constructed using PCR. The forward oligo was AAG ATG GTT AAC GCG TCT ATA ATA TAC GG (SEQ ID NO:35) which contains a HpaI site and a MluI site (bold italics). The reverse oligo was CAA GAG GCA CAG AGA GTT TCA CC (SEQ ID NO:36) which anneals downstream of SpeI present in the Tne polymnerase gene. The template used for PCR was pTTQTne KasI (D137A). The 482 bp PCR product was digested with HpaI and SpeI and cloned into pUC-TneFY thereby replacing the amino acid tyrosine at position 730 with alanine. This construct was called pUC-Tne FA.

F730 S was constructed by site directed mutagenesis. The oligo was GTA TAT TAT AGA GGA GTT AAC CAT CTT TCC (SEQ ID NO:37) where a HpaI site was created (bold italics). The single stranded DNA used was isolated from pSport-Tne that contains the double mutation D137A and D323A. This construct was designated pTne 47. The Tne polymerase gene was then cloned as an SstI and HindIII fragment into the plasmid pUC19 and the resulting clone was designated pTne101.

EXAMPLE 16

Generation of Tne DNA polymerase with a HpaI site in front of the amino acid phenylalanine at position 730.

A construct of Tne polymerase was made using PCR where a HpaI restriction enzyme site was introduced into the gene in front of the amino acid phenylalanine at position 730. The forward oligonucleotide was AAG ATG GTT AAC TTC TCT ATA ATA TAC GG(SEQ ID NO:38)which contains a HpaI site (shown above in bold italics) and the reverse oligo was the same as in Example 15 above. The template used for PCR was pTne33 which contains the Tne polymerase gene with D137A and D323A mutations cloned in pUC19. The 482 bp PCR product was digested with HpaI and SpeI and was used to replace the corresponding fragment in pTne101 (see example 15). The construct was sequenced to verify that the amino acid at position 730 was indeed phenylalanine and the plasmid was numbered pTne106.

EXAMPLE 17
Generation of Double Mutants R722Y/F730A and R722L/F730A of the Tne DNA Polymerase.

For both the mutations PCR method was used. The common 5' oligo was the same as in Example 14. For R722Y/F730A mutation the oligo used was TAT AGA GTA GTT AAC CAT CTT TCC AAC CCG GTA CAT GTC TTC GTT CAC (SEQ ID NO:39). For R722L/F730A mutation the oligo used was TAT AGA GTA GTT AAC CAT CTT TCC AAC CCG CAA CAT GT C TTC GTT CAC (SEQ ID NO:40). Each of these oligos contain a HpaI site (shown above in bold italics). The underlined codons were the mutated codons for arginine at the position 722 for respective amino acids. An AflIII site was also created (shown above in bold italics next to the underlined codon) in order to confirm the mutation. The PCR generated a 318 bp product containing aKpnI and HpaI site. The PCR products were digested with KpnI and HpaI and cloned into pUC-TneFA (see example 15). The constructs were named as pUCTneYA and pUCTneLA.

EXAMPLE 18
Generation of Tne DNA Polymerase Mutants R722Y and R722L.

The plasmid pTne 106 (see example 16) was digested with HpaI and KpnI and the 318 bp fragment was replaced with the corresponding fragment from pUCTneYA or pUCTneLA (see Example 17) to generate the mutants R722Y or R722L. In these constructs the amino acid at position 730 is the same as wild type Tne (phenylalanine). The constructs were sequenced to confirm the R722Y and the R722L mutations. The Tne DNA polymerase gene was then cloned as a SstI/HindIII fragment into the plasmid pSport1.

EXAMPLE 19
Generation of Tne DNA Polymerase Mutants R722K, R722Q and R722H.

The construct pTne 106 (see example 16) was digested with HpaI and KpnI and the 318 bp fragment was replaced with the corresponding fragment from the construct pUC19TneFY-R722K, pUC19TneFY-R722H or pTne10 (see Example 14), to generate the mutants R722K, R722H and R722Q. The constructs were sequenced to confirm the mutations. The Tne DNA polymerase gene was then subdoned into the vector pSport1 as a SstI/HindIII fragment.

EXAMPLE 20
Purification of the Mutant Tne DNA Polymerases

The purification of the mutants of Tne DNA polymerase was carried out based on the method described above with minor modifications. Two to three grams of cells expressing cloned mutant Tne DNA polymerase were resuspended in 15–20 ml of sonication buffer (50 mM Tris-HCl, pH 8.0, 10% glycerol, 5 mM 2-mercaptoethanol, 50 mM NaCl, 1 mM EDTA, and 0.5 mM PMSF and sonicated with a 550 Sonic Dismembrator (Fisher Scientific). The sonicated sample was heated at 82° C. for 20 min and then cooled in ice-water for 5 min. In the sample, 20 mM NaCl and 0.2% PEI were added and centrifuged at 13,000 rmp for 10 min. Ammonium sulfate (305 g/L) was added to the supernatant. The pellet was collected by centrifugation and resuspended in 4 ml of MonoQ column buffer (50 mM Tris-HCl, pH 8.0, 10% glycerol, 5 mM 2-mercaptoethanol, 50 mM NaCl, and 1 mM EDTA). The sample was dialyzed against one litter of MonoQ buffer overnight. Following the centrifugation at 13,000 rpm to remove any insoluble materials, the sample was loaded onto a MonoQ column (HR5/5, Pharmacia). The column was washed with MonoQ column buffer to baseline of $OD_{280}$ and then eluted with a linear gradient of 50–300 mM NaCl in 20 ml MonoQ column buffer. The fractions were analyzed by 8% SDS-PAGE and the Tne DNA polymerase activity determined as described earlier. The fractions containing active and pure Tne DNA polymerase were pooled.

EXAMPLE 21
Generadon of Taq DNA Polymerase Mutants R659K, R659H and R659Y

Figure 5:
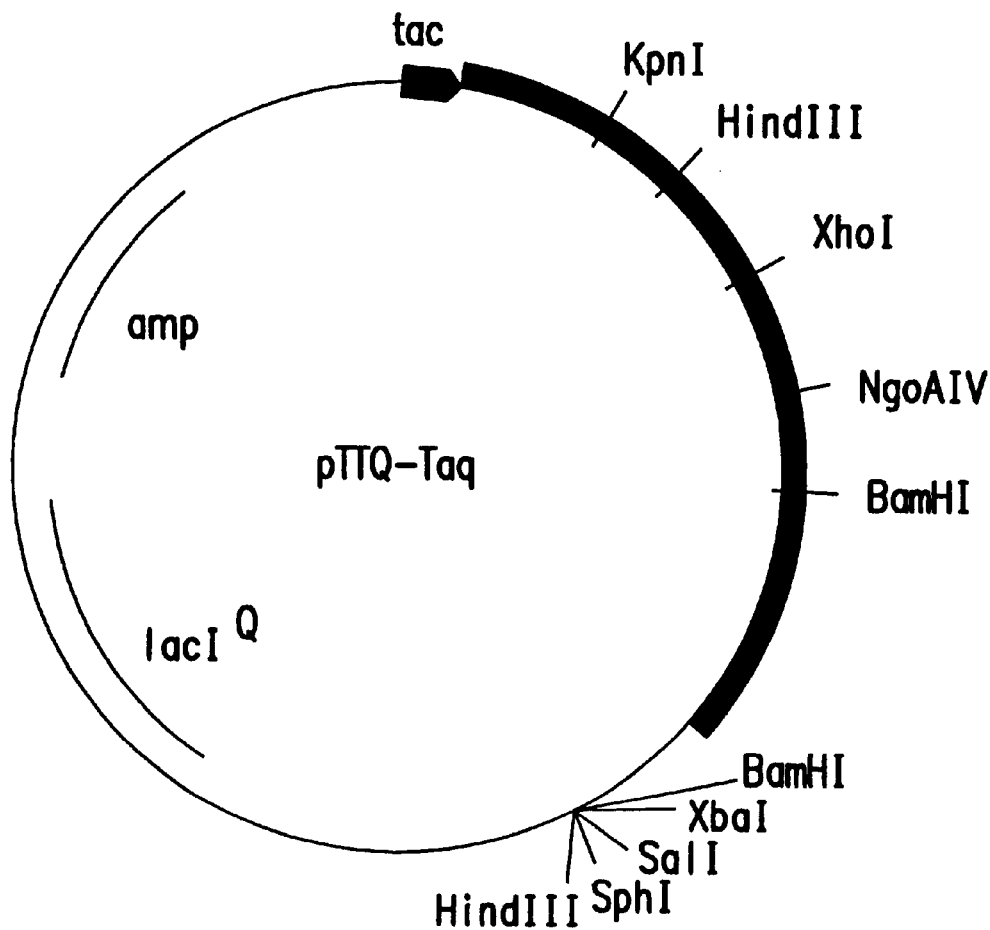
FIG. 5 depicts a plasmid containing the Taq DNA polymerase gene.
Figure 6:
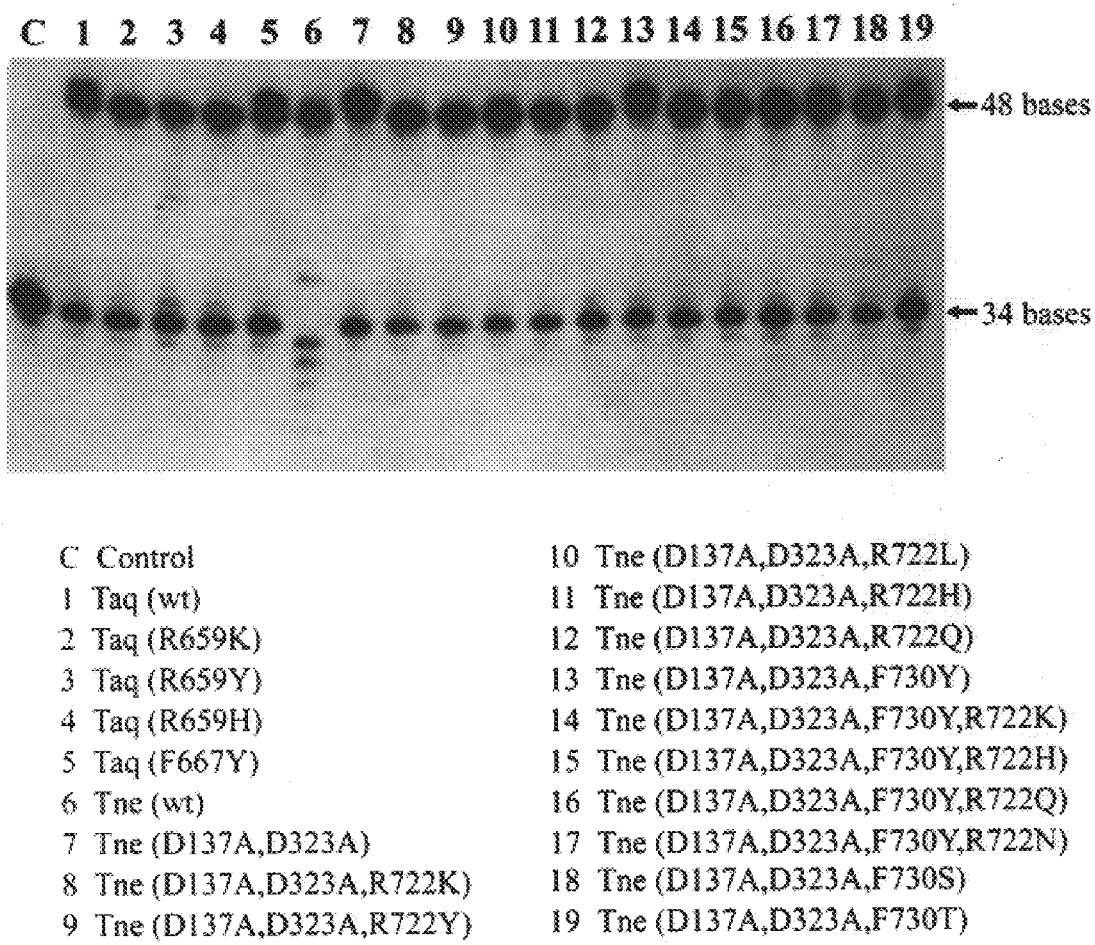
FIG. 6 depicts an autoradiogram showing of the ability of polymerase mutants to add non-templated 3' nucleotides.

A 2.5 kb portion of the gene encoding Taq DNA polymerase FIG. 5) was cloned as a Hind III-Xba I fragment into M13mp19. Site directed mutagenesis was performed using the BioRad mutagene kit (BioRad California) using the following oligonucleotides:

CTTGGCCGCCCGATGCATCAGGGGGTC (SEQ ID NO:41) for the R659H mutation where an NsiI site was created (see bold italics);

CTTGGCCGCCCGCTTCATGAGGGGGTCCAC (SEQ ID NO:42) for the R659K mutation where a BsIHI site was created (see bold italics); and CTTGGCCGCCCTGTACATCAGGGGGTC (SEQ ID NO:43) for the R659Y mutation where a BsrGI site was created (see bold italics).

For each mutation, six clones were screened by analyzing the M13RF DNA for the expected restriction sites. Mutations were confirmed by DNA sequencing. DNA shown to contain the mutation by the presence of the expected restriction site was digested with NgoAIV and Xba I and the approximately 1600 base pair fragment was used to replace corresponding fragment in the wildtype Taq DNA polymerase gene. These constructs were made in a plasmid containing Taq polymerase gene under the control of Tac promoter (pTTQ Taq) to generate pTTQ Taq (R659K), pTTQ Taq (R659H) and pTTQ Taq (R659Y). These plasmids were transformed into E. coli DH10B (LTI).

EXAMPLE 22
Construction of Tne polymerase Mutants Containing F730S and F730T Single stranded DNA was isolated from pSportTne (Tne35) containing D137A and D323A mutations as described in the section 2 of example 13. These D137 and D323A mutations rendered Tne DNA polymerase devoid of 5'-exonuclease and 3'-to-5'-exonuclease activities, respectively. Thus, Tne 35 is devoid of both exonuclease activities. The site-directed mutagenesis was done following the protocol described in section 3 of Example 13. The oligos used were 5' GTA TAT TAT AGA GGA GTT AAC CAT CTT TCC 3' (SEQ ID NO:37) for F730S and 5' GTA TAT TAT AGA GGT GTT AAC CAT CTT TCC 3' (SEQ ID NO:44) for F730T. Each of these two oligos contain a diagonistic HpaI site for screening of mutants in the MutS strain. The mutant plasmids were transferred to DH10B strains. The mutations were finally confirmed by DNA sequencing. The mutant polymerases were purified by the procedure as described in Example 20.

EXAMPLE 23
Determination of the Activity of Non-templated One Base Addition for Tne and Taq DNA Polymerase by Primer Extension Assay The following 34-mer primer was $^{32}$P labeled at the 5' end with [$\gamma$-$^{32}$P] ATP and T4 polynucleotide kinase by standard protocol (Molecular Cloning, A Laboratory Manual, Cold Spring Harbor, N.Y.):

5'-GGGAGACCGGAATTCTCCTTCATTAATTCCT ATA-3' (SEQ ID NO:45)

The unincorporated ATP was removed by a BioRad P6 column(1.0 ml). The labeled primer was annealed to the following homogenous (purified) 48-mer template:

5'-TGGAGACCCTGGAACTATAGGAATTAATGA AGGAGAATTCCGGT CTCCC-3' (SEQ ID NO:46).

Wildtype or mutant DNA polymerases (0.125–1.0 unit) were incubated at 72° C. for 2 min in 20 mM Tris-HCl (pH8.3), 1.5 mM MgCl$_2$, 50 mM KCl, 1.0 mM DTT, 200 uM of dCTP, dGTP, TTP, dATP, and 0.02 pmol of the annealed primer-template. After addition of sequencing stop buffer and heated at 90° C. for 2 min, the mixture was loaded onto 10% polyacrylamide-7 M urea. Following the electrophoresis, the gel was dried and the reaction products were analyzed by autoradiography. The non-templated one base addition products shown in FIG. 6 were quantified by a PhosphorImager (Molecular Dynamics).

| Tne | DNA polymerases | % of N + 1 |
| --- | --- | --- |
| 1 | D137A | 18.5 |
| 2 | D137A D323A | 78.5 |
| 3 | D137A D323A R722K | 0.7 |
| 4 | D137A D323A R722Y | 0.7 |
| 5 | D137A D323A R722L | 5.7 |
| 6 | D137A D323A R722H | 1.2 |
| 7 | D137A D323A R722Q | 1.4 |
| 8 | D137A D323A F730Y | 61.3 |
| 9 | D137A D323A R722K F730Y | 6.8 |
| 10 | D137A D323A R722H F730Y | 2.1 |
| 11 | D137A D323A R722Q F730Y | 6.1 |
| 12 | D137A D323A R722N F730Y | 15.9 |
| 13 | D137A D323A F730S | 8.3 |
| 14 | D137A D323A F730T | 24.2 |

| Taq | DNA Polymerases | % of N + 1 |
| --- | --- | --- |
| 1 | W.T. | 37 |
| 2 | R659K | 1.4 |
| 3 | R659Y | 0.9 |
| 4 | R659H | 0.5 |
| 5 | F667Y | 39.1 |

EXAMPLE 24
Comparison of DNA Synthesis by Taq and Tne

To examine its propensity to add a nontemplated nucleotides to the 3' termini of PCR products, Tne DNA polymerase (5'exo$^-$, 3'exo$^-$) was compared side-by-side with Taq DNA polymerase in amplifications of short tandem repeats at 23 different marker loci (see Table 1). Reactions comprising 20 nM TRIS-HCl, pH 8.4, 50 mM KCl, 1.5 mM MgCl$_2$, 200 mM each dNTP, 200 nM [$^{32}$P] $\alpha$-dATP, 200 nM each of the upper and lower primers, 25 ng of human DNA, 0.1% nonionic detergent and 1 unit of DNA polymerase (in a volume of 25 ml) were assembled on ice. Published sequences for upper and lower primers for each locus, as shown in Table 1, were used for all amplifications.

Reactions were loaded into a Perkin Elmer model 9600 thermocycler preheated to 94° C. and PCR was done using standard cycling conditions (1 minute pre-denaturation at 94° C.; 30 cycles of 30 seconds at 94° C., 30 seconds at 55° C., and 1 minute at 72° C.; 1 minute post-extension at 72° C.; overnight soak at 4° C.). A portion of each reaction was mixed with an equal volume of 95% formamide containing dyes to indicate the progress of electrophoresis. Samples were heated to 90° C. for 2 min, and 5 ml of each was loaded on a 6% denaturing polyacrylamide gel. Sequencing ladders were loaded to provide size markers, and electrophoresis was performed at 70 watts. After electrophoresis the gel was transferred to filter paper and dried. Autoradiography and phosphoimage analysis was performed to visualize the PCR products and estimate the percentage of product which contained the added nucleotide by direct comparison of bands produced by each enzyme.

Figure 7:
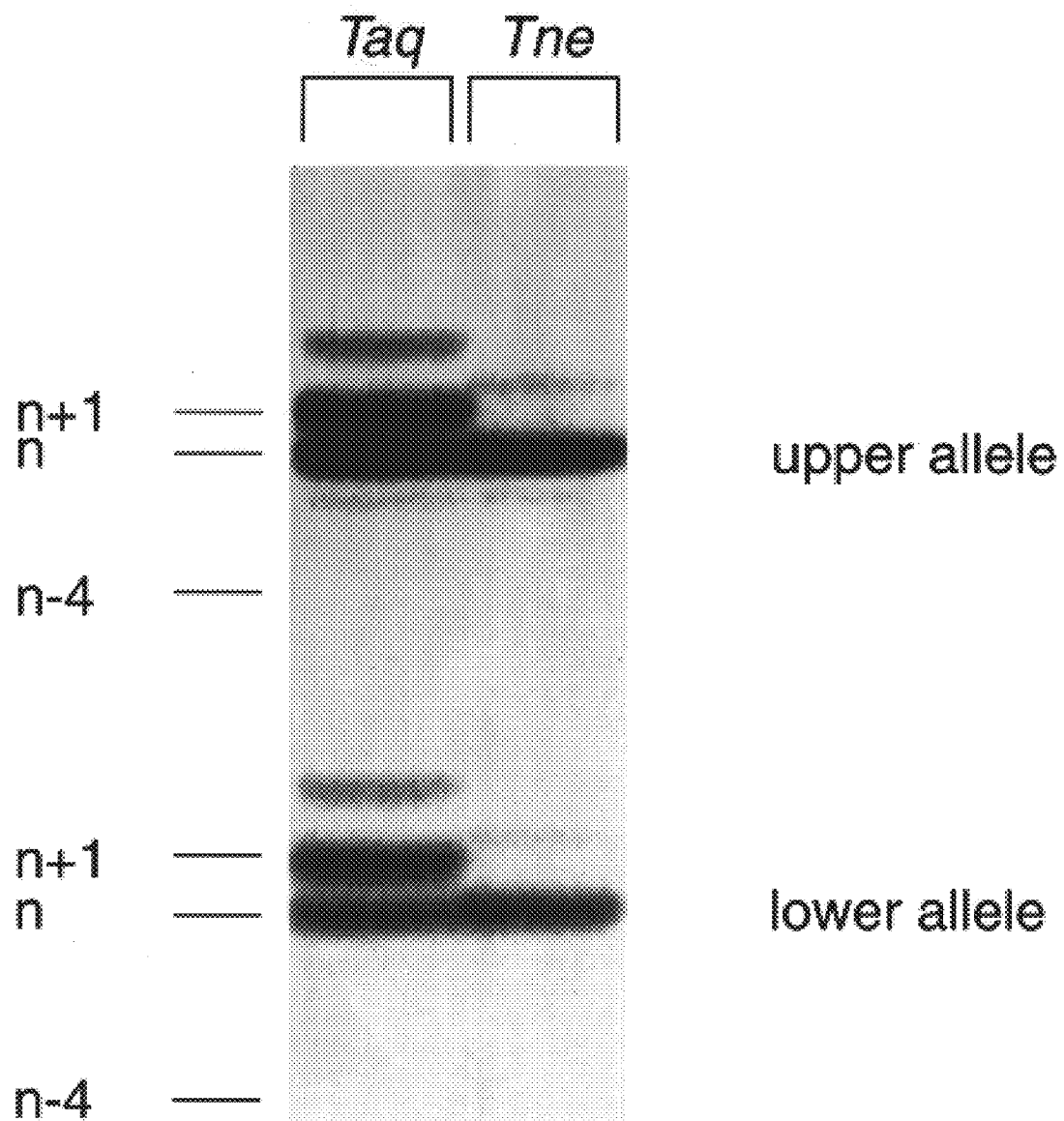
FIG. 7 is an autoradiogram of the product of PCR amplification of the upper and lower alleles of the CD4 locus, using primers corresponding to these alleles, demonstrating nontemplated nucleotide addition (n+1) by Taq DNA polymerase but not by Tne DNA polymerase.
Figure 8:
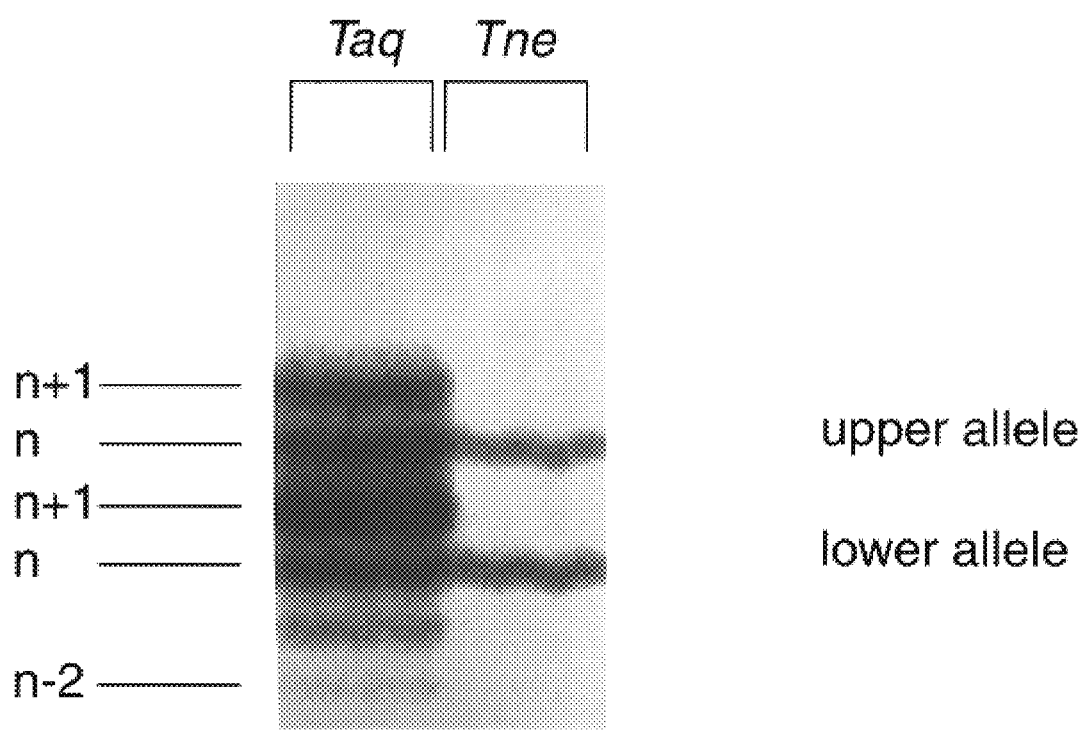
FIG. 8 is an autoradiogram of the product of PCR amplification of the upper and lower alleles of the D20S27 locus, using primers corresponding to these alleles, demonstrating nontemplated nucleotide addition (n+1) by Taq DNA polymerase but not by Tne DNA polymerase.

Examples of the side-by-side comparisons of amplification products produced by Taq DNA polymerase and Tne DNA polymerase are shown in FIG. 7 for the CD4 locus and in FIG. 8 for the D20S27 locus. At both of these loci, a significant portion of the Taq PCR product contained an extra non-templated nucleotide (n+1), while Tne polymerase demonstrated no apparent non-templated nucleotide incorporation for either the CD4 locus (FIG. 7) or the D20S27 locus (FIG. 8). Complete results for the 23 marker loci examined are summarized in Table 2. In PCRs using Taq DNA polymerase, a portion of the amplification product contained an extra non-templated nucleotide (n+1) at every locus examined. In PCRs using Tne DNA polymerase, however, no detectable portion of the product at any of the loci examined contained an additional non-templated nucleotide. These results indicate that Tne DNA polymerase, in contrast to Taq DNA polymerase, is substantially reduced in the ability to add a nontemplated 3' terminal nucleotide to the growing strand. Since the Tne DNA polymerase used in these amplifications was a 3'exo– mutant (i.e., it was substantially reduced in 3' exonuclease activity), these results are consistent with the notion that the Tne polymerase was unable to add the extra nucleotide to the product rather than adding the nucleotide and then removing it via a 3' exonuclease activity.

TABLE 1

Primers Used in Example 24.

| Locus | Upper Primer (SEQ ID NO:) | Lower Primer (SEQ ID NO:) | Reference |
| --- | --- | --- | --- |
| D13S71 | GTATTTTGGTATGCTTGTGC (47) | CTATTTTGGAATATATGTGCCT (48) | Nucl. Acids Res. 18:4638 (1990) |
| D1S103 | ACGAACATTCTACAAGTTAC (49) | TTTCAGAGAAACTGACCTGT (50) | Nucl. Acids Res. 18:2199 (1990) |
| D15S87 | GATAAATGCCAAACATGTTGT (51) | TGCTCTCAGGATTTCCTCCA (52) | Nucl. Acids Res. 18:4640 (1990) |
| D2S136 | AGCTTGAGACCTCTGTGTCC (53) | ATTCAGAAGAAACAGTGATGGT (54) | Nature Genet. 7:246–339 (1994) |
| CD4 | TTGGAGTCGCAAGCTGAACTAGC (55) | GCCTGAGTGACAGAGTGAGAACC (56) | Nucl. Acids Res. 19:4791 (1991) |
| PLA2A | CCCACTAGGTTGTAAGCTCCATGA (57) | TACTATGTGCCAGGCTCTGTCCTA (58) | Nucl. Acids Res. 18:7468 (1990) |

TABLE 1-continued

Primers Used in Example 24.

| Locus | Upper Primer (SEQ ID NO:) | Lower Primer (SEQ ID NO:) | Reference |
|---|---|---|---|
| D19S49 | ACTCATGAAGGTGACAGTTC (59) | GTGTTGTTGACCTATTGCAT (60) | Nucl. Acids Res. 18:1927 (1990) |
| D4S175 | ATCTCTGTTCCCTCCCTGTT (61) | CTTATTGGCCTTGAAGGTAG (62) | Genomics 14:209–219 (1992) |
| APOC2AC | AGCCCGTGTTGGAACCATGACTG (63) | TACATAGCGAGACTCCATCTCCC (64) | Hum. Genet. 83:245–251 (1989) |
| D20S27 | TTTATGCGAGCGTATGGATA (65) | CACCACCATTGATCTGGAAG (66) | Nucl. Acids Res. 18:2202 (1990) |
| D15S127 | CCAACCACACTGGGAA (67) | AACAGTTGCCCACGGT (68) | Nature Genet. 7:246–339 (1994) |
| D4S398 | CATGAAATGCTGACTGGGTA (69) | TCAATTTATGTGCAGCCAAT (70) | Nature Genet. 7:246–339 (1994) |
| APOC2 | CATAGCGAGACTCCATCTCC (71) | GGGAGAGGGCAAAGATCGAT (72) | Am. J. Hum. Genet. 44:388–396 (1989) |
| D10S89 | AACACTAGTGACATTATTTTCA (73) | AGCTAGGCCTGAAGGCTTCT (74) | Nucl. Acids Res. 18:4637 (1990) |
| VWA | CCCTAGTGGATGATAAGAATAATC (75) | GGACAGATGATAAATACATAGGATGGATGG (76) | Hum. Molec. Genet. 1:287 (1992) |
| D16S401 | TTCTCTTACAACACTGCCCC (77) | ATTTGGATGGCTTGACAGAG (78) | Nature Genet. 7:246–339 (1994) |
| D7S440 | ACATTCTAAGACTTTCCCAAT (79) | AGAGCATGCACCCTGAATTG (80) | Nucl. Acids Res. 18:4039 (1990) |
| D4S174 | AAGAACCATGCGATACGACT (81) | CATTCCTAGATGGGTAAAGC (82) | Nucl. Acids Res. 18:4636 (1990) |
| D16S520 | GCTTAGTCATACGAGCGG (83) | TCCACAGCCATGTAAACC (84) | Nature Genet. 7:246–339 (1994) |
| D16S511 | CCCCGGAGCAAGTTCA (85) | CAGCCCAAAGCCAGATTA (86) | Nature Genet. 7:246–339 (1994) |
| D21S11 | ATATGTGAGTCAATTCCCCAAG (87) | TGTATTAGTCAATGTTCTCCAG (88) | Hum. Molec. Genet. 1:67 (1992) |
| THO1 | CAGCTGCCCTAGTCAGCAC (89) | GCTTCCGAGTGCAGGTCACA (90) | Nucl. Acids Res. 19:3753 (1991) |
| ACTBP2 | ATTCTGGGCGCACAAGAGTGA (91) | ACATCTCCCCTACCGCTATA (92) | Nucl. Acids Res. 20:1432 (1992) |

TABLE 2

Non-templated 3' Terminal Nucleotide Addition by Taq and Tne DNA Polymerases at 23 Microsatellite DNA Loci.

| Locus | Repeat Type | Taq (% n + 1) | Tne (% n + 1) |
|---|---|---|---|
| D13S71 | dinucleotide | 100 | 0 |
| D1S103 | dinucleotide | 75–100 | 0 |
| D15S87 | dinucleotide | 30–50 | 0 |
| D25136 | dinucleotide | 90–100 | 0 |
| HUMCD4 | pentanucleotide | 50 | 0 |
| HUMPLA2A | trinucleotide | 25 | 0 |
| D19S49 | dinucleotide | 75 | 0 |
| D4S175 | dinucleotide | 75 | 0 |
| APOC2AC | dinucleotide | 50 | 0 |
| D20S27 | dinucleotide | 50 | 0 |
| D15S127 | dinucleotide | 100 | 0 |
| D4S398 | dinucleotide | 50 | 0 |
| APOC2 | dinucleotide | 50 | 0 |
| D10S89 | dinucleotide | 75–100 | 0 |
| HUMVWA | tetranucleotide | 90 | 0 |
| D16S401 | dinucleotide | 100 | 0 |
| D7S440 | dinucleotide | 90 | 0 |
| D4S174 | dinucleotide | 75 | 0 |
| D16S520 | dinucleotide | 100 | 0 |
| D16S511 | dinucleotide | 100 | 0 |
| HUMD21S11 | tetranucleotide | 100 | 0 |
| HUMTHO1 | tetranucleotide | 75 | 0 |
| HUMACTBP2 | tetranucleotide | 25 | 0 |

EXAMPLE 25

Compaison of DNA Synthesis by Tne and Other Thermostable Enzymes

To further evaluate the differences in the propensities of Tne and other thermostable DNA polymerases to add non-templated 3' terminal nucleotides to PCR products, side-by-side amplifications were performed using a single marker locus D1S103 and a variety of thermostable enzymes, including 3' exonuclease deficient (3'exo−) enzymes, and 3' exonuclease competent (3'exo+) enzymes. PCR amplifications, electrophoresis and analysis were performed as described for Example 24, using 200 nM of D1S103-specific upper and lower primers.

Results for the amplifications using 3'exo− DNA polymerases are shown in Table 3. With the exception of Tne(3'exo−), all of the 3'exo− DNA polymerases examined exhibited a propensity to add a non-templated 3' terminal nucleotide (n+1) to the PCR product. For Taq and Tbr DNA polymerases, up to 100% of the PCR products contained an additional non-templated 3' terminal nucleotide, while Vent, Deep Vent, and Dtok 3'exo− mutants polymerases added this non-templated nucleotide to 25–100% of the PCR products. In contrast, the 3'exo− mutant of Tne DNA polymerase was substantially reduced in the ability to add a nontemplated 3' terminal nucleotide to the DNA molecule; none of the PCR products from reactions using Tne(3'exo−) had an additional non-templated nucleotide at their 3' termini.

Results from amplifications using 3'exo+ DNA polymerases are shown in Table 4. Five polymerases were examined as well as two commercially available enzyme mixes (mixtures of a primary 3'exo− polymerase and a secondary 3'exo+ polymerase). At this locus, the 3'exo+ DNA polymerases (Tne, Tma, Pfu, Pwo and 9° North) yielded product which did not contain an extra non-templated nucleotide. The enzyme mixtures (Elongase and Expand HiFi) yielded a mixture of products with and without an additional non-templated nucleotide. Together, these results indicate that Tne polymerases, whether 3'exo− or 3'exo+, are substantially reduced in the ability to add a nontemplated 3' terminal nucleotide to the DNA molecule. Moreover, of the preferred 3'exo− polymerases, only Tne (3'exo−) was substantially reduced in this activity, indicating its favorableness in PCR applications where non-templated nucleotide addition to the amplification product is undesirable.

TABLE 3

Non-templated 3' Terminal Nucleotide Addition by 3'exo− DNA Polymerases.

| Enzyme | n Sized Fragment | n + 1 Sized Fragment |
|---|---|---|
| Tne (3'exo−) | + | − |
| Taq | − | + |
| Vent (3'exo−) | + | + |
| Deep Vent (3'exo−) | + | + |
| Dtok (3'exo−) | + | + |
| Thermolase Tbr | − | + |

TABLE 4

Non-templated 3' Terminal Nucleotide
Addition by 3'exo+ DNA Polymerases.

| Enzyme | n Sized Fragment | n + 1 Sized Fragment |
|---|---|---|
| Tne (3'exo+) | + | − |
| UlTma | + | − |
| Pfu | + | − |
| Pwo | + | − |
| 9° North | + | − |
| Elongase | + | + |
| Expand HiFi | + | + |

EXAMPLE 26
Comparison of DNA Synthesis by Tne Mutants

To examine the utility of Tne DNA polymerase and various mutants thereof in amplification of microsatellite DNA sequences, the experiments described in Example 25 were repeated with 11 different Tne DNA polymerase mutants. Of these mutants, 3 were 5'exo+, while the remainder were 5'exo− either due to N-terminal deletions of the protein, or to point mutations in the 5' exonuclease domain of the polymerase.

As shown in Table 5, use of the 5'exo− Tne mutants resulted in productive amplifications, yielding PCR products with no non-templated 3' terminal nucleotide additions. Results were identical for all seven Tne(3'exo−/5'exo−) polymerase mutants, as well as for the single Tne(3'exo+/5'exo−) mutant tested. Results with 5'exo+ Tne mutants were inconclusive under the conditions tested.

These results indicate that the mutants of Tne DNA polymerase tested in the present studies are substantially reduced in the ability to add nontemplated 3' terminal nucleotides to the growing strand, particularly a DNA template comprising a microsatellite DNA sequence or an STR.

TABLE 5

Non-templated 3' Terminal Nucleotide
Addition by Tne DNA Polymerase Mutants

| Enzyme | 5' exo Activity | 3' exo Activity | n Sized Fragment | n + 1 Sized Fragment |
|---|---|---|---|---|
| Tne N'Δ219, D323A | − | − | + | − |
| Tne N'Δ283, D323A | − | − | + | − |
| Tne N'Δ192, D323A | − | − | + | − |
| Tne D137A, D323A | − | − | + | − |
| Tne D8A, D323A | − | − | + | − |
| Tne G195D, D323A | − | − | + | − |
| Tne G37D, D323A | − | − | + | − |
| Tne N'Δ283 | − | + | + | − |

EXAMPLE 27
Fluorescent Analysis of DNA Synthesis by Tne and Taq DNA Polymerases In an alternative analysis approach, the propensities of Taq DNA polymerase and Tne DNA polymerase to add non-templated nucleotides to the PCR products were compared using fluorescent detection. The polymerases were compared in side-by-side amplifications utilizing a commonly used commercially available marker panel (ABI Prism Linkage Mapping Set Panel 21), examining ten different loci. Reaction mixtures (15 ml) containing 1.5 mM $MgCl_2$, 250 mM of each deoxynucleoside triphosphate, 333 nM of each primer, 50 ng of human DNA and 0.6 units of Taq or Tne DNA polymerase were assembled on ice. Reactions were loaded into a Perkin Elmer model 9600 thermocycler preheated to 95° C., and PCR was performed using recommended cycling conditions (5 minutes pre-denaturation at 95° C.; 10 cycles of 15 seconds at 95° C., 15 seconds at 55° C., and 60 seconds at 72° C.; and 20 cycles of 15 seconds at 89° C., 15 seconds at 55° C., and 60 seconds at 72° C.). Two sets of extension reactions were conducted for each locus, one with a 10 minute post-extension incubation at 72° C. followed by an overnight soak and storage at 4° C. (conditions which favor nontemplated 3' nucleotide addition), the other with no post-extension incubation followed by immediate storage at −20° C. (conditions which inhibit nontemplated 3' nucleotide addition). A portion of each reaction was diluted, mixed with loading cocktail, heat denatured and loaded on an 8% polyacrylamide sequencing gel. The ABI 373 Stretch Automated Sequencer was run for 5–6 hours at 15W in order to obtain single base resolution, and data were analyzed using GeneScan software. Areas of the peaks recognized by the software were used to estimate the percentage of nontemplated 3' nucleotide addition ("n+1") for each locus by the two polymerases under the two different extension conditions. The total area under the allelic peaks was used to compare the yields of specific PCR product obtained in Tne and Taq amplifications, and yields produced by Tne polymerase were expressed for each locus as a percentage of those produced by Taq polymerase. Table 6 summarizes the results obtained.

TABLE 6

Comparison of DNA Amplification by
Taq and Tne DNA Polymerases by Fluorescent Detection

| locus | color | expected size | cycling conditions | Taq pattern | Tne pattern | Tne yield (% Taq) |
|---|---|---|---|---|---|---|
| D16S405 | blue | 107–145 | no final ext | 0% | 100% n | 89% |
|  |  |  | ext | n + 1 | 100% n | 178% |
|  |  |  | 10' | 94% |  |  |
|  |  |  | final ext | n + 1 |  |  |
| D15S127 | green | 114–148 | no final ext | 53% | 100% n | 133% |
|  |  |  | ext | n + 1 | 100% n | 142% |
|  |  |  | 10' | 100% |  |  |
|  |  |  | final ext | n + 1 |  |  |
| D16S520 | yellow | 144–160 | no final ext | 40% | 98% n | 275% |
|  |  |  | ext | n + 1 | 100% n | 252% |
|  |  |  | 10' | 100% |  |  |
|  |  |  | final ext | n + 1 |  |  |
| D16SS11 | green | 182–222 | no final ext | 62% | 100% n | 51% |
|  |  |  | ext | n + 1 | 100% n | 160% |
|  |  |  | 10' | 100% |  |  |
|  |  |  | final ext | n + 1 |  |  |
| D16S411 | blue | 215–235 | no final ext | 0% | 100% n | 218% |
|  |  |  | ext | n + 1 | 100% n | 257% |
|  |  |  | 10' | 64% | 95% n | 305% |
|  |  |  | final ext | n + 1 |  |  |
|  |  |  | 10' | 67% |  |  |
|  |  |  | final ext | n + 1 |  |  |
| D15S131 | yellow | 237–275 | no final ext | 0% | 100% n | 48% |
|  |  |  | ext | n + 1 | 95% n | 231% |
|  |  |  | 10' | 69% |  |  |
|  |  |  | final ext | n + 1 |  |  |
| D15S130 | blue | 280–294 | no final ext | 0% | 100% n | 101% |
|  |  |  | ext | n + 1 |  |  |

TABLE 6-continued

Comparison of DNA Amplification by
Taq and Tne DNA Polymerases by Fluorescent Detection

| locus | color | expected size | cycling conditions | Taq pattern | Tne pattern | Tne yield (% Taq) |
|---|---|---|---|---|---|---|
| D16S503 | yellow | 294–310 | no final ext | 0% | 100% n | 102% |
| | | | 10' | n + 1 73% | 100% n | 166% |
| | | | final ext | n + 1 | | |
| D15S117 | green | 316–334 | no final ext | 17% | 100% n | 130% |
| | | | 10' | n + 1 77% | 100% n | 326% |
| | | | final ext | n + 1 | | |
| D16S515 | blue | 320–350 | no final ext | 32% | 100% n | 486% |
| | | | 10' | n + 1 100% | 100% n | 298% |
| | | | final ext | n + 1 | | |

The results shown in Table 6 confirm that under conditions favoring ("10' final ext") or inhibiting ("no final ext") 3' nontemplated nucleotide addition, Tne DNA polymerase produced PCR products that were 95–100% free from non-templated nucleotide addition ("n") for each locus examined. Taq DNA polymerase, however, demonstrated significant addition of nontemplated nucleotides under inhibiting conditions in most loci tested, while under permissive conditions well over half, and in some cases all, of the PCR product produced by Taq DNA polymerase demonstrated an additional nontemplated 3' nucleotide. Furthermore, under most conditions the amount of PCR product yielded by Tne DNA polymerase was at least as high as that of Taq DNA polymerase, and for some loci was 3- to 4-fold higher.

Figure 9A:
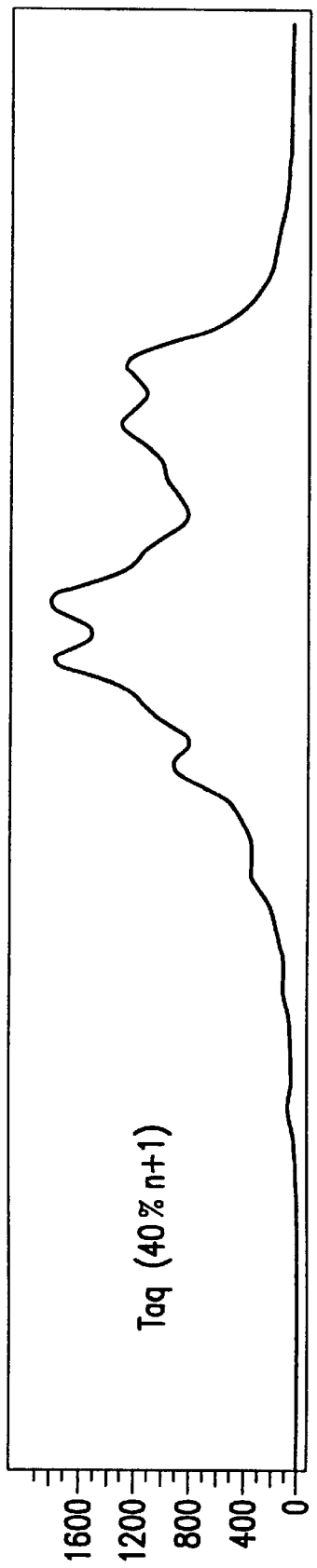
FIG. 9 is a composite of electropherogram gel scans of PCR amplifications at the D15S153 (FIGS. 9A and 9B) and D15S127 loci (FIGS. 9C and 9D), demonstrating nontemplated nucleotide addition (n+1) by Taq DNA polymerase (FIGS. 9A and 9C) but not by Tne DNA polymerase (FIGS. 9B and 9D).
Figure 9B:
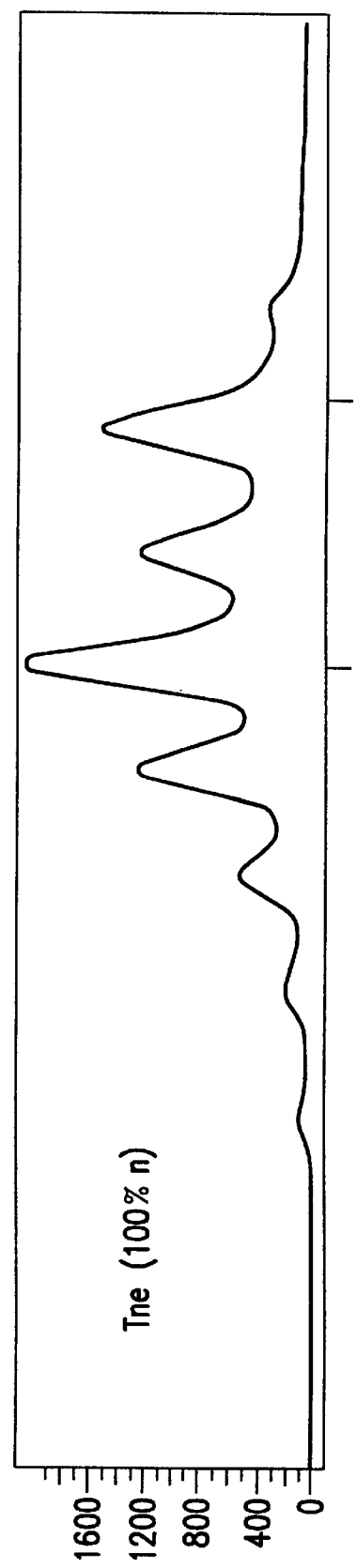

FIG. 9 shows two examples of electropherogram gel scans, aligned by PCR product size, comparing the PCR products obtained with Taq and Tne polymerases with a 10-minute final extension. For the D15S153 locus, Taq exhibited non-templated nucleotide addition to 40% of the PCR product (FIG. 9A), while Tne exhibited no such addition of non-templated nucleotides (FIG. 9B). Similar results were obtained with the D15S127 locus: 53% of the Taq PCR products demonstrated non-templated nucleotide addition (FIG. 9C), while none of the Tne PCR products demonstrated non-templated nucleotide addition (FIG. 9D). These results demonstrate the difficulty in identifying alleles in a heterogeneous pattern as generated by Taq amplification, compared to the more homogeneous, simple pattern generated by amplification with Tne.

Together with Examples 24–26, these results indicate that Tne DNA polymerase and the mutants thereof tested in the present studies are substantially reduced in the ability to add a nontemplated 3' terminal nucleotide to DNA templates, particularly DNA templates comprising microsatellite DNA sequences or STRs. Conversely, Taq DNA polymerase demonstrates significant addition of nontemplated 3' nucleotides to PCR products.

EXAMPLE 28
Comparison of Taq and Tne

To examine the ability of a truncated form of Tne DNA polymerase N'Δ283, 5'exo–, 10% 3'exo activity) to add a nucleotide to the end of the PCR product, the enzyme was compared side-by-side with wild type Taq DNA polymerase in amplifications of short tandem repeats at 5 different marker loci. A portion of ABI Prism Linkage Mapping Set Panel 21 was used for the primer sets for the loci. 15 ul reactions (20 mM Tris-HCl, pH 8.4, 50 mM KCl 1.5 mM $MgCl_2$, 200 uM each dNTP, 333 nM each primer, 60 ng human DNA, 0.1% nonionic detergent, 0.6 U DNA polymerase) were assembled on ice.

Reactions were loaded into a Perkin Elmer model 9600 thermocycler preheated to 95° C. and PCR was done using recommended cycling conditions (5 min. pre-denaturation at 95° C.; 10 cycles of 15 sec at 95° C., 15 sec at 55° C., and 60 sec at 72° C.; 20 cycles of 15 sec at 89° C., 15 sec at 55° C., and 60 sec at 10 min final extension at 72° C.). A portion of each reaction was diluted, mixed with loading cocktail, heat denatured and loaded on an 8% sequencing gel. The ABI 373 Stretch Automated Sequencer was run for 5–6 hr at 15W in order to obtain 1 base resolution. Data was analyzed using GeneScan software. Areas of the peaks recognized by the software were used to estimate the percent of extranucleotide addition. Table 7 summarizes the results obtained. Examples of the electropherogram data are shown in FIGS. 10A–D.

TABLE 7

Percent extranucleotide addition exhibited by
Taq and Tne DNA polymerases at specific loci.

| Locus | Taq (% n + 1) | Tne (% n + 1) |
|---|---|---|
| D16S405 | 46 | 0 |
| D16S401 | 100 | 45 |
| D16S520 | 63 | 0 |
| D15S131 | 51 | 0 |
| D16S411 | 53 | 0 |

EXAMPLE 29
Comparison of Tne Mutants

In order to evaluate the effect of amino acid substitutions in Tne DNA polymerase in regard to extra nucleotide addition, different mutations at position F730 in the untruncated polymerase were compared in side-by-side amplifications with Taq(wild type) and a truncated Tne(N'Δ219, D323A, F730Y) utilizing a portion of ABI Prism Linkage Mapping Set Panel 21. Six loci were examined. 15 ul reactions (20 mM Tris-HCl, pH 8.4, 50 mM KCl, 1.5 mM $MgCl_2$, 200 uM each dNTP, 333 nM each primer, 50–60 ng human DNA, 0.1% nonionic detergent, 0.15–0.6 U DNA polymerase) were assembled on ice.

Figure 11A:
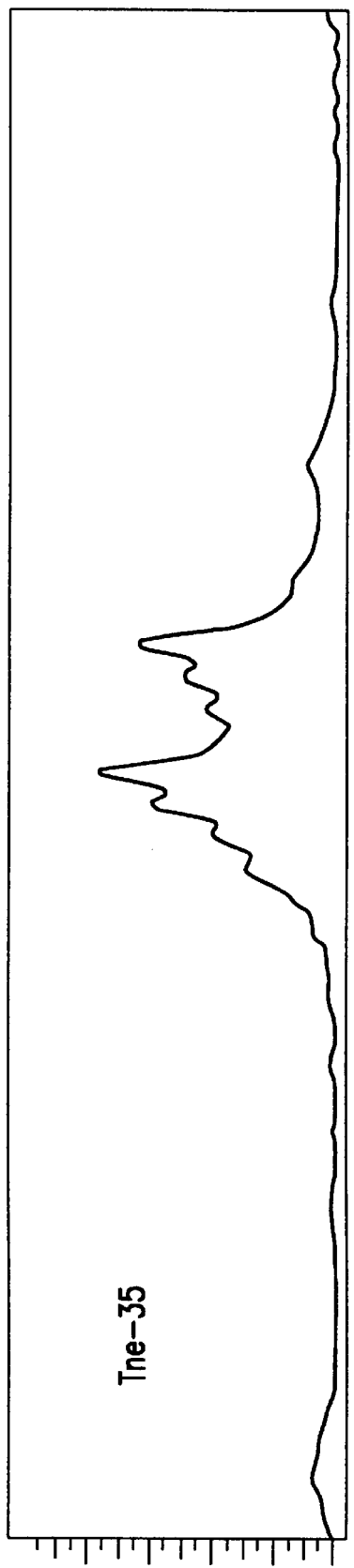
FIGS. 11A–B is a composite of a electropherogram gel scan of PCR amplifications at D16S401 locus.
Figure 11B:
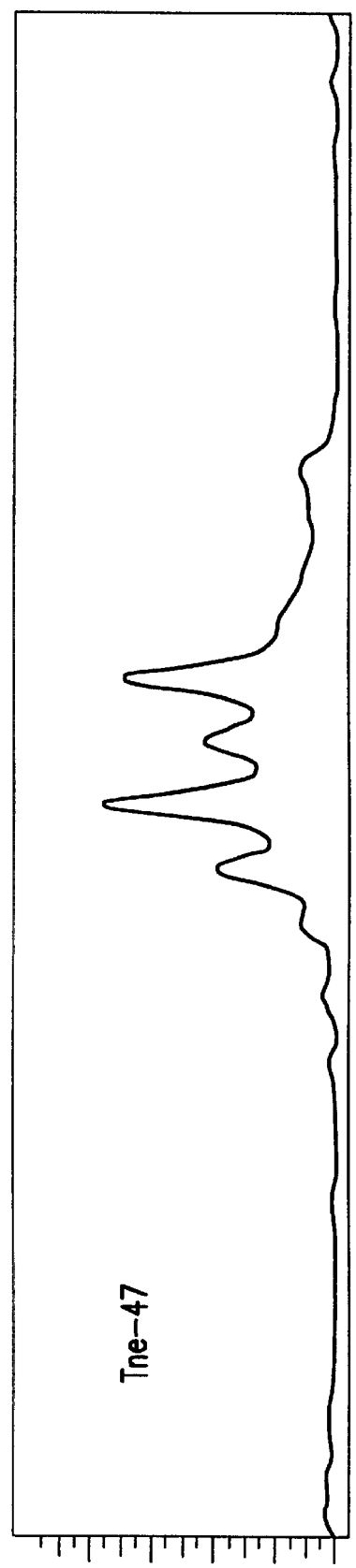
Figure 12A:
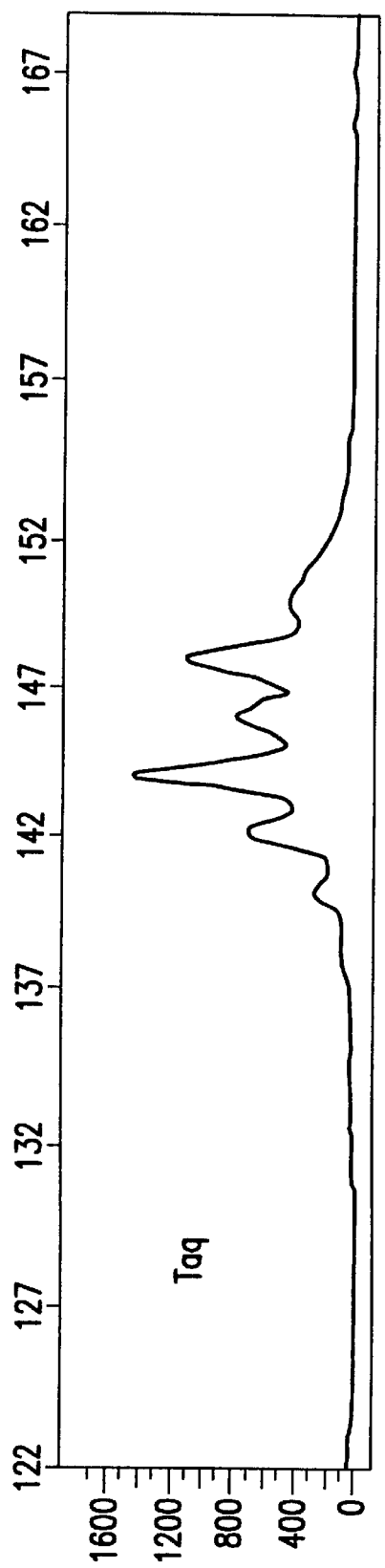
FIGS. 12A–F are composites of a electropherogram gel scan of PCR amplifications at D15S127 and D15S153 loci.
Figure 12B:
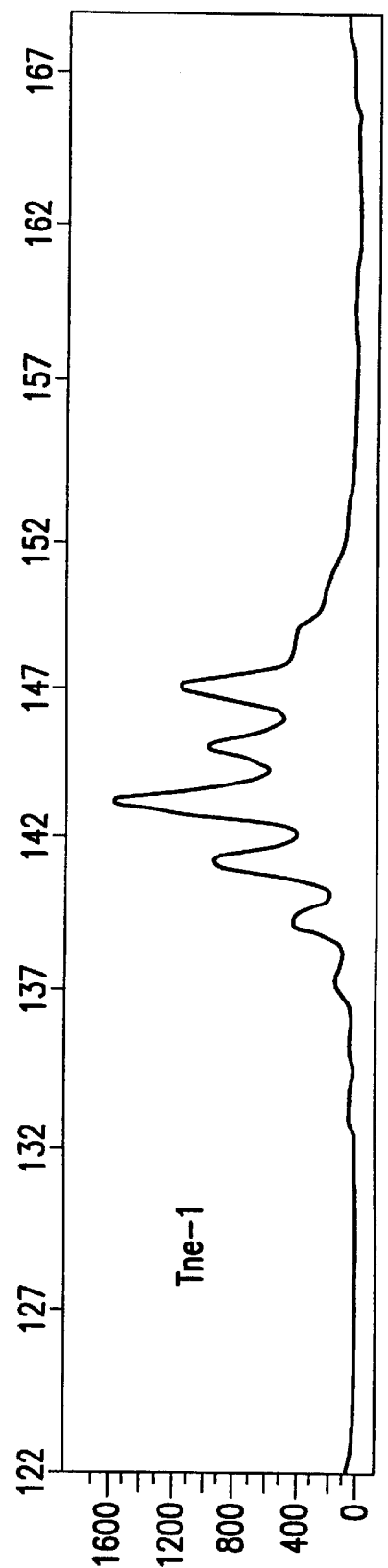
Figure 12C:
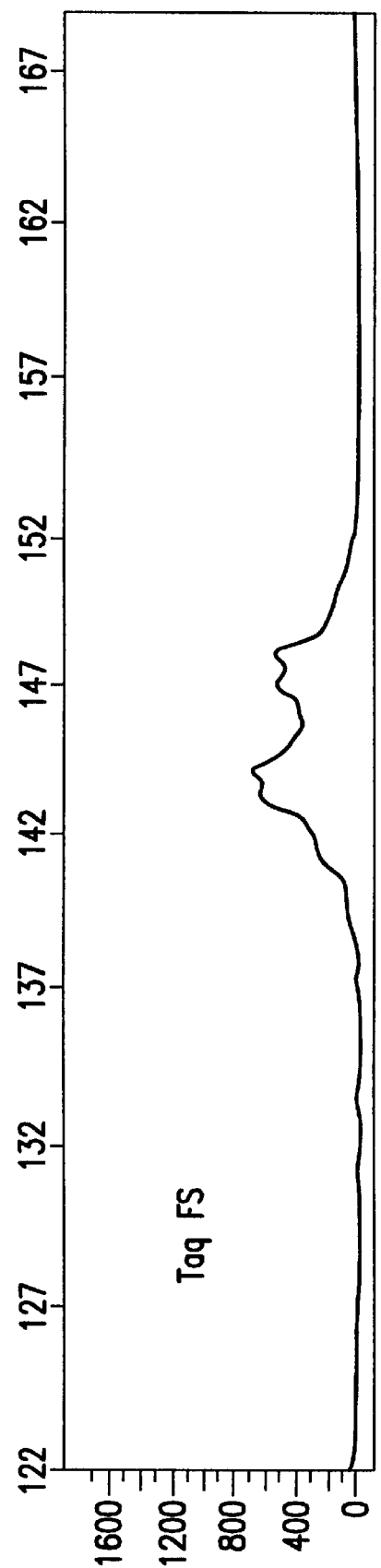
Figure 12D:
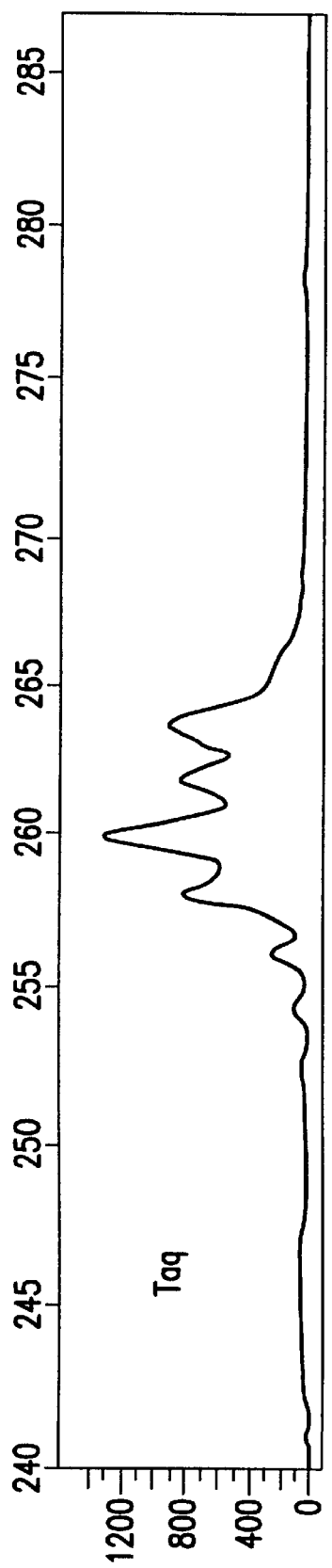
Figure 12E:
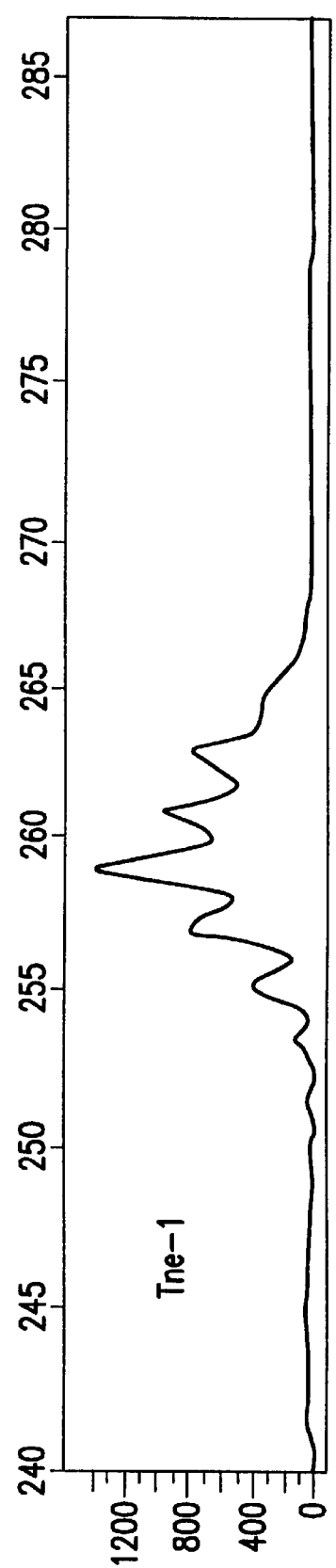
Figure 12F:
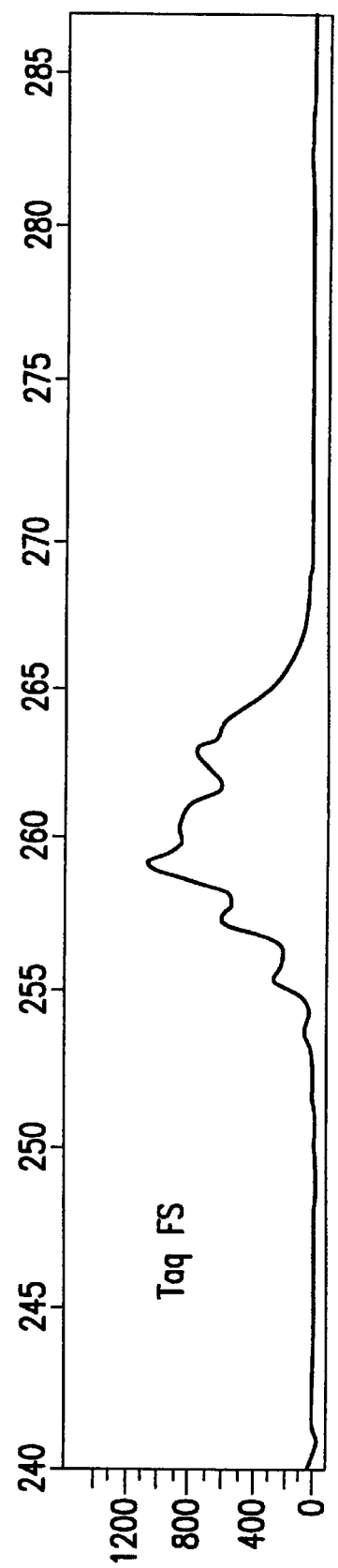

Reactions were loaded into a Perkin Elmer model 9600 thermocycler preheated to 95° C. and PCR was done using recommended cycling conditions (5 min. pre-denaturation at 95° C.; 10 cycles of 15 sec at 95° C., 15 sec at 55° C., and 60 sec at 72° C.; 20 cycles of 15 sec at 89° C., 15 sec at 55° C., and 60 at 72° C. 10 min final extension at 72° C.). A portion of each reaction was diluted, mixed with loading cocktail, heat denatured and loaded on an 8% sequencing gel. The ABI 373 Stretch Automated Sequencer was run for 5–6 hr at 15 W in order to obtain 1 base resolution. Data was analyzed using GeneScan software. Areas of the peaks recognized by the software were used to estimate the percent of extranucleotide addition. Table 8 summarizes the results obtained. An example of the electropherogram data are shown in FIGS. 11A–B.

TABLE 8

Percent extranucleotide addition exhibited by mutant Tne DNA polymerases at specific loci.

| mutant: | | locus: D16S405 | D16S401 | D15S131 | D15S127 | D16S511 | D15S153 |
|---|---|---|---|---|---|---|---|
| Taq | (wild type) | 46% | 100% | 51% | 100% | 100% | 100% |
| Tne-1 | (N'Δ219, D323A, F730Y) | 0% | 0% | 0% | 0% | 0% | 0% |
| Tne-35 | (D137A, D323A) | 0% | 52% | 0% | 0% | 0% | 0% |
| Tne-18 | (D137A, D323A, F730Y) | 0% | 2% | 0% | 0% | 0% | 0% |
| Tne-13 | (D137A, D323A, R722H, F730Y) | 0% | 0% | 0% | 0% | 0% | 0% |
| Tne-14 | (D137A, D323A, F730A) | nd | 0% | 0% | nd | nd | nd |
| Tne-47 | (D137A, D323A, F730S) | 0% | 0% | 0% | 0% | 0% | 0% |
| Tne-48 | (D137A, D323A, F730T) | 0% | 0% | 0% | 0% | 0% | 0% |

EXAMPLE 30

Comparison of Tne and Taq Mutants

In order to evaluate the effect of amino acid substitution at position F667 in Taq DNA polymerase (equivalent to F730 in Tne DNA polymerase) in regard to extra nucleotide addition, a commercially available mutant of Taq DNA polymerase (Taq FS) (N'Δ3, G46D, F667Y) was compared in side-by-side amplifications with Taq DNA polymerase (wild type) and Tne-1 DNA polymerase(N'Δ219, D323A, F730Y). Three loci were examined (a portion of ABI Prism Linkage Mapping Set Panel 21). 15 ul reactions (20 mM Tris-HCl, pH 8.4, 50 mM KCl, 1.5 mM MgCl$_2$, 200 uM each dNTP, 333 nM each primer, 60 ng human DNA, 0.1% nonionic detergent, 0.6 U DNA polymerase) were assembled on ice.

Reactions were loaded into a Perkin Elmer model 9600 thermocycler preheated to 95° C. and PCR was done using recommended cycling conditions (5 min. pre-denaturation at 95° C.; 10 cycles of 15 sec at 95° C., 15 sec at 55° C., and 60 sec at 72° C.; 20 cycles of 15 sec at 89° C., 15 sec at 55° C., and 60 sec at 10 min final extension at 72° C.). A portion of each reaction was diluted, mixed with loading cocktail, heat denatured and loaded on an 8% sequencing gel. The ABI 373 Stretch Automated Sequencer was run for 5–6 hr at 15 W in order to obtain 1 base resolution. Data was analyzed using GeneScan software. Areas of the peaks recognized by the software were used to estimate the percent of extranucleotide addition. Table 9 summarizes the results obtained. Examples of the electropherogram data are shown in FIGS. 12A–F.

TABLE 9

Percent extranucleotide addition exhibited by Taq and Tne DNA polymerases at specific loci.

| locus | Taq (% n + 1) | TaqFS (% n + 1) | Tne– (% n + 1) |
|---|---|---|---|
| D16S411 | 48 | 0 | 0 |
| D15S127 | 100 | 31 | 5 |
| D15S153 | 100 | 29 | 0 |

EXAMPLE 31

Comparison of Tne Mutants

In order to evaluate the effect of amino acid substitutions at position R722 in Tne DNA polymerase in regard to extranucleotide addition, different mutations in the polymerase were compared in side-by-side amplifications utilizing a portion of ABI Prism Linkage Mapping Set Panel 21. Six loci were examined. 15 ul reactions (20 mM Tris-HCl, pH 8.4, 50 mM KCl, 1.5 mM MgCl$_2$, 200 uM each dNTP, 333 nM each primer, 50–60 ng human DNA, 0.1% nonionic detergent, 0.2–0.6 U DNA polymerase) were assembled on ice.

Figure 13A:
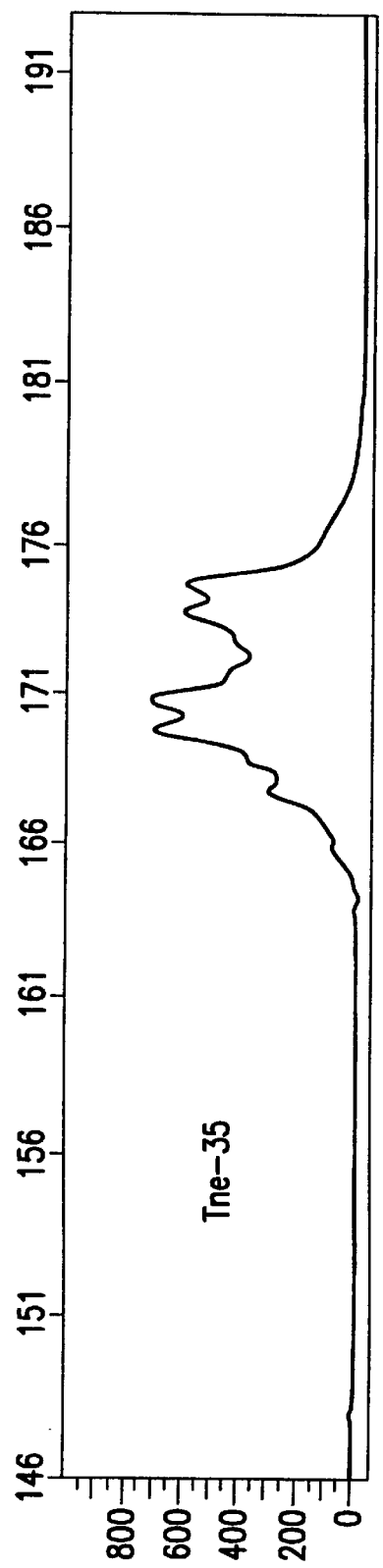
FIGS. 13A–C is a composite of a electropherogram gel scan of PCR amplifications at D16S401 locus.
Figure 13B:
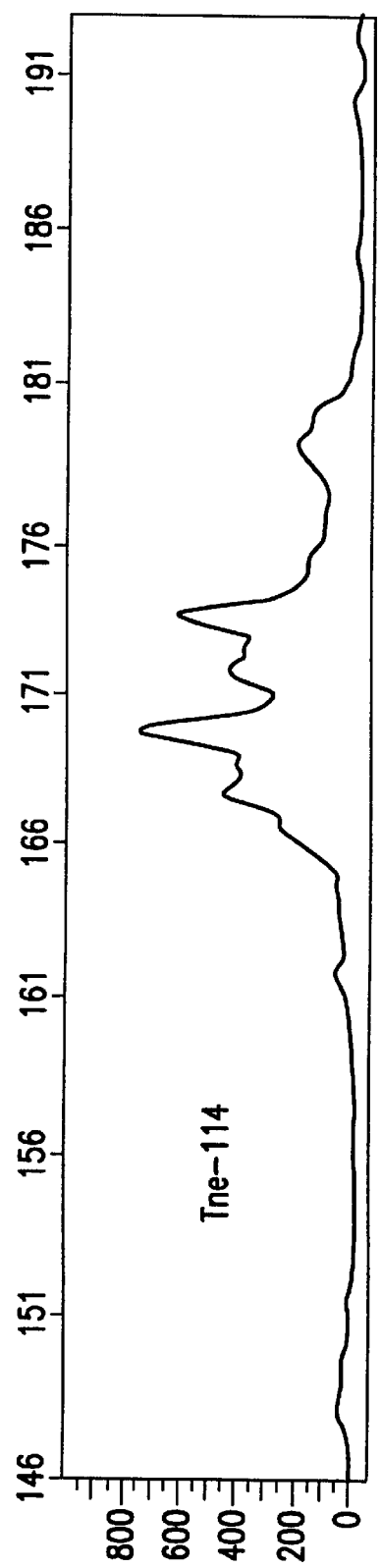
Figure 13C:
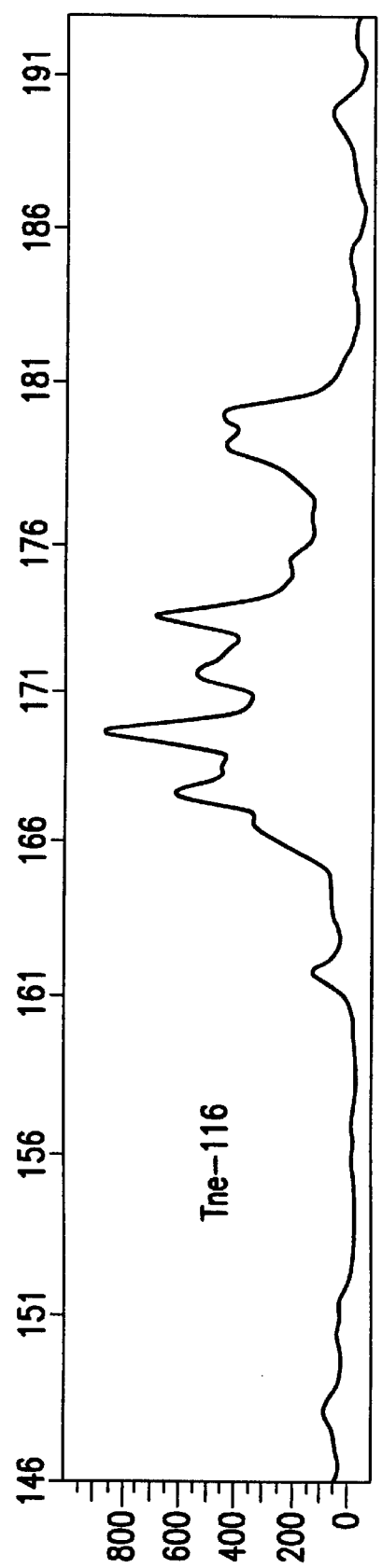

Reactions were loaded into a Perkin Elmer model 9600 thermocycler preheated to 95° C. and PCR was done using recommended cycling conditions (5 min. pre-denaturation at 95° C.; 10 cycles of 15 sec at 95° C., 15 sec at 55° C., and 60 sec at 72° C.; 20 cycles of 15 sec at 89° C., 15 sec at 55° C., and 60 sec at 72° C.; 10 min final extension at 72° C.). A portion of each reaction was diluted, mixed with loading cocktail, heat denatured and loaded on an 8% sequencing gel. The ABI 373 Stretch Automated Sequencer was run for 5–6 hr at 15 W in order to obtain 1 base resolution. Data was analyzed using GeneScan software. Heights of the n and n+1 peaks recognized by the software were used to estimate the percent of extranucleotide addition. Table 10 summarizes the results obtained. An example of the electropherogram data are shown in FIGS. 13A–C.

TABLE 10

Percent extranucleotide addition exhibited by mutant Tne DNA polymerases at specific loci.

| mutant: | | locus: D16S405 | D16S401 | D15S131 | D15S127 | D16S511 | D15S153 |
|---|---|---|---|---|---|---|---|
| Tne-35 | (D137A, D323A) | 0% | 54% | 0% | 0% | 0% | 0% |
| Tne-109 | (D137A, D323A, R722Y) | 0% | 0% | 0% | 0% | 0% | 0% |
| Tne-110 | (D137A, D323A, R722L) | 0% | 0% | 0% | 0% | 0% | 0% |
| Tne-114 | (D137A, D323A, R722K) | 0% | 0% | 0% | 0% | 0% | 0% |
| Tne-115 | (D137A, D323A, R722Q) | 0% | 0% | 0% | 0% | 0% | 0% |
| Tne-116 | (D137A, D323A, R722H) | 0% | 0% | 0% | 0% | 0% | 0% |

EXAMPLE 32
Generation of Tne DNA Polymerase Mutant K726R

The mutation of the Tne polymerase was done by essentially the same procedure as described above in Example 13. The single-stranded DNA was isolated from pSport-Tne containing D137A and D323A mutations. The oligonucleotide used for the mutagenesis was 5'-GAA GTT CAC CAT CCG GCC GAC CCG TCG CAT TTC 3' (SEQ ID NO:93). An XmaIII site (bold italics in the above sequence) was introduced into the oligonucleotide for easy screening of the mutants. The mutation was confirmed by DNA sequencing. The clone was named pTne129 (D137A, D323A, K726R).

EXAMPLE 33
Determination of the Activity of Non-templated One Base Addition for Tne DNA Polymerase and its Mutant D137A, D323A, K726R, by Primer Extension Assay The mutant Tne DNA polymerase (Tne D137A, D323A, K726R) prepared in Example 32 was purified as described in Example 20. The assay for non-templated one base addition was conducted as described in Example 23. The results were as follows:

| Tne DNA Polymerase | % of Product With N + 1 |
|---|---|
| D137A, D323A | 78.4 |
| D137A, D323A, R722H | 1.7 |
| D137A, D323A, K726R | 0.9 |

These results demonstrate that mutation of the lysine residue at position 726 of Tne, particularly to arginine, substantially reduces the activity of the polymerase in adding non-templated bases.

Having now fully described the present invention in some detail by way of illustration and example for purposes of clarity of understanding, it will be obvious to one of ordinary skill in the art that the same can be performed by modifying or changing the invention within a wide and equivalent range of conditions, formulations and other parameters without affecting the scope of the invention or any specific embodiment thereof, and that such modifications or changes are intended to be encompassed within the scope of the appended claims.

All publications, patents and patent applications mentioned in this specification are indicative of the level of skill of those skilled in the art to which this invention pertins, and are herein incorporated by reference to the same extent as if each individual publication, patent or patent application was specifically and individually indicated to be incorporated by reference.

---

What is claimed is:

1. A polymerase which comprises one or more modifications or mutations in the O-helix of said polymerase that reduce, substantially reduce or eliminate the ability of the polymerase to add non-templated 3' nucleotides to a synthesized nucleic acid molecule, wherein said polymerase is not a Thermotoga polymerase.

2. The polymerase of claim 1, wherein said polymerase is selected from the group consisting of Taq DNA polymerase, Tth DNA polymerase, Tli DNA polymerase, VENT® DNA polymerase, Pfu DNA polymerase, DEEPVENT® DNA polymerase, Pwo DNA polymerase, Bst DNA polymerase, Bca DNA polymerase, and Tfl DNA polymerase.

3. The polymerase of claim 1, wherein said O-helix is defined as RXXXKXXXFXXXYX (SEQ ID NO:11), wherein X is any amino acid.

4. The polymerase of claim 3, wherein said mutation or modification is at one or more positions or combinations of positions of said O-helix selected from the group consisting of position R (Arg), position F (Phe), position K (Lys), positions R and F, positions R and K, positions F and K, and positions R, F and K.

5. The polymerase of claim 3, wherein said mutation or modification is an amino acid substitution at one or more positions or combinations of positions of said O-helix selected from the group consisting of position R, position F, position K, positions R and F, positions R and K, positions F and K, and positions R, F and K.

6. The polymerase of claim 5, wherein K (Lys) is substituted with Arg or His.

7. A mutant Tne DNA polymerase protein selected from the group consisting of:
   Tne N'Δ283, D323A;
   Tne N'Δ284, D323A;
   Tne N'Δ193, D323A;
   Tne G195D, D323A;
   Tne G37D, D323A;
   Tne N'Δ283;
   Tne D137A, D323A, R722K;
   Tne D137A, D323A, R722Y;
   Tne D137A, D323A, R722L;
   Tne D137A, D323A, R722H;
   Tne D137A, D323A, R722Q;
   Tne D137A, D323A, K726R;
   Tne D137A, D323A, K726H;
   Tne D137A, D323A, R722K, F730Y;
   Tne D137A, D323A, R722K, K726R;
   Tne D137A, D323A, R722K, K726H;
   Tne D137A, D323A, R722H, F730Y;
   Tne D137A, D323A, R722H, K726R;
   Tne D137A, D323A, R722H, K726H;
   Tne D137A, D323A, R722Q, F730Y;
   Tne D137A, D323A, R722Q, K726R;
   Tne D137A, D323A, R722Q, K726H;
   Tne D137A, D323A, R722N, F730Y;
   Tne D137A, D323A, R722N, K726R;
   Tne D137A, D323A, R722N, K726H;
   Tne D137A, D323A, F730S;
   Tne N'Δ283, D323A, R722K/H/Q/N/Y/L;
   Tne N'Δ219, D323A, R722K;
   Tne N'Δ219, D323A, K726R;
   Tne N'Δ219, D323A, K726H;
   Tne D137A, D323A, F730S, R722K/Y/Q/N/H/L, K726R/H;
   Tne D137A, D323A, F730T, R722K/Y/Q/N/H/L, K726R/H;
   Tne D137A, D323A, F730T; and
   Tne D137A, D323A, R722N.

8. A polymerase which comprises one or more modifications or mutations in the O-helix of said polymerase that reduce, substantially reduce or eliminate the ability of the polymerase to add non-templated 3' nucleotides to a synthesized nucleic acid molecule, wherein said mutation or modification is at one or more positions or combinations of positions of said O-helix selected from the group consisting of position R (Arg), position F (Phe), position K (Lys), positions R and F, positions R and K, positions F and K, and positions R, F and K, and wherein said polymerase is not a Thermotoga polymerase.

9. A polymerase which comprises one or more modifications or mutations in the O-helix of said polymerase that reduce, substantially reduce or eliminate the ability of the polymerase to add non-templated 3' nucleotides to a synthesized nucleic acid molecule, wherein said mutation or modification is an amino acid substitution at one or more positions or combinations of positions of said O-helix selected from the group consisting of position R, position F, position K, positions R and F, positions R and K, positions F and K, and positions R, F and K, and wherein said polymerase is not a Thermotoga polymerase.

* * * * *

SEQUENCE LISTING (1) GENERAL INFORMATION:

(iii) NUMBER OF SEQUENCES: 93

(2) INFORMATION FOR SEQ ID NO:1:

(i) SEQUENCE CHARACTERISTICS:
        (A) LENGTH: 2682 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:1:

```
ATGGCGAGAC TATTTCTCTT TGATGGCACA GCCCTGGCCT ACAGGGCATA TTACGCCCTC      60

GACAGATCCC TTTCCACATC CACAGGAATT CCAACGAACG CCGTCTATGG CGTTGCCAGG     120

ATGCTCGTTA AATTCATTAA GGAACACATT ATACCCGAAA AGGACTACGC GGCTGTGGCC     180

TTCGACAAGA AGGCAGCGAC GTTCAGACAC AAACTGCTCG TAAGCGACAA GGCGCAAAGG     240

CCAAAGACTC CGGCTCTTCT AGTTCAGCAG CTACCTTACA TCAAGCGGCT GATAGAAGCT     300

CTTGGTTTCA AAGTGCTGGA GCTGGAGGGA TACGAAGCAG ACGATATCAT CGCCACGCTT     360

GCAGTCAGGG CTGCACGTTT TTTGATGAGA TTTTCATTAA TAACCGGTGA CAAGGATATG     420

CTTCAACTTG TAAACGAGAA GATAAAGGTC TGGAGAATCG TCAAGGGGAT ATCGGATCTT     480

GAGCTTTACG ATTCGAAAAA GGTGAAAGAA AGATACGGTG TGGAACCACA TCAGATACCG     540

GATCTTCTAG CACTGACGGG AGACGACATA GACAACATTC CCGGTGTAAC GGGAATAGGT     600

GAAAAGACCG CTGTACAGCT TCTCGGCAAG TATAGAAATC TTGAATACAT TCTGGAGCAT     660
```

```
GCCCGTGAAC TCCCCCAGAG AGTGAGAAAG GCTCTCTTGA GAGACAGGGA AGTTGCCATC      720

CTCAGTAAAA AACTTGCAAC TCTGGTGACG AACGCACCTG TTGAAGTGGA CTGGGAAGAG      780

ATGAAATACA GAGGATACGA CAAGAGAAAA CTACTTCCGA TATTGAAAGA ACTGGAGTTT      840

GCTTCCATCA TGAAGGAACT TCAACTGTAC GAAGAAGCAG AACCCACCGG ATACGAAATC      900

GTGAAGGATC ATAAGACCTT CGAAGATCTC ATCGAAAAGC TGAAGGAGGT TCCATCTTTT      960

GCCCTGGACC TTGAAACGTC CTCCCTTGAC CCGTTCAACT GTGAGATAGT CGGCATCTCC     1020

GTGTCGTTCA AACCGAAAAC AGCTTATTAC ATTCCACTTC ATCACAGAAA CGCCCAGAAT     1080

CTTGATGAAA CACTGGTGCT GTCGAAGTTG AAAGAGATCC TCGAAGACCC GTCTTCGAAG     1140

ATTGTGGGTC AGAACCTGAA GTACGACTAC AAGGTTCTTA TGGTAAAGGG TATATCGCCA     1200

GTTTATCCGC ATTTTGACAC GATGATAGCT GCATATTTGC TGGAGCCAAA CGAGAAAAAA     1260

TTCAATCTCG AAGATCTGTC TTTGAAATTT CTCGGATACA AAATGACGTC TTATCAGGAA     1320

CTGATGTCGT TTTCCTCACC ACTTTTTGGT TTCAGCTTTG CGGATGTTCC GGTAGACAAG     1380

GCTGCGAACT ACTCCTGCGA GGATGCAGAC ATCACTTATA GGCTCTACAA GATACTCAGC     1440

ATGAAGCTCC ATGAAGCGGA ACTTGAGAAC GTCTTCTACA GGATAGAGAT GCCGTTGGTG     1500

AACGTTCTTG CACGCATGGA ATTGAACGGG GTGTATGTGG ACACAGAATT CCTGAAAAAG     1560

CTCTCGGAGG AGTACGGCAA AAAGCTCGAG GAACTGGCCG AAAAAATCTA CCAGATAGCA     1620

GGTGAGCCCT TCAACATCAA TTCTCCAAAA CAGGTTTCAA AGATCCTTTT TGAGAAGCTG     1680

GGAATAAAAC CCCGTGGAAA AACGACAAAA ACAGGAGAGT ACTCTACCAG GATAGAGGTG     1740

TTGGAAGAGA TAGCGAATGA GCACGAGATA GTACCCCTCA TTCTCGAGTA CAGAAAGATC     1800

CAGAAACTGA AATCGACCTA CATAGACACC CTTCCGAAAC TTGTGAACCC GAAAACCGGA     1860

AGAATTCATG CATCTTTCCA CCAGACGGGT ACCGCCACTG GCAGGTTGAG TAGCAGTGAT     1920

CCAAATCTTC AGAATCTTCC GACAAAGAGC GAAGAGGGAA AAGAAATTAG AAAAGCGATT     1980

GTGCCCCAGG ATCCAGACTG GTGGATCGTC AGTGCGGATT ATTCCCAAAT GAACTCAGA     2040

ATCCTCGCTC ATCTCAGTGG TGATGAGAAC CTTGTGAAGG CCTTCGAGGA GGGCATCGAT     2100

GTGCACACCT TGACTGCCTC CAGGATCTAC AACGTAAAGC CAGAAGAAGT GAACGAAGAA     2160

ATGCGACGGG TTGGAAAGAT GGTGAACTTC TCTATAATAT ACGGTGTCAC ACCGTACGGT     2220

CTTTCTGTGA GACTTGGAAT ACCGGTTAAA GAAGCAGAAA AGATGATTAT CAGCTATTTC     2280

ACACTGTATC CAAAGGTGCG AAGCTACATC CAGCAGGTTG TTGCAGAGGC AAAAGAGAAG     2340

GGCTACGTCA GGACTCTCTT TGGAAGAAAA AGAGATATTC CCCAGCTCAT GGCAAGGGAC     2400

AAGAACACCC AGTCCGAAGG CGAAAGAATC GCAATAAACA CCCCCATTCA GGGAACGGCG     2460

GCAGATATAA TAAAATTGGC TATGATAGAT ATAGACGAGG AGCTGAGAAA AGAAACATG     2520

AAATCCAGAA TGATCATTCA GGTTCATGAC GAACTGGTCT TCGAGGTTCC CGATGAGGAA     2580

AAAGAAGAAC TAGTTGATCT GGTGAAGAAC AAAAATGACAA ATGTGGTGAA ACTCTCTGTG     2640

CCTCTTGAGG TTGACATAAG CATCGGAAAA AGCTGGTCTT GA                        2682
```

(2) INFORMATION FOR SEQ ID NO:2:

(i) SEQUENCE CHARACTERISTICS:
        (A) LENGTH: 893 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:2:

```
Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
            20                  25                  30

Asn Ala Val Tyr Gly Val Ala Arg Met Leu Val Lys Phe Ile Lys Glu
            35                  40                  45

His Ile Ile Pro Glu Lys Asp Tyr Ala Ala Val Ala Phe Asp Lys Lys
        50                  55                  60

Ala Ala Thr Phe Arg His Lys Leu Leu Val Ser Asp Lys Ala Gln Arg
65                  70                  75                  80

Pro Lys Thr Pro Ala Leu Leu Val Gln Gln Leu Pro Tyr Ile Lys Arg
                85                  90                  95

Leu Ile Glu Ala Leu Gly Phe Lys Val Leu Glu Leu Glu Gly Tyr Glu
            100                 105                 110

Ala Asp Asp Ile Ile Ala Thr Leu Ala Val Arg Ala Ala Arg Phe Leu
            115                 120                 125

Met Arg Phe Ser Leu Ile Thr Gly Asp Lys Asp Met Leu Gln Leu Val
        130                 135                 140

Asn Glu Lys Ile Lys Val Trp Arg Ile Val Lys Gly Ile Ser Asp Leu
145                 150                 155                 160

Glu Leu Tyr Asp Ser Lys Lys Val Lys Glu Arg Tyr Gly Val Glu Pro
                165                 170                 175

His Gln Ile Pro Asp Leu Leu Ala Leu Thr Gly Asp Asp Ile Asp Asn
            180                 185                 190

Ile Pro Gly Val Thr Gly Ile Gly Glu Lys Thr Ala Val Gln Leu Leu
            195                 200                 205

Gly Lys Tyr Arg Asn Leu Glu Tyr Ile Leu Glu His Ala Arg Glu Leu
        210                 215                 220

Pro Gln Arg Val Arg Lys Ala Leu Leu Arg Asp Arg Glu Val Ala Ile
225                 230                 235                 240

Leu Ser Lys Lys Leu Ala Thr Leu Val Thr Asn Ala Pro Val Glu Val
                245                 250                 255

Asp Trp Glu Glu Met Lys Tyr Arg Gly Tyr Asp Lys Arg Lys Leu Leu
            260                 265                 270

Pro Ile Leu Lys Glu Leu Glu Phe Ala Ser Ile Met Lys Glu Leu Gln
            275                 280                 285

Leu Tyr Glu Glu Ala Glu Pro Thr Gly Tyr Glu Ile Val Lys Asp His
        290                 295                 300

Lys Thr Phe Glu Asp Leu Ile Glu Lys Leu Lys Glu Val Pro Ser Phe
305                 310                 315                 320

Ala Leu Asp Leu Glu Thr Ser Ser Leu Asp Pro Phe Asn Cys Glu Ile
                325                 330                 335

Val Gly Ile Ser Val Ser Phe Lys Pro Lys Thr Ala Tyr Tyr Ile Pro
            340                 345                 350

Leu His His Arg Asn Ala Gln Asn Leu Asp Glu Thr Leu Val Leu Ser
            355                 360                 365

Lys Leu Lys Glu Ile Leu Glu Asp Pro Ser Ser Lys Ile Val Gly Gln
        370                 375                 380

Asn Leu Lys Tyr Asp Tyr Lys Val Leu Met Val Lys Gly Ile Ser Pro
385                 390                 395                 400

Val Tyr Pro His Phe Asp Thr Met Ile Ala Ala Tyr Leu Leu Glu Pro
```

```
                        405                     410                     415
    Asn Glu Lys Lys Phe Asn Leu Glu Asp Leu Ser Leu Lys Phe Leu Gly
                    420                     425                     430

Tyr Lys Met Thr Ser Tyr Gln Glu Leu Met Ser Phe Ser Ser Pro Leu
                    435                     440                     445

Phe Gly Phe Ser Phe Ala Asp Val Pro Val Asp Lys Ala Ala Asn Tyr
                    450                     455                     460

Ser Cys Glu Asp Ala Asp Ile Thr Tyr Arg Leu Tyr Lys Ile Leu Ser
    465                     470                     475                     480

Met Lys Leu His Glu Ala Glu Leu Glu Asn Val Phe Tyr Arg Ile Glu
                    485                     490                     495

Met Pro Leu Val Asn Val Leu Ala Arg Met Glu Leu Asn Gly Val Tyr
                    500                     505                     510

Val Asp Thr Glu Phe Leu Lys Lys Leu Ser Glu Glu Tyr Gly Lys Lys
                    515                     520                     525

Leu Glu Glu Leu Ala Glu Lys Ile Tyr Gln Ile Ala Gly Glu Pro Phe
                    530                     535                     540

Asn Ile Asn Ser Pro Lys Gln Val Ser Lys Ile Leu Phe Glu Lys Leu
    545                     550                     555                     560

Gly Ile Lys Pro Arg Gly Lys Thr Thr Lys Thr Gly Glu Tyr Ser Thr
                    565                     570                     575

Arg Ile Glu Val Leu Glu Glu Ile Ala Asn Glu His Glu Ile Val Pro
                    580                     585                     590

Leu Ile Leu Glu Tyr Arg Lys Ile Gln Lys Leu Lys Ser Thr Tyr Ile
                    595                     600                     605

Asp Thr Leu Pro Lys Leu Val Asn Pro Lys Thr Gly Arg Ile His Ala
                    610                     615                     620

Ser Phe His Gln Thr Gly Thr Ala Thr Gly Arg Leu Ser Ser Ser Asp
    625                     630                     635                     640

Pro Asn Leu Gln Asn Leu Pro Thr Lys Ser Glu Gly Lys Glu Ile
                    645                     650                     655

Arg Lys Ala Ile Val Pro Gln Asp Pro Asp Trp Trp Ile Val Ser Ala
                    660                     665                     670

Asp Tyr Ser Gln Ile Glu Leu Arg Ile Leu Ala His Leu Ser Gly Asp
                    675                     680                     685

Glu Asn Leu Val Lys Ala Phe Glu Glu Gly Ile Asp Val His Thr Leu
                    690                     695                     700

Thr Ala Ser Arg Ile Tyr Asn Val Lys Pro Glu Glu Val Asn Glu Glu
    705                     710                     715                     720

Met Arg Arg Val Gly Lys Met Val Asn Phe Ser Ile Ile Tyr Gly Val
                    725                     730                     735

Thr Pro Tyr Gly Leu Ser Val Arg Leu Gly Ile Pro Val Lys Glu Ala
                    740                     745                     750

Glu Lys Met Ile Ile Ser Tyr Phe Thr Leu Tyr Pro Lys Val Arg Ser
                    755                     760                     765

Tyr Ile Gln Gln Val Val Ala Glu Ala Lys Glu Lys Gly Tyr Val Arg
                    770                     775                     780

Thr Leu Phe Gly Arg Lys Arg Asp Ile Pro Gln Leu Met Ala Arg Asp
    785                     790                     795                     800

Lys Asn Thr Gln Ser Glu Gly Glu Arg Ile Ala Ile Asn Thr Pro Ile
                    805                     810                     815

Gln Gly Thr Ala Ala Asp Ile Ile Lys Leu Ala Met Ile Asp Ile Asp
                    820                     825                     830
```

```
Glu Glu Leu Arg Lys Arg Asn Met Lys Ser Arg Met Ile Ile Gln Val
        835                 840                 845

His Asp Glu Leu Val Phe Glu Val Pro Asp Glu Glu Lys Glu Glu Leu
850                 855                 860

Val Asp Leu Val Lys Asn Lys Met Thr Asn Val Val Lys Leu Ser Val
865                 870                 875                 880

Pro Leu Glu Val Asp Ile Ser Ile Gly Lys Ser Trp Ser
                885                 890
```

(2) INFORMATION FOR SEQ ID NO:3:

(i) SEQUENCE CHARACTERISTICS:
        (A) LENGTH: 677 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:3:

```
Met Ser Leu His Ala Arg Glu Leu Pro Gln Arg Val Arg Lys Ala Leu
1               5                   10                  15

Leu Arg Asp Arg Glu Val Ala Ile Leu Ser Lys Lys Leu Ala Thr Leu
            20                  25                  30

Val Thr Asn Ala Pro Val Glu Val Asp Trp Glu Glu Met Lys Tyr Arg
            35                  40                  45

Gly Tyr Asp Lys Arg Lys Leu Leu Pro Ile Leu Lys Glu Leu Glu Phe
50                  55                  60

Ala Ser Ile Met Lys Glu Leu Gln Leu Tyr Glu Glu Ala Glu Pro Thr
65                  70                  75                  80

Gly Tyr Glu Ile Val Lys Asp His Lys Thr Phe Glu Asp Leu Ile Glu
                85                  90                  95

Lys Leu Lys Glu Val Pro Ser Phe Ala Leu Ala Leu Glu Thr Ser Ser
                100                 105                 110

Leu Asp Pro Phe Asn Cys Glu Ile Val Gly Ile Ser Val Ser Phe Lys
            115                 120                 125

Pro Lys Thr Ala Tyr Tyr Ile Pro Leu His His Arg Asn Ala Gln Asn
130                 135                 140

Leu Asp Glu Thr Leu Val Leu Ser Lys Leu Lys Glu Ile Leu Glu Asp
145                 150                 155                 160

Pro Ser Ser Lys Ile Val Gly Gln Asn Leu Lys Tyr Asp Tyr Lys Val
                165                 170                 175

Leu Met Val Lys Gly Ile Ser Pro Val Tyr Pro His Phe Asp Thr Met
                180                 185                 190

Ile Ala Ala Tyr Leu Leu Glu Pro Asn Glu Lys Lys Phe Asn Leu Glu
            195                 200                 205

Asp Leu Ser Leu Lys Phe Leu Gly Tyr Lys Met Thr Ser Tyr Gln Glu
210                 215                 220

Leu Met Ser Phe Ser Ser Pro Leu Phe Gly Phe Ser Phe Ala Asp Val
225                 230                 235                 240

Pro Val Asp Lys Ala Ala Asn Tyr Ser Cys Glu Asp Ala Asp Ile Thr
                245                 250                 255

Tyr Arg Leu Tyr Lys Ile Leu Ser Met Lys Leu His Glu Ala Glu Leu
                260                 265                 270

Glu Asn Val Phe Tyr Arg Ile Glu Met Pro Leu Val Asn Val Leu Ala
            275                 280                 285
```

```
Arg Met Glu Leu Asn Gly Val Tyr Val Asp Thr Glu Phe Leu Lys Lys
    290                 295                 300

Leu Ser Glu Glu Tyr Gly Lys Lys Leu Glu Glu Leu Ala Glu Lys Ile
305                 310                 315                 320

Tyr Gln Ile Ala Gly Glu Pro Phe Asn Ile Asn Ser Pro Lys Gln Val
                325                 330                 335

Ser Lys Ile Leu Phe Glu Lys Leu Gly Ile Lys Pro Arg Gly Lys Thr
                340                 345                 350

Thr Lys Thr Gly Glu Tyr Ser Thr Arg Ile Glu Val Leu Glu Glu Ile
            355                 360                 365

Ala Asn Glu His Glu Ile Val Pro Leu Ile Leu Glu Tyr Arg Lys Ile
        370                 375                 380

Gln Lys Leu Lys Ser Thr Tyr Ile Asp Thr Leu Pro Lys Leu Val Asn
385                 390                 395                 400

Pro Lys Thr Gly Arg Ile His Ala Ser Phe His Gln Thr Gly Thr Ala
                405                 410                 415

Thr Gly Arg Leu Ser Ser Ser Asp Pro Asn Leu Gln Asn Leu Pro Thr
            420                 425                 430

Lys Ser Glu Glu Gly Lys Glu Ile Arg Lys Ala Ile Val Pro Gln Asp
        435                 440                 445

Pro Asp Trp Trp Ile Val Ser Ala Asp Tyr Ser Gln Ile Glu Leu Arg
    450                 455                 460

Ile Leu Ala His Leu Ser Gly Asp Glu Asn Leu Val Lys Ala Phe Glu
465                 470                 475                 480

Glu Gly Ile Asp Val His Thr Leu Thr Ala Ser Arg Ile Tyr Asn Val
                485                 490                 495

Lys Pro Glu Glu Val Asn Glu Glu Met Arg Arg Val Gly Lys Met Val
            500                 505                 510

Asn Phe Ser Ile Ile Tyr Gly Val Thr Pro Tyr Gly Leu Ser Val Arg
        515                 520                 525

Leu Gly Ile Pro Val Lys Glu Ala Glu Lys Met Ile Ile Ser Tyr Phe
    530                 535                 540

Thr Leu Tyr Pro Lys Val Arg Ser Tyr Ile Gln Gln Val Val Ala Glu
545                 550                 555                 560

Ala Lys Glu Lys Gly Tyr Val Arg Thr Leu Phe Gly Arg Lys Arg Asp
                565                 570                 575

Ile Pro Gln Leu Met Ala Arg Asp Lys Asn Thr Gln Ser Glu Gly Glu
            580                 585                 590

Arg Ile Ala Ile Asn Thr Pro Ile Gln Gly Thr Ala Ala Asp Ile Ile
        595                 600                 605

Lys Leu Ala Met Ile Asp Ile Asp Glu Glu Leu Arg Lys Arg Asn Met
610                 615                 620

Lys Ser Arg Met Ile Ile Gln Val His Asp Glu Leu Val Phe Glu Val
625                 630                 635                 640

Pro Asp Glu Glu Lys Glu Glu Leu Val Asp Leu Val Lys Asn Lys Met
                645                 650                 655

Thr Asn Val Val Lys Leu Ser Val Pro Leu Glu Val Asp Ile Ser Ile
            660                 665                 670

Gly Lys Ser Trp Ser
            675
```

(2) INFORMATION FOR SEQ ID NO:4:

(i) SEQUENCE CHARACTERISTICS:
    (A) LENGTH: 610 amino acids
    (B) TYPE: amino acid
    (C) STRANDEDNESS: Not Relevant
    (D) TOPOLOGY: Not Relevant (ii) MOLECULE TYPE: protein (xi) SEQUENCE DESCRIPTION: SEQ ID NO:4:

```
Met Lys Glu Leu Gln Leu Tyr Glu Glu Ala Glu Pro Thr Gly Tyr Glu
1               5                   10                  15

Ile Val Lys Asp His Lys Thr Phe Glu Asp Leu Ile Glu Lys Leu Lys
            20                  25                  30

Glu Val Pro Ser Phe Ala Leu Ala Leu Glu Thr Ser Ser Leu Asp Pro
        35                  40                  45

Phe Asn Cys Glu Ile Val Gly Ile Ser Val Ser Phe Lys Pro Lys Thr
50                  55                  60

Ala Tyr Tyr Ile Pro Leu His His Arg Asn Ala Gln Asn Leu Asp Glu
65                  70                  75                  80

Thr Leu Val Leu Ser Lys Leu Lys Glu Ile Leu Glu Asp Pro Ser Ser
                85                  90                  95

Lys Ile Val Gly Gln Asn Leu Lys Tyr Asp Tyr Lys Val Leu Met Val
            100                 105                 110

Lys Gly Ile Ser Pro Val Tyr Pro His Phe Asp Thr Met Ile Ala Ala
        115                 120                 125

Tyr Leu Leu Glu Pro Asn Glu Lys Lys Phe Asn Leu Glu Asp Leu Ser
        130                 135                 140

Leu Lys Phe Leu Gly Tyr Lys Met Thr Ser Tyr Gln Glu Leu Met Ser
145                 150                 155                 160

Phe Ser Ser Pro Leu Phe Gly Phe Ser Phe Ala Asp Val Pro Val Asp
                165                 170                 175

Lys Ala Ala Asn Tyr Ser Cys Glu Asp Ala Asp Ile Thr Tyr Arg Leu
            180                 185                 190

Tyr Lys Ile Leu Ser Met Lys Leu His Glu Ala Glu Leu Glu Asn Val
        195                 200                 205

Phe Tyr Arg Ile Glu Met Pro Leu Val Asn Val Leu Ala Arg Met Glu
        210                 215                 220

Leu Asn Gly Val Tyr Val Asp Thr Glu Phe Leu Lys Lys Leu Ser Glu
225                 230                 235                 240

Glu Tyr Gly Lys Lys Leu Glu Glu Leu Ala Glu Lys Ile Tyr Gln Ile
                245                 250                 255

Ala Gly Glu Pro Phe Asn Ile Asn Ser Pro Lys Gln Val Ser Lys Ile
            260                 265                 270

Leu Phe Glu Lys Leu Gly Ile Lys Pro Arg Gly Lys Thr Thr Lys Thr
        275                 280                 285

Gly Glu Tyr Ser Thr Arg Ile Glu Val Leu Glu Glu Ile Ala Asn Glu
        290                 295                 300

His Glu Ile Val Pro Leu Ile Leu Glu Tyr Arg Lys Ile Gln Lys Leu
305                 310                 315                 320

Lys Ser Thr Tyr Ile Asp Thr Leu Pro Lys Leu Val Asn Pro Lys Thr
                325                 330                 335

Gly Arg Ile His Ala Ser Phe His Gln Thr Gly Thr Ala Thr Gly Arg
            340                 345                 350

Leu Ser Ser Ser Asp Pro Asn Leu Gln Asn Leu Pro Thr Lys Ser Glu
        355                 360                 365
```

```
Glu Gly Lys Glu Ile Arg Lys Ala Ile Val Pro Gln Asp Pro Asp Trp
    370                 375                 380

Trp Ile Val Ser Ala Asp Tyr Ser Gln Ile Glu Leu Arg Ile Leu Ala
385                 390                 395                 400

His Leu Ser Gly Asp Glu Asn Leu Val Lys Ala Phe Glu Glu Gly Ile
                405                 410                 415

Asp Val His Thr Leu Thr Ala Ser Arg Ile Tyr Asn Val Lys Pro Glu
            420                 425                 430

Glu Val Asn Glu Glu Met Arg Arg Val Gly Lys Met Val Asn Phe Ser
        435                 440                 445

Ile Ile Tyr Gly Val Thr Pro Tyr Gly Leu Ser Val Arg Leu Gly Ile
    450                 455                 460

Pro Val Lys Glu Ala Glu Lys Met Ile Ile Ser Tyr Phe Thr Leu Tyr
465                 470                 475                 480

Pro Lys Val Arg Ser Tyr Ile Gln Gln Val Val Ala Glu Ala Lys Glu
                485                 490                 495

Lys Gly Tyr Val Arg Thr Leu Phe Gly Arg Lys Arg Asp Ile Pro Gln
            500                 505                 510

Leu Met Ala Arg Asp Lys Asn Thr Gln Ser Glu Gly Glu Arg Ile Ala
        515                 520                 525

Ile Asn Thr Pro Ile Gln Gly Thr Ala Ala Asp Ile Ile Lys Leu Ala
    530                 535                 540

Met Ile Asp Ile Asp Glu Glu Leu Arg Lys Arg Asn Met Lys Ser Arg
545                 550                 555                 560

Met Ile Ile Gln Val His Asp Glu Leu Val Phe Glu Val Pro Asp Glu
                565                 570                 575

Glu Lys Glu Glu Leu Val Asp Leu Val Lys Asn Lys Met Thr Asn Val
            580                 585                 590

Val Lys Leu Ser Val Pro Leu Glu Val Asp Ile Ser Ile Gly Lys Ser
        595                 600                 605

Trp Ser
    610

(2) INFORMATION FOR SEQ ID NO:5:

(i) SEQUENCE CHARACTERISTICS:
        (A) LENGTH: 708 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:5:

Met Asn Ser Ser Ser Val Pro Ile Pro Gly Val Thr Gly Ile Gly Glu
1               5                   10                  15

Lys Thr Ala Val Gln Leu Leu Gly Lys Tyr Arg Asn Leu Glu Tyr Ile
            20                  25                  30

Leu Glu His Ala Arg Glu Leu Pro Gln Arg Val Arg Lys Ala Leu Leu
        35                  40                  45

Arg Asp Arg Glu Val Ala Ile Leu Ser Lys Lys Leu Ala Thr Leu Val
    50                  55                  60

Thr Asn Ala Pro Val Glu Val Asp Trp Glu Glu Met Lys Tyr Arg Gly
65                  70                  75                  80

Tyr Asp Lys Arg Lys Leu Leu Pro Ile Leu Lys Glu Leu Glu Phe Ala
                85                  90                  95
```

```
Ser Ile Met Lys Glu Leu Gln Leu Tyr Glu Glu Ala Glu Pro Thr Gly
            100                 105                 110
Tyr Glu Ile Val Lys Asp His Lys Thr Phe Glu Asp Leu Ile Glu Lys
            115                 120                 125
Leu Lys Glu Val Pro Ser Phe Ala Leu Ala Leu Glu Thr Ser Ser Leu
130                 135                 140
Asp Pro Phe Asn Cys Glu Ile Val Gly Ile Ser Val Ser Phe Lys Pro
145                 150                 155                 160
Lys Thr Ala Tyr Tyr Ile Pro Leu His His Arg Asn Ala Gln Asn Leu
                165                 170                 175
Asp Glu Thr Leu Val Leu Ser Lys Leu Lys Glu Ile Leu Glu Asp Pro
                180                 185                 190
Ser Ser Lys Ile Val Gly Gln Asn Leu Lys Tyr Asp Tyr Lys Val Leu
            195                 200                 205
Met Val Lys Gly Ile Ser Pro Val Tyr Pro His Phe Asp Thr Met Ile
            210                 215                 220
Ala Ala Tyr Leu Leu Glu Pro Asn Glu Lys Lys Phe Asn Leu Glu Asp
225                 230                 235                 240
Leu Ser Leu Lys Phe Leu Gly Tyr Lys Met Thr Ser Tyr Gln Glu Leu
                245                 250                 255
Met Ser Phe Ser Ser Pro Leu Phe Gly Phe Ser Phe Ala Asp Val Pro
                260                 265                 270
Val Asp Lys Ala Ala Asn Tyr Ser Cys Glu Asp Ala Asp Ile Thr Tyr
            275                 280                 285
Arg Leu Tyr Lys Ile Leu Ser Met Lys Leu His Glu Ala Glu Leu Glu
            290                 295                 300
Asn Val Phe Tyr Arg Ile Glu Met Pro Leu Val Asn Val Leu Ala Arg
305                 310                 315                 320
Met Glu Leu Asn Gly Val Tyr Val Asp Thr Glu Phe Leu Lys Lys Leu
                325                 330                 335
Ser Glu Glu Tyr Gly Lys Lys Leu Glu Glu Leu Ala Glu Lys Ile Tyr
                340                 345                 350
Gln Ile Ala Gly Glu Pro Phe Asn Ile Asn Ser Pro Lys Gln Val Ser
            355                 360                 365
Lys Ile Leu Phe Glu Lys Leu Gly Ile Lys Pro Arg Gly Lys Thr Thr
            370                 375                 380
Lys Thr Gly Glu Tyr Ser Thr Arg Ile Glu Val Leu Glu Glu Ile Ala
385                 390                 395                 400
Asn Glu His Glu Ile Val Pro Leu Ile Leu Glu Tyr Arg Lys Ile Gln
                405                 410                 415
Lys Leu Lys Ser Thr Tyr Ile Asp Thr Leu Pro Lys Leu Val Asn Pro
                420                 425                 430
Lys Thr Gly Arg Ile His Ala Ser Phe His Gln Thr Gly Thr Ala Thr
            435                 440                 445
Gly Arg Leu Ser Ser Ser Asp Pro Asn Leu Gln Asn Leu Pro Thr Lys
            450                 455                 460
Ser Glu Glu Gly Lys Glu Ile Arg Lys Ala Ile Val Pro Gln Asp Pro
465                 470                 475                 480
Asp Trp Trp Ile Val Ser Ala Asp Tyr Ser Gln Ile Glu Leu Arg Ile
                485                 490                 495
Leu Ala His Leu Ser Gly Asp Glu Asn Leu Val Lys Ala Phe Glu Glu
                500                 505                 510
Gly Ile Asp Val His Thr Leu Thr Ala Ser Arg Ile Tyr Asn Val Lys
```

```
                515                 520                 525
Pro Glu Glu Val Asn Glu Glu Met Arg Arg Val Gly Lys Met Val Asn
        530                 535                 540

Phe Ser Ile Ile Tyr Gly Val Thr Pro Tyr Gly Leu Ser Val Arg Leu
545                 550                 555                 560

Gly Ile Pro Val Lys Glu Ala Glu Lys Met Ile Ile Ser Tyr Phe Thr
                565                 570                 575

Leu Tyr Pro Lys Val Arg Ser Tyr Ile Gln Gln Val Val Ala Glu Ala
                580                 585                 590

Lys Glu Lys Gly Tyr Val Arg Thr Leu Phe Gly Arg Lys Arg Asp Ile
                595                 600                 605

Pro Gln Leu Met Ala Arg Asp Lys Asn Thr Gln Ser Glu Gly Glu Arg
        610                 615                 620

Ile Ala Ile Asn Thr Pro Ile Gln Gly Thr Ala Ala Asp Ile Ile Lys
625                 630                 635                 640

Leu Ala Met Ile Asp Ile Asp Glu Glu Leu Arg Lys Arg Asn Met Lys
                645                 650                 655

Ser Arg Met Ile Ile Gln Val His Asp Glu Leu Val Phe Glu Val Pro
                660                 665                 670

Asp Glu Glu Lys Glu Glu Leu Val Asp Leu Val Lys Asn Lys Met Thr
        675                 680                 685

Asn Val Val Lys Leu Ser Val Pro Leu Glu Val Asp Ile Ser Ile Gly
        690                 695                 700

Lys Ser Trp Ser
705

(2) INFORMATION FOR SEQ ID NO:6:

(i) SEQUENCE CHARACTERISTICS:
        (A) LENGTH: 893 amino acids
        (B) TYPE: amino acid
        (C) STRANDEDNESS: Not Relevant
        (D) TOPOLOGY: Not Relevant (ii) MOLECULE TYPE: peptide (xi) SEQUENCE DESCRIPTION: SEQ ID NO:6:

Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
                20                  25                  30

Asn Ala Val Tyr Gly Val Ala Arg Met Leu Val Lys Phe Ile Lys Glu
                35                  40                  45

His Ile Ile Pro Glu Lys Asp Tyr Ala Ala Val Ala Phe Asp Lys Lys
        50                  55                  60

Ala Ala Thr Phe Arg His Lys Leu Leu Val Ser Asp Lys Ala Gln Arg
65                  70                  75                  80

Pro Lys Thr Pro Ala Leu Leu Val Gln Gln Leu Pro Tyr Ile Lys Arg
                85                  90                  95

Leu Ile Glu Ala Leu Gly Phe Lys Val Leu Glu Leu Glu Gly Tyr Glu
                100                 105                 110

Ala Asp Asp Ile Ile Ala Thr Leu Ala Val Arg Ala Ala Arg Phe Leu
        115                 120                 125

Met Arg Phe Ser Leu Ile Thr Gly Ala Lys Asp Met Leu Gln Leu Val
        130                 135                 140

Asn Glu Lys Ile Lys Val Trp Arg Ile Val Lys Gly Ile Ser Asp Leu
```

```
            145                 150                 155                 160
Glu Leu Tyr Asp Ser Lys Lys Val Lys Glu Arg Tyr Gly Val Glu Pro
                165                 170                 175
His Gln Ile Pro Asp Leu Leu Ala Leu Thr Gly Asp Asp Ile Asp Asn
                180                 185                 190
Ile Pro Gly Val Thr Gly Ile Gly Glu Lys Thr Ala Val Gln Leu Leu
                195                 200                 205
Gly Lys Tyr Arg Asn Leu Glu Tyr Ile Leu Glu His Ala Arg Glu Leu
        210                 215                 220
Pro Gln Arg Val Arg Lys Ala Leu Leu Arg Asp Arg Glu Val Ala Ile
225                 230                 235                 240
Leu Ser Lys Lys Leu Ala Thr Leu Val Thr Asn Ala Pro Val Glu Val
                245                 250                 255
Asp Trp Glu Glu Met Lys Tyr Arg Gly Tyr Asp Lys Arg Lys Leu Leu
                260                 265                 270
Pro Ile Leu Lys Glu Leu Glu Phe Ala Ser Ile Met Lys Glu Leu Gln
                275                 280                 285
Leu Tyr Glu Glu Ala Glu Pro Thr Gly Tyr Glu Ile Val Lys Asp His
        290                 295                 300
Lys Thr Phe Glu Asp Leu Ile Glu Lys Leu Lys Glu Val Pro Ser Phe
305                 310                 315                 320
Ala Leu Ala Leu Glu Thr Ser Ser Leu Asp Pro Phe Asn Cys Glu Ile
                325                 330                 335
Val Gly Ile Ser Val Ser Phe Lys Pro Lys Thr Ala Tyr Tyr Ile Pro
                340                 345                 350
Leu His His Arg Asn Ala Gln Asn Leu Asp Glu Thr Leu Val Leu Ser
                355                 360                 365
Lys Leu Lys Glu Ile Leu Glu Asp Pro Ser Ser Lys Ile Val Gly Gln
        370                 375                 380
Asn Leu Lys Tyr Asp Tyr Lys Val Leu Met Val Lys Gly Ile Ser Pro
385                 390                 395                 400
Val Tyr Pro His Phe Asp Thr Met Ile Ala Ala Tyr Leu Leu Glu Pro
                405                 410                 415
Asn Glu Lys Lys Phe Asn Leu Glu Asp Leu Ser Leu Lys Phe Leu Gly
                420                 425                 430
Tyr Lys Met Thr Ser Tyr Gln Glu Leu Met Ser Phe Ser Ser Pro Leu
                435                 440                 445
Phe Gly Phe Ser Phe Ala Asp Val Pro Val Asp Lys Ala Ala Asn Tyr
        450                 455                 460
Ser Cys Glu Asp Ala Asp Ile Thr Tyr Arg Leu Tyr Lys Ile Leu Ser
465                 470                 475                 480
Met Lys Leu His Glu Ala Glu Leu Glu Asn Val Phe Tyr Arg Ile Glu
                485                 490                 495
Met Pro Leu Val Asn Val Leu Ala Arg Met Glu Leu Asn Gly Val Tyr
                500                 505                 510
Val Asp Thr Glu Phe Leu Lys Lys Leu Ser Glu Glu Tyr Gly Lys Lys
                515                 520                 525
Leu Glu Glu Leu Ala Glu Lys Ile Tyr Gln Ile Ala Gly Glu Pro Phe
        530                 535                 540
Asn Ile Asn Ser Pro Lys Gln Val Ser Lys Ile Leu Phe Glu Lys Leu
545                 550                 555                 560
Gly Ile Lys Pro Arg Gly Lys Thr Thr Lys Thr Gly Glu Tyr Ser Thr
                565                 570                 575
```

```
Arg Ile Glu Val Leu Glu Ile Ala Asn Glu His Glu Ile Val Pro
            580                 585                 590

Leu Ile Leu Glu Tyr Arg Lys Ile Gln Lys Leu Lys Ser Thr Tyr Ile
            595                 600                 605

Asp Thr Leu Pro Lys Leu Val Asn Pro Lys Thr Gly Arg Ile His Ala
            610                 615                 620

Ser Phe His Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
            645                 650                 655

Arg Lys Ala Ile Val Pro Gln Asp Pro Asp Trp Trp Ile Val Ser Ala
            660                 665                 670

Asp Tyr Ser Gln Ile Glu Leu Arg Ile Leu Ala His Leu Ser Gly Asp
            675                 680                 685

Glu Asn Leu Val Lys Ala Phe Glu Glu Gly Ile Asp Val His Thr Leu
            690                 695                 700

Thr Ala Ser Arg Ile Tyr Asn Val Lys Pro Glu Glu Val Asn Glu Glu
705                 710                 715                 720

Met Arg Arg Val Gly Lys Met Val Asn Phe Ser Ile Ile Tyr Gly Val
            725                 730                 735

Thr Pro Tyr Gly Leu Ser Val Arg Leu Gly Ile Pro Val Lys Glu Ala
            740                 745                 750

Glu Lys Met Ile Ile Ser Tyr Phe Thr Leu Tyr Pro Lys Val Arg Ser
            755                 760                 765

Tyr Ile Gln Gln Val Val Ala Glu Ala Lys Lys Gly Tyr Val Arg
            770                 775                 780

Thr Leu Phe Gly Arg Lys Arg Asp Ile Pro Gln Leu Met Ala Arg Asp
785                 790                 795                 800

Lys Asn Thr Gln Ser Glu Gly Glu Arg Ile Ala Ile Asn Thr Pro Ile
            805                 810                 815

Gln Gly Thr Ala Ala Asp Ile Ile Lys Leu Ala Met Ile Asp Ile Asp
            820                 825                 830

Glu Glu Leu Arg Lys Arg Asn Met Lys Ser Arg Met Ile Ile Gln Val
            835                 840                 845

His Asp Glu Leu Val Phe Glu Val Pro Asp Glu Glu Lys Glu Glu Leu
            850                 855                 860

Val Asp Leu Val Lys Asn Lys Met Thr Asn Val Val Lys Leu Ser Val
865                 870                 875                 880

Pro Leu Glu Val Asp Ile Ser Ile Gly Lys Ser Trp Ser
            885                 890

(2) INFORMATION FOR SEQ ID NO:7:

(i) SEQUENCE CHARACTERISTICS:
        (A) LENGTH: 893 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:7:

Met Ala Arg Leu Phe Leu Phe Ala Gly Thr Ala Leu Ala Tyr Arg Ala
1               5                   10                  15

Tyr Tyr Ala Leu Asp Arg Ser Leu Ser Thr Ser Thr Gly Ile Pro Thr
            20                  25                  30
```

-continued

```
Asn Ala Val Tyr Gly Val Ala Arg Met Leu Val Lys Phe Ile Lys Glu
             35                  40                  45
His Ile Ile Pro Glu Lys Asp Tyr Ala Ala Val Ala Phe Asp Lys Lys
 50                  55                  60
Ala Ala Thr Phe Arg His Lys Leu Leu Val Ser Asp Lys Ala Gln Arg
 65                  70                  75                  80
Pro Lys Thr Pro Ala Leu Leu Val Gln Gln Leu Pro Tyr Ile Lys Arg
                 85                  90                  95
Leu Ile Glu Ala Leu Gly Phe Lys Val Leu Glu Leu Glu Gly Tyr Glu
                100                 105                 110
Ala Asp Asp Ile Ile Ala Thr Leu Ala Val Arg Ala Ala Arg Phe Leu
                115                 120                 125
Met Arg Phe Ser Leu Ile Thr Gly Asp Lys Asp Met Leu Gln Leu Val
            130                 135                 140
Asn Glu Lys Ile Lys Val Trp Arg Ile Val Lys Gly Ile Ser Asp Leu
145                 150                 155                 160
Glu Leu Tyr Asp Ser Lys Lys Val Lys Glu Arg Tyr Gly Val Glu Pro
                165                 170                 175
His Gln Ile Pro Asp Leu Leu Ala Leu Thr Gly Asp Asp Ile Asp Asn
                180                 185                 190
Ile Pro Gly Val Thr Gly Ile Gly Glu Lys Thr Ala Val Gln Leu Leu
                195                 200                 205
Gly Lys Tyr Arg Asn Leu Glu Tyr Ile Leu Glu His Ala Arg Glu Leu
            210                 215                 220
Pro Gln Arg Val Arg Lys Ala Leu Leu Arg Asp Arg Glu Val Ala Ile
225                 230                 235                 240
Leu Ser Lys Lys Leu Ala Thr Leu Val Thr Asn Ala Pro Val Glu Val
                245                 250                 255
Asp Trp Glu Glu Met Lys Tyr Arg Gly Tyr Asp Lys Arg Lys Leu Leu
                260                 265                 270
Pro Ile Leu Lys Glu Leu Glu Phe Ala Ser Ile Met Lys Glu Leu Gln
                275                 280                 285
Leu Tyr Glu Glu Ala Glu Pro Thr Gly Tyr Glu Ile Val Lys Asp His
            290                 295                 300
Lys Thr Phe Glu Asp Leu Ile Glu Lys Leu Lys Glu Val Pro Ser Phe
305                 310                 315                 320
Ala Leu Ala Leu Glu Thr Ser Ser Leu Asp Pro Phe Asn Cys Glu Ile
                325                 330                 335
Val Gly Ile Ser Val Ser Phe Lys Pro Lys Thr Ala Tyr Tyr Ile Pro
                340                 345                 350
Leu His His Arg Asn Ala Gln Asn Leu Asp Glu Thr Leu Val Leu Ser
            355                 360                 365
Lys Leu Lys Glu Ile Leu Glu Asp Pro Ser Ser Lys Ile Val Gly Gln
            370                 375                 380
Asn Leu Lys Tyr Asp Tyr Lys Val Leu Met Val Lys Gly Ile Ser Pro
385                 390                 395                 400
Val Tyr Pro His Phe Asp Thr Met Ile Ala Ala Tyr Leu Leu Glu Pro
                405                 410                 415
Asn Glu Lys Lys Phe Asn Leu Glu Asp Leu Ser Leu Lys Phe Leu Gly
                420                 425                 430
Tyr Lys Met Thr Ser Tyr Gln Glu Leu Met Ser Phe Ser Ser Pro Leu
            435                 440                 445
```

-continued

```
Phe Gly Phe Ser Phe Ala Asp Val Pro Val Asp Lys Ala Ala Asn Tyr
    450                 455                 460
Ser Cys Glu Asp Ala Asp Ile Thr Tyr Arg Leu Tyr Lys Ile Leu Ser
465                 470                 475                 480
Met Lys Leu His Glu Ala Glu Leu Glu Asn Val Phe Tyr Arg Ile Glu
                485                 490                 495
Met Pro Leu Val Asn Val Leu Ala Arg Met Glu Leu Asn Gly Val Tyr
                500                 505                 510
Val Asp Thr Glu Phe Leu Lys Lys Leu Ser Glu Glu Tyr Gly Lys Lys
            515                 520                 525
Leu Glu Glu Leu Ala Glu Lys Ile Tyr Gln Ile Ala Gly Glu Pro Phe
        530                 535                 540
Asn Ile Asn Ser Pro Lys Gln Val Ser Lys Ile Leu Phe Glu Lys Leu
545                 550                 555                 560
Gly Ile Lys Pro Arg Gly Lys Thr Thr Lys Thr Gly Glu Tyr Ser Thr
                565                 570                 575
Arg Ile Glu Val Leu Glu Glu Ile Ala Asn Glu His Glu Ile Val Pro
                580                 585                 590
Leu Ile Leu Glu Tyr Arg Lys Ile Gln Lys Leu Lys Ser Thr Tyr Ile
            595                 600                 605
Asp Thr Leu Pro Lys Leu Val Asn Pro Lys Thr Gly Arg Ile His Ala
        610                 615                 620
Ser Phe His Gln Thr Gly Thr Ala Thr Gly Arg Leu Ser Ser Ser Asp
625                 630                 635                 640
Pro Asn Leu Gln Asn Leu Pro Thr Lys Ser Glu Gly Lys Glu Ile
                645                 650                 655
Arg Lys Ala Ile Val Pro Gln Asp Pro Asp Trp Trp Ile Val Ser Ala
                660                 665                 670
Asp Tyr Ser Gln Ile Glu Leu Arg Ile Leu Ala His Leu Ser Gly Asp
            675                 680                 685
Glu Asn Leu Val Lys Ala Phe Glu Glu Gly Ile Asp Val His Thr Leu
        690                 695                 700
Thr Ala Ser Arg Ile Tyr Asn Val Lys Pro Glu Glu Val Asn Glu Glu
705                 710                 715                 720
Met Arg Arg Val Gly Lys Met Val Asn Phe Ser Ile Ile Tyr Gly Val
                725                 730                 735
Thr Pro Tyr Gly Leu Ser Val Arg Leu Gly Ile Pro Val Lys Glu Ala
                740                 745                 750
Glu Lys Met Ile Ile Ser Tyr Phe Thr Leu Tyr Pro Lys Val Arg Ser
            755                 760                 765
Tyr Ile Gln Gln Val Val Ala Glu Ala Lys Glu Lys Gly Tyr Val Arg
        770                 775                 780
Thr Leu Phe Gly Arg Lys Arg Asp Ile Pro Gln Leu Met Ala Arg Asp
785                 790                 795                 800
Lys Asn Thr Gln Ser Glu Gly Glu Arg Ile Ala Ile Asn Thr Pro Ile
                805                 810                 815
Gln Gly Thr Ala Ala Asp Ile Ile Lys Leu Ala Met Ile Asp Ile Asp
                820                 825                 830
Glu Glu Leu Arg Lys Arg Asn Met Lys Ser Arg Met Ile Ile Gln Val
            835                 840                 845
His Asp Glu Leu Val Phe Glu Val Pro Asp Glu Glu Lys Glu Glu Leu
        850                 855                 860
Val Asp Leu Val Lys Asn Lys Met Thr Asn Val Val Lys Leu Ser Val
```

```
                865                 870                 875                 880

Pro Leu Glu Val Asp Ile Ser Ile Gly Lys Ser Trp Ser
                        885                 890
```

(2) INFORMATION FOR SEQ ID NO:8:

(i) SEQUENCE CHARACTERISTICS:
        (A) LENGTH: 893 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:8:

```
Met Ala Arg Leu Phe Leu Phe Asp Gly Thr Ala Leu Ala Tyr Arg Ala
1               5                   10                  15

Tyr Tyr Ala Leu Asp Arg Ser Leu Ser Thr Ser Thr Gly Ile Pro Thr
                20                  25                  30

Asn Ala Val Tyr Gly Val Ala Arg Met Leu Val Lys Phe Ile Lys Glu
            35                  40                  45

His Ile Ile Pro Glu Lys Asp Tyr Ala Ala Val Ala Phe Asp Lys Lys
        50                  55                  60

Ala Ala Thr Phe Arg His Lys Leu Leu Val Ser Asp Lys Ala Gln Arg
65                  70                  75                  80

Pro Lys Thr Pro Ala Leu Leu Val Gln Gln Leu Pro Tyr Ile Lys Arg
                85                  90                  95

Leu Ile Glu Ala Leu Gly Phe Lys Val Leu Glu Leu Glu Gly Tyr Glu
                100                 105                 110

Ala Asp Asp Ile Ile Ala Thr Leu Ala Val Arg Ala Ala Arg Phe Leu
            115                 120                 125

Met Arg Phe Ser Leu Ile Thr Gly Asp Lys Asp Met Leu Gln Leu Val
        130                 135                 140

Asn Glu Lys Ile Lys Val Trp Arg Ile Val Lys Gly Ile Ser Asp Leu
145                 150                 155                 160

Glu Leu Tyr Asp Ser Lys Lys Val Lys Glu Arg Tyr Gly Val Glu Pro
                165                 170                 175

His Gln Ile Pro Asp Leu Leu Ala Leu Thr Gly Asp Asp Ile Asp Asn
                180                 185                 190

Ile Pro Asp Val Thr Gly Ile Gly Glu Lys Thr Ala Val Gln Leu Leu
            195                 200                 205

Gly Lys Tyr Arg Asn Leu Glu Tyr Ile Leu Glu His Ala Arg Glu Leu
        210                 215                 220

Pro Gln Arg Val Arg Lys Ala Leu Leu Arg Asp Arg Glu Val Ala Ile
225                 230                 235                 240

Leu Ser Lys Lys Leu Ala Thr Leu Val Thr Asn Ala Pro Val Glu Val
                245                 250                 255

Asp Trp Glu Glu Met Lys Tyr Arg Gly Tyr Asp Lys Arg Lys Leu Leu
                260                 265                 270

Pro Ile Leu Lys Glu Leu Glu Phe Ala Ser Ile Met Lys Glu Leu Gln
            275                 280                 285

Leu Tyr Glu Glu Ala Glu Pro Thr Gly Tyr Glu Ile Val Lys Asp His
        290                 295                 300

Lys Thr Phe Glu Asp Leu Ile Glu Lys Leu Lys Glu Val Pro Ser Phe
305                 310                 315                 320

Ala Leu Ala Leu Glu Thr Ser Ser Leu Asp Pro Phe Asn Cys Glu Ile
```

-continued

```
                        325                 330                 335
    Val Gly Ile Ser Val Ser Phe Lys Pro Lys Thr Ala Tyr Tyr Ile Pro
                    340                 345                 350
    Leu His His Arg Asn Ala Gln Asn Leu Asp Glu Thr Leu Val Leu Ser
                    355                 360                 365
    Lys Leu Lys Glu Ile Leu Glu Asp Pro Ser Ser Lys Ile Val Gly Gln
                370                 375                 380
    Asn Leu Lys Tyr Asp Tyr Lys Val Leu Met Val Lys Gly Ile Ser Pro
385                 390                 395                 400
    Val Tyr Pro His Phe Asp Thr Met Ile Ala Ala Tyr Leu Leu Glu Pro
                    405                 410                 415
    Asn Glu Lys Lys Phe Asn Leu Glu Asp Leu Ser Leu Lys Phe Leu Gly
                420                 425                 430
    Tyr Lys Met Thr Ser Tyr Gln Glu Leu Met Ser Phe Ser Ser Pro Leu
                    435                 440                 445
    Phe Gly Phe Ser Phe Ala Asp Val Pro Val Asp Lys Ala Ala Asn Tyr
                450                 455                 460
    Ser Cys Glu Asp Ala Asp Ile Thr Tyr Arg Leu Tyr Lys Ile Leu Ser
465                 470                 475                 480
    Met Lys Leu His Glu Ala Glu Leu Glu Asn Val Phe Tyr Arg Ile Glu
                    485                 490                 495
    Met Pro Leu Val Asn Val Leu Ala Arg Met Glu Leu Asn Gly Val Tyr
                    500                 505                 510
    Val Asp Thr Glu Phe Leu Lys Lys Leu Ser Glu Glu Tyr Gly Lys Lys
                    515                 520                 525
    Leu Glu Glu Leu Ala Glu Lys Ile Tyr Gln Ile Ala Gly Glu Pro Phe
                    530                 535                 540
    Asn Ile Asn Ser Pro Lys Gln Val Ser Lys Ile Leu Phe Glu Lys Leu
545                 550                 555                 560
    Gly Ile Lys Pro Arg Gly Lys Thr Thr Lys Thr Gly Glu Tyr Ser Thr
                    565                 570                 575
    Arg Ile Glu Val Leu Glu Glu Ile Ala Asn Glu His Glu Ile Val Pro
                    580                 585                 590
    Leu Ile Leu Glu Tyr Arg Lys Ile Gln Lys Leu Lys Ser Thr Tyr Ile
                    595                 600                 605
    Asp Thr Leu Pro Lys Leu Val Asn Pro Lys Thr Gly Arg Ile His Ala
                610                 615                 620
    Ser Phe His Gln Thr Gly Thr Ala Thr Gly Arg Leu Ser Ser Ser Asp
625                 630                 635                 640
    Pro Asn Leu Gln Asn Leu Pro Thr Lys Ser Glu Glu Gly Lys Glu Ile
                    645                 650                 655
    Arg Lys Ala Ile Val Pro Gln Asp Pro Asp Trp Trp Ile Val Ser Ala
                    660                 665                 670
    Asp Tyr Ser Gln Ile Glu Leu Arg Ile Leu Ala His Leu Ser Gly Asp
                    675                 680                 685
    Glu Asn Leu Val Lys Ala Phe Glu Glu Gly Ile Asp Val His Thr Leu
                    690                 695                 700
    Thr Ala Ser Arg Ile Tyr Asn Val Lys Pro Glu Glu Val Asn Glu Glu
705                 710                 715                 720
    Met Arg Arg Val Gly Lys Met Val Asn Phe Ser Ile Ile Tyr Gly Val
                    725                 730                 735
    Thr Pro Tyr Gly Leu Ser Val Arg Leu Gly Ile Pro Val Lys Glu Ala
                    740                 745                 750
```

```
Glu Lys Met Ile Ile Ser Tyr Phe Thr Leu Tyr Pro Lys Val Arg Ser
            755                 760                 765
Tyr Ile Gln Gln Val Val Ala Glu Ala Lys Lys Gly Tyr Val Arg
        770                 775                 780
Thr Leu Phe Gly Arg Lys Arg Asp Ile Pro Gln Leu Met Ala Arg Asp
785                 790                 795                 800
Lys Asn Thr Gln Ser Glu Gly Glu Arg Ile Ala Ile Asn Thr Pro Ile
                805                 810                 815
Gln Gly Thr Ala Ala Asp Ile Ile Lys Leu Ala Met Ile Asp Ile Asp
                820                 825                 830
Glu Glu Leu Arg Lys Arg Asn Met Lys Ser Arg Met Ile Ile Gln Val
                835                 840                 845
His Asp Glu Leu Val Phe Glu Val Pro Asp Glu Glu Lys Glu Glu Leu
        850                 855                 860
Val Asp Leu Val Lys Asn Lys Met Thr Asn Val Val Lys Leu Ser Val
865                 870                 875                 880
Pro Leu Glu Val Asp Ile Ser Ile Gly Lys Ser Trp Ser
                885                 890
```

(2) INFORMATION FOR SEQ ID NO:9:

(i) SEQUENCE CHARACTERISTICS:
        (A) LENGTH: 893 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:9:

```
Met Ala Arg Leu Phe Leu Phe Asp Gly Thr Ala Leu Ala Tyr Arg Ala
1               5                   10                  15
Tyr Tyr Ala Leu Asp Arg Ser Leu Ser Thr Ser Thr Gly Ile Pro Thr
                20                  25                  30
Asn Ala Val Tyr Asp Val Ala Arg Met Leu Val Lys Phe Ile Lys Glu
                35                  40                  45
His Ile Ile Pro Glu Lys Asp Tyr Ala Ala Val Ala Phe Asp Lys Lys
        50                  55                  60
Ala Ala Thr Phe Arg His Lys Leu Leu Val Ser Asp Lys Ala Gln Arg
65                  70                  75                  80
Pro Lys Thr Pro Ala Leu Leu Val Gln Gln Leu Pro Tyr Ile Lys Arg
                85                  90                  95
Leu Ile Glu Ala Leu Gly Phe Lys Val Leu Glu Leu Glu Gly Tyr Glu
                100                 105                 110
Ala Asp Asp Ile Ile Ala Thr Leu Ala Val Arg Ala Ala Arg Phe Leu
                115                 120                 125
Met Arg Phe Ser Leu Ile Thr Gly Asp Lys Asp Met Leu Gln Leu Val
        130                 135                 140
Asn Glu Lys Ile Lys Val Trp Arg Ile Val Lys Gly Ile Ser Asp Leu
145                 150                 155                 160
Glu Leu Tyr Asp Ser Lys Lys Val Lys Glu Arg Tyr Gly Val Glu Pro
                165                 170                 175
His Gln Ile Pro Asp Leu Leu Ala Leu Thr Gly Asp Asp Ile Asp Asn
                180                 185                 190
Ile Pro Gly Val Thr Gly Ile Gly Glu Lys Thr Ala Val Gln Leu Leu
        195                 200                 205
```

```
Gly Lys Tyr Arg Asn Leu Glu Tyr Ile Leu Glu His Ala Arg Glu Leu
    210                 215                 220

Pro Gln Arg Val Arg Lys Ala Leu Leu Arg Asp Arg Glu Val Ala Ile
225                 230                 235                 240

Leu Ser Lys Lys Leu Ala Thr Leu Val Thr Asn Ala Pro Val Glu Val
            245                 250                 255

Asp Trp Glu Glu Met Lys Tyr Arg Gly Tyr Asp Lys Arg Lys Leu Leu
                260                 265                 270

Pro Ile Leu Lys Glu Leu Glu Phe Ala Ser Ile Met Lys Glu Leu Gln
            275                 280                 285

Leu Tyr Glu Glu Ala Glu Pro Thr Gly Tyr Glu Ile Val Lys Asp His
    290                 295                 300

Lys Thr Phe Glu Asp Leu Ile Glu Lys Leu Lys Glu Val Pro Ser Phe
305                 310                 315                 320

Ala Leu Ala Leu Glu Thr Ser Ser Leu Asp Pro Phe Asn Cys Glu Ile
                325                 330                 335

Val Gly Ile Ser Val Ser Phe Lys Pro Lys Thr Ala Tyr Tyr Ile Pro
            340                 345                 350

Leu His His Arg Asn Ala Gln Asn Leu Asp Glu Thr Leu Val Leu Ser
    355                 360                 365

Lys Leu Lys Glu Ile Leu Glu Asp Pro Ser Ser Lys Ile Val Gly Gln
370                 375                 380

Asn Leu Lys Tyr Asp Tyr Lys Val Leu Met Val Lys Gly Ile Ser Pro
385                 390                 395                 400

Val Tyr Pro His Phe Asp Thr Met Ile Ala Ala Tyr Leu Leu Glu Pro
                405                 410                 415

Asn Glu Lys Lys Phe Asn Leu Glu Asp Leu Ser Leu Lys Phe Leu Gly
            420                 425                 430

Tyr Lys Met Thr Ser Tyr Gln Glu Leu Met Ser Phe Ser Ser Pro Leu
                435                 440                 445

Phe Gly Phe Ser Phe Ala Asp Val Pro Val Asp Lys Ala Ala Asn Tyr
    450                 455                 460

Ser Cys Glu Asp Ala Asp Ile Thr Tyr Arg Leu Tyr Lys Ile Leu Ser
465                 470                 475                 480

Met Lys Leu His Glu Ala Glu Leu Glu Asn Val Phe Tyr Arg Ile Glu
                485                 490                 495

Met Pro Leu Val Asn Val Leu Ala Arg Met Glu Leu Asn Gly Val Tyr
            500                 505                 510

Val Asp Thr Glu Phe Leu Lys Lys Leu Ser Glu Tyr Gly Lys Lys
    515                 520                 525

Leu Glu Glu Leu Ala Glu Lys Ile Tyr Gln Ile Ala Gly Glu Pro Phe
    530                 535                 540

Asn Ile Asn Ser Pro Lys Gln Val Ser Lys Ile Leu Phe Glu Lys Leu
545                 550                 555                 560

Gly Ile Lys Pro Arg Gly Lys Thr Thr Lys Thr Gly Glu Tyr Ser Thr
                565                 570                 575

Arg Ile Glu Val Leu Glu Glu Ile Ala Asn Glu His Glu Ile Val Pro
            580                 585                 590

Leu Ile Leu Glu Tyr Arg Lys Ile Gln Lys Leu Lys Ser Thr Tyr Ile
    595                 600                 605

Asp Thr Leu Pro Lys Leu Val Asn Pro Lys Thr Gly Arg Ile His Ala
    610                 615                 620
```

```
Ser Phe His Gln Thr Gly Thr Ala Thr Gly Arg Leu Ser Ser Ser Asp
625                 630                 635                 640

Pro Asn Leu Gln Asn Leu Pro Thr Lys Ser Glu Glu Gly Lys Glu Ile
            645                 650                 655

Arg Lys Ala Ile Val Pro Gln Asp Pro Asp Trp Trp Ile Val Ser Ala
            660                 665                 670

Asp Tyr Ser Gln Ile Glu Leu Arg Ile Leu Ala His Leu Ser Gly Asp
            675                 680                 685

Glu Asn Leu Val Lys Ala Phe Glu Gly Ile Asp Val His Thr Leu
    690                 695                 700

Thr Ala Ser Arg Ile Tyr Asn Val Lys Pro Glu Glu Val Asn Glu Glu
705                 710                 715                 720

Met Arg Arg Val Gly Lys Met Val Asn Phe Ser Ile Ile Tyr Gly Val
                725                 730                 735

Thr Pro Tyr Gly Leu Ser Val Arg Leu Gly Ile Pro Val Lys Glu Ala
            740                 745                 750

Glu Lys Met Ile Ile Ser Tyr Phe Thr Leu Tyr Pro Lys Val Arg Ser
            755                 760                 765

Tyr Ile Gln Gln Val Val Ala Glu Ala Lys Glu Lys Gly Tyr Val Arg
770                 775                 780

Thr Leu Phe Gly Arg Lys Arg Asp Ile Pro Gln Leu Met Ala Arg Asp
785                 790                 795                 800

Lys Asn Thr Gln Ser Glu Gly Glu Arg Ile Ala Ile Asn Thr Pro Ile
            805                 810                 815

Gln Gly Thr Ala Ala Asp Ile Ile Lys Leu Ala Met Ile Asp Ile Asp
            820                 825                 830

Glu Glu Leu Arg Lys Arg Asn Met Lys Ser Arg Met Ile Ile Gln Val
        835                 840                 845

His Asp Glu Leu Val Phe Glu Val Pro Asp Glu Glu Lys Glu Glu Leu
    850                 855                 860

Val Asp Leu Val Lys Asn Lys Met Thr Asn Val Val Lys Leu Ser Val
865                 870                 875                 880

Pro Leu Glu Val Asp Ile Ser Ile Gly Lys Ser Trp Ser
                885                 890
```

(2) INFORMATION FOR SEQ ID NO:10:

(i) SEQUENCE CHARACTERISTICS:
        (A) LENGTH: 610 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:10:

```
Met Lys Glu Leu Gln Leu Tyr Glu Glu Ala Glu Pro Thr Gly Tyr Glu
1               5                   10                  15

Ile Val Lys Asp His Lys Thr Phe Glu Asp Leu Ile Glu Lys Leu Lys
                20                  25                  30

Glu Val Pro Ser Phe Ala Leu Asp Leu Glu Thr Ser Ser Leu Asp Pro
            35                  40                  45

Phe Asn Cys Glu Ile Val Gly Ile Ser Val Ser Phe Lys Pro Lys Thr
    50                  55                  60

Ala Tyr Tyr Ile Pro Leu His His Arg Asn Ala Gln Asn Leu Asp Glu
65                  70                  75                  80
```

-continued

```
Thr Leu Val Leu Ser Lys Leu Lys Glu Ile Leu Glu Asp Pro Ser Ser
                85                  90                  95

Lys Ile Val Gly Gln Asn Leu Lys Tyr Asp Tyr Lys Val Leu Met Val
            100                 105                 110

Lys Gly Ile Ser Pro Val Tyr Pro His Phe Asp Thr Met Ile Ala Ala
            115                 120                 125

Tyr Leu Leu Glu Pro Asn Glu Lys Lys Phe Asn Leu Glu Asp Leu Ser
    130                 135                 140

Leu Lys Phe Leu Gly Tyr Lys Met Thr Ser Tyr Gln Glu Leu Met Ser
145             150                 155                 160

Phe Ser Ser Pro Leu Phe Gly Phe Ser Phe Ala Asp Val Pro Val Asp
                165                 170                 175

Lys Ala Ala Asn Tyr Ser Cys Glu Asp Ala Asp Ile Thr Tyr Arg Leu
            180                 185                 190

Tyr Lys Ile Leu Ser Met Lys Leu His Glu Ala Glu Leu Glu Asn Val
            195                 200                 205

Phe Tyr Arg Ile Glu Met Pro Leu Val Asn Val Leu Ala Arg Met Glu
    210                 215                 220

Leu Asn Gly Val Tyr Val Asp Thr Glu Phe Leu Lys Lys Leu Ser Glu
225             230                 235                 240

Glu Tyr Gly Lys Lys Leu Glu Glu Leu Ala Glu Lys Ile Tyr Gln Ile
            245                 250                 255

Ala Gly Glu Pro Phe Asn Ile Asn Ser Pro Lys Gln Val Ser Lys Ile
            260                 265                 270

Leu Phe Glu Lys Leu Gly Ile Lys Pro Arg Gly Lys Thr Thr Lys Thr
    275                 280                 285

Gly Glu Tyr Ser Thr Arg Ile Glu Val Leu Glu Glu Ile Ala Asn Glu
    290                 295                 300

His Glu Ile Val Pro Leu Ile Leu Glu Tyr Arg Lys Ile Gln Lys Leu
305             310                 315                 320

Lys Ser Thr Tyr Ile Asp Thr Leu Pro Lys Leu Val Asn Pro Lys Thr
            325                 330                 335

Gly Arg Ile His Ala Ser Phe His Gln Thr Gly Thr Ala Thr Gly Arg
            340                 345                 350

Leu Ser Ser Ser Asp Pro Asn Leu Gln Asn Leu Pro Thr Lys Ser Glu
    355                 360                 365

Glu Gly Lys Glu Ile Arg Lys Ala Ile Val Pro Gln Asp Pro Asp Trp
    370                 375                 380

Trp Ile Val Ser Ala Asp Tyr Ser Gln Ile Glu Leu Arg Ile Leu Ala
385             390                 395                 400

His Leu Ser Gly Asp Glu Asn Leu Val Lys Ala Phe Glu Glu Gly Ile
                405                 410                 415

Asp Val His Thr Leu Thr Ala Ser Arg Ile Tyr Asn Val Lys Pro Glu
            420                 425                 430

Glu Val Asn Glu Glu Met Arg Arg Val Gly Lys Met Val Asn Phe Ser
            435                 440                 445

Ile Ile Tyr Gly Val Thr Pro Tyr Gly Leu Ser Val Arg Leu Asn Ile
    450                 455                 460

Pro Val Lys Glu Ala Glu Lys Met Ile Ile Ser Tyr Phe Thr Leu Tyr
465             470                 475                 480

Pro Lys Val Arg Ser Tyr Ile Gln Gln Val Val Ala Glu Ala Lys Glu
            485                 490                 495

Lys Gly Tyr Val Arg Thr Leu Phe Gly Arg Lys Arg Asp Ile Pro Gln
```

```
                500             505             510
Leu Met Ala Arg Asp Lys Asn Thr Gln Ser Glu Gly Glu Arg Ile Ala
            515                 520             525

Ile Asn Thr Pro Ile Gln Gly Thr Ala Ala Asp Ile Ile Lys Leu Ala
    530                 535                 540

Met Ile Asp Ile Asp Glu Glu Leu Arg Lys Arg Asn Met Lys Ser Arg
545                 550                 555                 560

Met Ile Ile Gln Val His Asp Glu Leu Val Phe Glu Val Pro Asp Glu
                565                 570                 575

Glu Lys Glu Glu Leu Val Asp Leu Val Lys Asn Lys Met Thr Asn Val
            580                 585                 590

Val Lys Leu Ser Val Pro Leu Glu Val Asp Ile Ser Ile Gly Lys Ser
            595                 600                 605

Trp Ser
    610

(2) INFORMATION FOR SEQ ID NO:11:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (ii) MOLECULE TYPE: peptide (ix) FEATURE:
        (A) NAME/KEY: Modified-site
        (B) LOCATION: 1..14
        (D) OTHER INFORMATION: /note= "'Xaa' is any amino acid"

(xi) SEQUENCE DESCRIPTION: SEQ ID NO:11:

Arg Xaa Xaa Xaa Lys Xaa Xaa Xaa Phe Xaa Xaa Xaa Tyr Xaa
1               5                   10

(2) INFORMATION FOR SEQ ID NO:12:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:12:

Arg Arg Ser Ala Lys Ala Ile Asn Phe Gly Leu Ile Tyr Gly
1               5                   10

(2) INFORMATION FOR SEQ ID NO:13:

(i) SEQUENCE CHARACTERISTICS:
        (A) LENGTH: 14 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:13:

Arg Arg Ala Ala Lys Thr Ile Asn Phe Gly Val Leu Tyr Gly
1               5                   10

(2) INFORMATION FOR SEQ ID NO:14:
```

```
        (i) SEQUENCE CHARACTERISTICS:
            (A) LENGTH: 14 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:14:

Arg Asp Asn Ala Lys Thr Phe Ile Tyr Gly Phe Leu Tyr Gly
1               5                   10

(2) INFORMATION FOR SEQ ID NO:15:

(i) SEQUENCE CHARACTERISTICS:
            (A) LENGTH: 14 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:15:

Arg Arg Val Gly Lys Met Val Asn Phe Ser Ile Ile Tyr Gly
1               5                   10

(2) INFORMATION FOR SEQ ID NO:16:

(i) SEQUENCE CHARACTERISTICS:
            (A) LENGTH: 14 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:16:

Arg Gln Ala Ala Lys Ala Ile Thr Phe Gly Ile Leu Tyr Gly
1               5                   10

(2) INFORMATION FOR SEQ ID NO:17:

(i) SEQUENCE CHARACTERISTICS:
            (A) LENGTH: 14 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:17:

Arg Arg Ala Gly Lys Met Val Asn Phe Ser Ile Ile Tyr Gly
1               5                   10

(2) INFORMATION FOR SEQ ID NO:18:

(i) SEQUENCE CHARACTERISTICS:
            (A) LENGTH: 11 amino acids
            (B) TYPE: amino acid
            (C) STRANDEDNESS: Not Relevant
            (D) TOPOLOGY: linear (ii) MOLECULE TYPE: peptide (xi) SEQUENCE DESCRIPTION: SEQ ID NO:18:

Pro Ser Phe Ala Leu Asp Leu Glu Thr Ser Ser
1               5                   10

(2) INFORMATION FOR SEQ ID NO:19:
```

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:19:

Pro Val Phe Ala Phe Asp Thr Glu Thr Asp Ser
1               5                   10

(2) INFORMATION FOR SEQ ID NO:20:

(i) SEQUENCE CHARACTERISTICS:
        (A) LENGTH: 11 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:20:

Gly Pro Val Ala Phe Asp Ser Glu Thr Ser Ala
1               5                   10

(2) INFORMATION FOR SEQ ID NO:21:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:21:

Met Ile Val Ser Asp Ile Glu Ala Asn Ala
1               5                   10

(2) INFORMATION FOR SEQ ID NO:22:

(i) SEQUENCE CHARACTERISTICS:
        (A) LENGTH: 26 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:22:

GACGTTTCAA GCGCTAGGGC AAAAGA                                            26

(2) INFORMATION FOR SEQ ID NO:23:

(i) SEQUENCE CHARACTERISTICS:
        (A) LENGTH: 31 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:23:

GTATATTATA GAGTAGTTAA CCATCTTTCC A                                      31

(2) INFORMATION FOR SEQ ID NO:24:

```
    (i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (xi) SEQUENCE DESCRIPTION: SEQ ID NO:24:

Phe Leu Phe Asp Gly Thr
1               5

(2) INFORMATION FOR SEQ ID NO:25:

(i) SEQUENCE CHARACTERISTICS:
        (A) LENGTH: 6 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:25:

Leu Leu Val Asp Gly His
1               5

(2) INFORMATION FOR SEQ ID NO:26:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:26:

Ser Leu Ile Thr Gly Asp Lys Asp Met Leu
1               5                   10

(2) INFORMATION FOR SEQ ID NO:27:

(i) SEQUENCE CHARACTERISTICS:
        (A) LENGTH: 10 amino acids
        (B) TYPE: amino acid
        (C) STRANDEDNESS: Not Relevant
        (D) TOPOLOGY: linear (ii) MOLECULE TYPE: peptide (xi) SEQUENCE DESCRIPTION: SEQ ID NO:27:

Arg Ile Leu Thr Ala Asp Lys Asp Leu Tyr
1               5                   10

(2) INFORMATION FOR SEQ ID NO:28:

(i) SEQUENCE CHARACTERISTICS:
        (A) LENGTH: 35 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:28:

GTAGGCCAGG GCTGTGCCGG CAAAGAGAAA TAGTC                              35

(2) INFORMATION FOR SEQ ID NO:29:

(i) SEQUENCE CHARACTERISTICS:
        (A) LENGTH: 35 base pairs
```

(B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:29:

GAAGCATATC CTTGGCGCCG GTTATTATGA AAATC                                35

(2) INFORMATION FOR SEQ ID NO:30:

(i) SEQUENCE CHARACTERISTICS:
    (A) LENGTH: 30 base pairs
    (B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:30:

CACCAGACGG GTACCGCCAC TGGCAGGTTG                                      30

(2) INFORMATION FOR SEQ ID NO:31:

(i) SEQUENCE CHARACTERISTICS:
    (A) LENGTH: 48 base pairs
    (B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:31:

TATAGAGTAG TTAACCATCT TTCCAACCCG TTTCATTTCT TCGAACAC                  48

(2) INFORMATION FOR SEQ ID NO:32:

(i) SEQUENCE CHARACTERISTICS:
    (A) LENGTH: 48 base pairs
    (B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:32:

TATAGAGTAG TTAACCATCT TTCCAACCCG TTGCATTTCT TCGAACAC                  48

(2) INFORMATION FOR SEQ ID NO:33:

(i) SEQUENCE CHARACTERISTICS:
    (A) LENGTH: 48 base pairs
    (B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:33:

TATAGAGTAG TTAACCATCT TTCCAACCCG GTTCATTTCT TCGAACAC                  48

(2) INFORMATION FOR SEQ ID NO:34:

(i) SEQUENCE CHARACTERISTICS:
    (A) LENGTH: 48 base pairs
    (B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:34:

TATAGAGTAG TTAACCATCT TTCCAACCCG ATGCATTTCT TCGAACAC          48

(2) INFORMATION FOR SEQ ID NO:35:

(i) SEQUENCE CHARACTERISTICS:
            (A) LENGTH: 29 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:35:

AAGATGGTTA ACGCGTCTAT AATATACGG                               29

(2) INFORMATION FOR SEQ ID NO:36:

(i) SEQUENCE CHARACTERISTICS:
            (A) LENGTH: 23 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:36:

CAAGAGGCAC AGAGAGTTTC ACC                                     23

(2) INFORMATION FOR SEQ ID NO:37:

(i) SEQUENCE CHARACTERISTICS:
            (A) LENGTH: 30 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:37:

GTATATTATA GAGGAGTTAA CCATCTTTCC                              30

(2) INFORMATION FOR SEQ ID NO:38:

(i) SEQUENCE CHARACTERISTICS:
            (A) LENGTH: 29 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:38:

AAGATGGTTA ACTTCTCTAT AATATACGG                               29

(2) INFORMATION FOR SEQ ID NO:39:

(i) SEQUENCE CHARACTERISTICS:
            (A) LENGTH: 48 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:39:

```
TATAGAGTAG TTAACCATCT TTCCAACCCG GTACATGTCT TCGTTCAC                48
```

(2) INFORMATION FOR SEQ ID NO:40:

(i) SEQUENCE CHARACTERISTICS:
        (A) LENGTH: 48 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:40:

```
TATAGAGTAG TTAACCATCT TTCCAACCCG CAACATGTCT TCGTTCAC                48
```

(2) INFORMATION FOR SEQ ID NO:41:

(i) SEQUENCE CHARACTERISTICS:
        (A) LENGTH: 27 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:41:

```
CTTGGCCGCC CGATGCATCA GGGGGTC                                      27
```

(2) INFORMATION FOR SEQ ID NO:42:

(i) SEQUENCE CHARACTERISTICS:
        (A) LENGTH: 30 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:42:

```
CTTGGCCGCC CGCTTCATGA GGGGGTCCAC                                   30
```

(2) INFORMATION FOR SEQ ID NO:43:

(i) SEQUENCE CHARACTERISTICS:
        (A) LENGTH: 27 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:43:

```
CTTGGCCGCC CTGTACATCA GGGGGTC                                      27
```

(2) INFORMATION FOR SEQ ID NO:44:

(i) SEQUENCE CHARACTERISTICS:
        (A) LENGTH: 30 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:44:

```
GTATATTATA GAGGTGTTAA CCATCTTTCC                                   30
```

(2) INFORMATION FOR SEQ ID NO:45:

(i) SEQUENCE CHARACTERISTICS:
    (A) LENGTH: 34 base pairs
    (B) TYPE: nucleic acid
    (C) STRANDEDNESS: both
    (D) TOPOLOGY: both (ii) MOLECULE TYPE: cDNA (xi) SEQUENCE DESCRIPTION: SEQ ID NO:45:

GGGAGACCGG AATTCTCCTT CATTAATTCC TATA                         34

(2) INFORMATION FOR SEQ ID NO:46:

(i) SEQUENCE CHARACTERISTICS:
        (A) LENGTH: 49 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:46:

TGGAGACCCT GGAACTATAG GAATTAATGA AGGAGAATTC CGGTCTCCC         49

(2) INFORMATION FOR SEQ ID NO:47:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:47:

GTATTTTGGT ATGCTTGTGC                                         20

(2) INFORMATION FOR SEQ ID NO:48:

(i) SEQUENCE CHARACTERISTICS:
        (A) LENGTH: 22 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:48:

CTATTTTGGA ATATATGTGC CT                                      22

(2) INFORMATION FOR SEQ ID NO:49:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:49:

ACGAACATTC TACAAGTTAC                                         20

(2) INFORMATION FOR SEQ ID NO:50:

(i) SEQUENCE CHARACTERISTICS:
        (A) LENGTH: 20 base pairs
        (B) TYPE: nucleic acid

```
        (C) STRANDEDNESS: both
        (D) TOPOLOGY: both (ii) MOLECULE TYPE: cDNA (xi) SEQUENCE DESCRIPTION: SEQ ID NO:50:

TTTCAGAGAA ACTGACCTGT                                                    20

(2) INFORMATION FOR SEQ ID NO:51:

(i) SEQUENCE CHARACTERISTICS:
        (A) LENGTH: 21 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:51:

GATAAATGCC AAACATGTTG T                                                  21

(2) INFORMATION FOR SEQ ID NO:52:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:52:

TGCTCTCAGG ATTTCCTCCA                                                    20

(2) INFORMATION FOR SEQ ID NO:53:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:53:

AGCTTGAGAC CTCTGTGTCC                                                    20

(2) INFORMATION FOR SEQ ID NO:54:

(i) SEQUENCE CHARACTERISTICS:
        (A) LENGTH: 22 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:54:

ATTCAGAAGA AACAGTGATG GT                                                 22

(2) INFORMATION FOR SEQ ID NO:55:

(i) SEQUENCE CHARACTERISTICS:
        (A) LENGTH: 23 base pairs
        (B) TYPE: nucleic acid
        (C) STRANDEDNESS: both
        (D) TOPOLOGY: both (ii) MOLECULE TYPE: cDNA
```

(xi) SEQUENCE DESCRIPTION: SEQ ID NO:55:

TTGGAGTCGC AAGCTGAACT AGC 23

(2) INFORMATION FOR SEQ ID NO:56:

(i) SEQUENCE CHARACTERISTICS:
        (A) LENGTH: 23 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:56:

GCCTGAGTGA CAGAGTGAGA ACC 23

(2) INFORMATION FOR SEQ ID NO:57:

(i) SEQUENCE CHARACTERISTICS:
        (A) LENGTH: 24 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:57:

CCCACTAGGT TGTAAGCTCC ATGA 24

(2) INFORMATION FOR SEQ ID NO:58:

(i) SEQUENCE CHARACTERISTICS:
        (A) LENGTH: 24 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:58:

TACTATGTGC CAGGCTCTGT CCTA 24

(2) INFORMATION FOR SEQ ID NO:59:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:59:

ACTCATGAAG GTGACAGTTC 20

(2) INFORMATION FOR SEQ ID NO:60:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:60:

GTGTTGTTGA CCTATTGCAT 20

(2) INFORMATION FOR SEQ ID NO:61:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:61:

ATCTCTGTTC CCTCCCTGTT                                                   20

(2) INFORMATION FOR SEQ ID NO:62:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:62:

CTTATTGGCC TTGAAGGTAG                                                   20

(2) INFORMATION FOR SEQ ID NO:63:

(i) SEQUENCE CHARACTERISTICS:
        (A) LENGTH: 23 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:63:

AGCCCGTGTT GGAACCATGA CTG                                               23

(2) INFORMATION FOR SEQ ID NO:64:

(i) SEQUENCE CHARACTERISTICS:
        (A) LENGTH: 23 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:64:

TACATAGCGA GACTCCATCT CCC                                               23

(2) INFORMATION FOR SEQ ID NO:65:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:65:

TTTATGCGAG CGTATGGATA                                                   20

(2) INFORMATION FOR SEQ ID NO:66:

(i) SEQUENCE CHARACTERISTICS:
            (A) LENGTH: 20 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:66:

CACCACCATT GATCTGGAAG                                                     20

(2) INFORMATION FOR SEQ ID NO:67:

(i) SEQUENCE CHARACTERISTICS:
            (A) LENGTH: 16 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:67:

CCAACCACAC TGGGAA                                                         16

(2) INFORMATION FOR SEQ ID NO:68:

(i) SEQUENCE CHARACTERISTICS:
            (A) LENGTH: 16 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:68:

AACAGTTGCC CACGGT                                                         16

(2) INFORMATION FOR SEQ ID NO:69:

(i) SEQUENCE CHARACTERISTICS:
            (A) LENGTH: 20 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:69:

CATGAAATGC TGACTGGGTA                                                     20

(2) INFORMATION FOR SEQ ID NO:70:

(i) SEQUENCE CHARACTERISTICS:
            (A) LENGTH: 20 base pairs
            (B) TYPE: nucleic acid
            (C) STRANDEDNESS: both
            (D) TOPOLOGY: both (ii) MOLECULE TYPE: cDNA (xi) SEQUENCE DESCRIPTION: SEQ ID NO:70:

TCAATTTATG TGCAGCCAAT                                                     20

(2) INFORMATION FOR SEQ ID NO:71:

(i) SEQUENCE CHARACTERISTICS:
            (A) LENGTH: 20 base pairs
            (B) TYPE: nucleic acid
            (C) STRANDEDNESS: both (D) TOPOLOGY: both (ii) MOLECULE TYPE: cDNA (xi) SEQUENCE DESCRIPTION: SEQ ID NO:71:

CATAGCGAGA CTCCATCTCC                                                    20

(2) INFORMATION FOR SEQ ID NO:72:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:72:

GGGAGAGGGC AAAGATCGAT                                                    20

(2) INFORMATION FOR SEQ ID NO:73:

(i) SEQUENCE CHARACTERISTICS:
        (A) LENGTH: 22 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:73:

AACACTAGTG ACATTATTTT CA                                                 22

(2) INFORMATION FOR SEQ ID NO:74:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:74:

AGCTAGGCCT GAAGGCTTCT                                                    20

(2) INFORMATION FOR SEQ ID NO:75:

(i) SEQUENCE CHARACTERISTICS:
        (A) LENGTH: 24 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:75:

CCCTAGTGGA TGATAAGAAT AATC                                               24

(2) INFORMATION FOR SEQ ID NO:76:

(i) SEQUENCE CHARACTERISTICS:
        (A) LENGTH: 30 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:76:

GGACAGATGA TAAATACATA GGATGGATGG                              30

(2) INFORMATION FOR SEQ ID NO:77:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:77:

TTCTCTTACA ACACTGCCCC                                         20

(2) INFORMATION FOR SEQ ID NO:78:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:78:

ATTTGGATGG CTTGACAGAG                                         20

(2) INFORMATION FOR SEQ ID NO:79:

(i) SEQUENCE CHARACTERISTICS:
        (A) LENGTH: 21 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:79:

ACATTCTAAG ACTTTCCCAA T                                       21

(2) INFORMATION FOR SEQ ID NO:80:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:80:

AGAGCATGCA CCCTGAATTG                                         20

(2) INFORMATION FOR SEQ ID NO:81:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:81:

AAGAACCATG CGATACGACT                                         20

(2) INFORMATION FOR SEQ ID NO:82:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:82:

CATTCCTAGA TGGGTAAAGC                                      20

(2) INFORMATION FOR SEQ ID NO:83:

(i) SEQUENCE CHARACTERISTICS:
        (A) LENGTH: 18 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:83:

GCTTAGTCAT ACGAGCGG                                        18

(2) INFORMATION FOR SEQ ID NO:84:

(i) SEQUENCE CHARACTERISTICS:
        (A) LENGTH: 18 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:84:

TCCACAGCCA TGTAAACC                                        18

(2) INFORMATION FOR SEQ ID NO:85:

(i) SEQUENCE CHARACTERISTICS:
        (A) LENGTH: 16 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:85:

CCCCGGAGCA AGTTCA                                          16

(2) INFORMATION FOR SEQ ID NO:86:

(i) SEQUENCE CHARACTERISTICS:
        (A) LENGTH: 18 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:86:

CAGCCCAAAG CCAGATTA                                        18

(2) INFORMATION FOR SEQ ID NO:87:

(i) SEQUENCE CHARACTERISTICS:

(A) LENGTH: 22 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:87:

ATATGTGAGT CAATTCCCCA AG                                               22

(2) INFORMATION FOR SEQ ID NO:88:

(i) SEQUENCE CHARACTERISTICS:
        (A) LENGTH: 22 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:88:

TGTATTAGTC AATGTTCTCC AG                                               22

(2) INFORMATION FOR SEQ ID NO:89:

(i) SEQUENCE CHARACTERISTICS:
        (A) LENGTH: 19 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:89:

CAGCTGCCCT AGTCAGCAC                                                   19

(2) INFORMATION FOR SEQ ID NO:90:

(i) SEQUENCE CHARACTERISTICS:
        (A) LENGTH: 20 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:90:

GCTTCCGAGT GCAGGTCACA                                                  20

(2) INFORMATION FOR SEQ ID NO:91:

(i) SEQUENCE CHARACTERISTICS:
        (A) LENGTH: 21 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:91:

ATTCTGGGCG CACAAGAGTG A                                                21

(2) INFORMATION FOR SEQ ID NO:92:

(i) SEQUENCE CHARACTERISTICS:
        (A) LENGTH: 20 base pairs
        (B) TYPE: nucleic acid
        (C) STRANDEDNESS: both
        (D) TOPOLOGY: both -continued

```
    (ii) MOLECULE TYPE: cDNA (xi) SEQUENCE DESCRIPTION: SEQ ID NO:92:

ACATCTCCCC TACCGCTATA                                                    20

(2) INFORMATION FOR SEQ ID NO:93:

(i) SEQUENCE CHARACTERISTICS:
        (A) LENGTH: 33 base pairs
        (B) TYPE: nucleic acid
        (C) STRANDEDNESS: both
        (D) TOPOLOGY: both (ii) MOLECULE TYPE: cDNA (xi) SEQUENCE DESCRIPTION: SEQ ID NO:93:

GAAGTTCACC ATCCGGCCGA CCCGTCGCAT TTC                                     33
```